US012673941B2

(12) United States Patent
Uesugi et al.

(10) Patent No.: US 12,673,941 B2
(45) Date of Patent: Jul. 7, 2026

(54) TERTIARY AMIDE DERIVATIVES SUBSTITUTED WITH 4-MEMBERED RING STRUCTURE

(71) Applicants: Sumitomo Pharma Co., Ltd., Osaka (JP); NATIONAL CANCER CENTER, Tokyo (JP)

(72) Inventors: Shunichiro Uesugi, Osaka (JP); Yusuke Kamei, Osaka (JP); Hitoshi Ban, Osaka (JP); Seiji Kamioka, Osaka (JP); Yusuke Imazaki, Osaka (JP); Hideaki Ogiwara, Tokyo (JP); Mariko Sasaki, Tokyo (JP)

(73) Assignees: Sumitomo Pharma Co., Ltd., Osaka (JP); NATIONAL CANCER CENTER, Tokyo (JP)

( * ) Notice: Subject to any disclaimer, the term of this patent is extended or adjusted under 35 U.S.C. 154(b) by 0 days.

(21) Appl. No.: 19/177,218

(22) Filed: Apr. 11, 2025

(65) Prior Publication Data

US 2025/0257055 A1 Aug. 14, 2025

Related U.S. Application Data

(63) Continuation of application No. 19/047,358, filed on Feb. 6, 2025.

(51) Int. Cl.

| | |
|---|---|
| ***C07D 405/14*** | (2006.01) |
| ***A61K 31/4184*** | (2006.01) |
| ***A61K 31/4439*** | (2006.01) |
| ***A61K 31/4545*** | (2006.01) |
| ***A61K 31/4985*** | (2006.01) |
| ***A61K 45/06*** | (2006.01) |
| ***A61P 35/00*** | (2006.01) |

(Continued)

(52) U.S. Cl.

CPC ........ *C07D 405/14* (2013.01); *A61K 31/4184* (2013.01); *A61K 31/4439* (2013.01); *A61K 31/4545* (2013.01); *A61K 31/4985* (2013.01); *A61K 45/06* (2013.01); *A61P 35/00* (2018.01); *C07D 401/14* (2013.01); *C07D 403/14* (2013.01); *C07D 487/04* (2013.01)

(58) Field of Classification Search

CPC ... A61K 31/4439; A61P 35/00; C07D 401/14; C07D 403/14

See application file for complete search history.

(56) References Cited

U.S. PATENT DOCUMENTS

2022/0087996 A1 3/2022 Fan et al.

FOREIGN PATENT DOCUMENTS

| | | |
|---|---|---|
| JP | 2022-510874 A | 1/2022 |
| WO | WO 2016/044770 A1 | 3/2016 |

(Continued)

OTHER PUBLICATIONS

Goll et al.,"Histone modification and replacement in chromatin activation", Genes & Development 16, pp. 1739-1742, 2002.

(Continued)

*Primary Examiner* — Savitha M Rao
*Assistant Examiner* — Elena V Vishnyakova
(74) *Attorney, Agent, or Firm* — Oblon, McClelland, Maier & Neustadt, L.L.P.

(57) ABSTRACT

[Problem] The present disclosure provides tertiary amide derivatives substituted with a 4-membered ring structure that are useful as medicines and pharmaceutically acceptable salts thereof, pharmaceutical compositions comprising the same, and therapeutic agents and/or prophylactic agents for conditions in which CBP/P300 is involved, comprising the composition.

[Solving Means] More specifically, the present disclosure provides a compound represented by the following Formula (1):

(1)

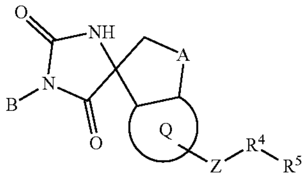

wherein A represents CHF, or $CH_2$, B represents the following Formula (B-1):

(B-1)

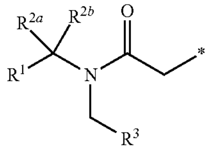

Ring Q represents an optionally substituted 6- to 10-membered aromatic hydrocarbon ring, or an optionally substituted 5- to 10-membered aromatic heterocycle, Z represents —O—, —N($R^{7a}$)—, an optionally substituted 6- to 10-membered divalent aromatic ring group, an optionally substituted 5- to 10-membered divalent aromatic heterocyclic group, an optionally substituted 4- to 10-membered divalent non-aryl heterocyclic group, and $R^1$, $R^{2a}$, $R^{2b}$, $R^3$, $R^4$, and $R^5$ are as described in the specification, or a pharmaceutically acceptable salt thereof.

8 Claims, No Drawings

Specification includes a Sequence Listing.

(51) Int. Cl.

| | |
|---|---|
| ***C07D 401/14*** | (2006.01) |
| ***C07D 403/14*** | (2006.01) |
| ***C07D 487/04*** | (2006.01) |

(56) References Cited

FOREIGN PATENT DOCUMENTS

| | | | |
|---|---|---|---|
| WO | WO 2019/049061 | A1 | 3/2019 |
| WO | WO 2019/111980 | A1 | 6/2019 |
| WO | WO 2019/161157 | A1 | 8/2019 |
| WO | WO 2019/161162 | A1 | 8/2019 |
| WO | WO 2019/201291 | A1 | 10/2019 |
| WO | WO 2018/235966 | A1 | 4/2020 |
| WO | WO 2020/108500 | A1 | 6/2020 |
| WO | WO 2020/176558 | A1 | 9/2020 |
| WO | WO 2020/198567 | A1 | 10/2020 |
| WO | WO 2022/138944 | A1 | 6/2022 |

OTHER PUBLICATIONS

Dutta et al., "CBP/p300 acetyltransferase activity in hematologic malignancies", Molecular Genetics and Metabolism 119, pp. 37-43, 2016.

Yee et al., "Detection of Cellular Proteins Associated with Human Adenovirus Type 5 Early Region 1A Polypeptides", Virology 147, pp. 142-153, 1985.

Harlow et al., "Association of Adenovirus Early-Region 1A Proteins with Cellular Polypeptides", Molecular and Cellular Biology, pp. 1579-1589, 1986.

Chrivia et al., "Phosphorylated CREB binds specifically to the nuclear protein CBP", Nature, vol. 365, pp. 855-859, 1993.

Ogryzko et al., "The Transcriptional Coactivators p300 and CBP Are Histone Acetyltransferases", Cell, vol. 87, pp. 953-959, 1996.

Bannister et al., "The CBP co-activator is a histone acetyltransferase", Nature, vol. 384, pp. 641-643, 1996.

Gu et al., "Activation of p53 Sequence-Specific DNA Binding by Acetylation of the p53 C-Terminal Domain", Cell, vol. 90, pp. 595-606, 1997.

Polesskaya et al., "CREB-binding Protein/p300 Activates MyoD by Acetylation*", The Journal of Biological Chemistry, vol. 275, pp. 34359-34364, 2000.

Yuan et al., "Stat3 Dimerization Regulated by Reversible Acetylation of a Single Lysine Residue", Science, vol. 307, pp. 269-273, 2005.

Fu et al., "p300 and p300/cAMP-response Element-binding Protein-associated Factor Acetylate the Androgen Receptor at Sites Governing Hormone-dependent Transactivation*", The Journal of Biological Chemistry, pp. 20853-20860, 2000.

Chan et al., "p300/CBP proteins: HATs for transcriptional bridges and scaffolds", Journal of Cell Science, 114, pp. 2363-2373, 2001.

Heemers et al., "The role of the transcriptional coactivator p300 in prostate cancer progression", Adv Exp Med Biol., 617, pp. 535-540, 2008.

Isharwal et al., "p300 (Histone Acetyltransferase) biomarker predicts prostate cancer biochemical recurrence and correlates with changes in epithelia nuclear size and shape", Prostate, 68, pp. 1097-1104, 2008.

Yokomizo et al., "High expression of p300 in HCC predicts shortened overall survival in association with enhanced epithelial mesenchymal transition of HCC cells", Cancer Letters, 310, pp. 140-147, 2011.

Li et al., "High expression of transcriptional coactivator p300 correlates with aggressive features and poor prognosis of hepatocellular carcinoma", Journal of Translational Medicine, 9:5, 11 pages, 2011.

Gao et al., "Expression of p300 and CBP is associated with poor prognosis in small cell lung cancer", Int J Clin Exp Pathol., 7(2), pp. 760-767, 2014.

Peifer et al., "Integrative genome analyses identify key somatic driver mutations of small cell lung cancer", Nat Genet., 44(10), pp. 1104-1110, 2012.

Kishimoto et al., "Mutations and Deletions of the CBP Gene in Human Lung Cancer", Clinical Cancer Research, vol. 11, pp. 512-519, 2005.

Zhao et al., "The adenoviral E1A N-terminal domain represses MYC transcription in human cancer cells by targeting both p300 and TRRAP and inhibiting MYC promoter acetylation of H3K18 and H4K16", Genes & Cancer, vol. 7 (3-4), pp. 98-109, 2016.

Muraoka et al., "p300 gene alterations in colorectal and gastric carcinomas", Oncogene, 12, pp. 1565-1569, 1996.

Sobulo et al., "MLL is fused to CBP, a histone acetyltransferase, in therapy-related acute myeloid leukemia with a t(11;16)(q23;p13.3)", Proc. Natl. Acad. Sci. USA, vol. 94, pp. 8732-8737, 1997.

Saeed et al., "Chromatin accessibility, p300, and histone acetylation define PML-RARα and AML1-ETO binding sites in acute myeloid leukemia", Blood, vol. 120, pp. 3058-3068, 2012.

Gayther et al., "Mutations truncating the EP300 acetylase in human cancers", Nature Genetics, vol. 24, pp. 300-303, 2000.

Gui et al., "Frequent mutations of chromatin remodeling genes in transitional cell carcinoma of the bladder", Nat Genet., 43(9), pp. 875-878, 2011.

Gu et al., "An inhibitor of the acetyltransferases CBP/p300 exerts antineoplastic effects on gastrointestinal stromal tumor cells", Oncology Reports, 36, pp. 2763-2770, 2016.

Wang et al., "Mechanistic Analysis of the Role of Bromodomain-containing Protein 4 (BRD4) in BRD4-NUT Oncoprotein-induced Transcriptional Activation*", The Journal of Biological Chemistry, vol. 290, pp. 2744-2758, 2015.

Cianfrocca et al., "Nuclear ß-arrestin1 is a critical cofactor of hypoxia-inducible factor-1 α signaling in endothelin-1-induced ovarian tumor progression", Oncotarget, vol. 7, No. 14, pp. 17790-17804, 2016.

Ji et al., "Discovery of spirohydantoins as selective, orally bioavailable inhibitors of p300/CBP histone acetyltransferases", Bioorg. Med. Chem. Lett., 39, pp. 127854-127859, 2021.

Michaelides et al., "Discovery of Spiro Oxazolidinediones as Selective, Orally Bioavailable Inhibitors of p300/CBP Histone Acetyltransferases", ACS Med. Chem. vol. 9, pp. 28-33, 2018.

Registry (STN) [online], 2003 (Search date: Feb. 26, 2024) , CAS Registry No. 565225-21-0.

International Search Report and Written Opinion issued May 7, 2024 in International Application No. PCT/JP2024/004222 filed on Feb. 7, 2024, 9 pages, with partial English translation of Written Opinion.

```
                       SEQUENCE LISTING


Sequence total quantity: 3
SEQ ID NO: 1          moltype = AA  length = 2442
FEATURE               Location/Qualifiers
source                1..2442
                      mol_type = protein
                      organism = Homo sapiens
SEQUENCE: 1
MAENLLDGPP NPKRAKLSSP GFSANDSTDF GSLFDLENDL PDELIPNGGE LGLLNSGNLV  60
PDAASKHKQL SELLRGGSGS SINPGIGNVS ASSPVQQGLG GQAQGQPNSA NMASLSAMGK  120
SPLSQGDSSA PSLPKQAAST SGPTPAASQA LNPQAQKQVG LATSSPATSQ TGPGICMNAN  180
```

-continued

```
FNQTHPGLLN SNSGHSLINQ ASQGQAQVMN GSLGAAGRGR GAGMPYPTPA MQGASSSVLA  240
ETLTQVSPQM TGHAGLNTAQ AGGMAKMGIT GNTSPFGQPF SQAGGQPMGA TGVNPQLASK  300
QSMVNSLPTF PTDIKNTSVT NVPNMSQMQT SVGIVPTQAI ATGPTADPEK RKLIQQQLVL  360
LLHAHKCQRR EQANGEVRAC SLPHCRTMKN VLNHMTHCQA GKACQVAHCA SSRQIISHWK  420
NCTRHDCPVC LPLKNASDKR NQQTILGSPA SGIQNTIGSV GTGQQNATSL SNPNPIDPSS  480
MQRAYAALGL PYMNQPQTQL QPQVPGQQPA QPQTHQQMRT LNPLGNNPMN IPAGGITTDQ  540
QPPNLISESA LPTSLGATNP LMNDGSNSGN IGTLSTIPTA APPSSTGVRK GWHEHVTQDL  600
RSHLVHKLVQ AIFPTPDPAA LKDRRMENLV AYAKKVEGDM YESANSRDEY YHLLAEKIYK  660
IQKELEEKRR SRLHKQGILG NQPALPAPGA QPPVIPQAQP VRPPNGPLSL PVNRMQVSQG  720
MNSFNPMSLG NVQLPQAPMG PRAASPMNHS VQMNSMGSVP GMAISPSRMP QPPNMMGAHT  780
NNMMAQAPAQ SQFLPQNQFP SSSGAMSVGM GQPPAQTGVS QGQVPGAALP NPLNMLGPQA  840
SQLPCPPVTQ SPLHPTPPPA STAAGMPSLQ HTTPPGMTPP QPAAPTQPST PVSSSGQTPT  900
PTPGSVPSAT QTQSTPTVQA AAQAQVTPQP QTPVQPPSVA TPQSSQQQPT PVHAQPPGTP  960
LSQAAASIDN RVPTPSSVAS AETNSQQPGP DVPVLEMKTE TQAEDTEPDP GESKGEPRSE  1020
MMEEDLQGAS QVKEETDIAE QKSEPMEVDE KKPEVKVEVK EEEESSSNGT ASQSTSPSQP  1080
RKKIFKPEEL RQALMPTLEA LYRQDPESLP FRQPVDPQLL GIPDYFDIVK NPMDLSTIKR  1140
KLDTGQYQEP WQYVDDVWLM FNNAWLYNRK TSRVYKFCSK LAEVFEQEID PVMQSLGYCC  1200
GRKYEFSPQT LCCYGKQLCT IPRDAAYYSY QNRYHFCEKC FTEIQGENVT LGDDPSQPQT  1260
TISKDQFEKK KNDTLDPEPF VDCKECGRKM HQICVLHYDI IWPSGFVCDN CLKKTGRPRK  1320
ENKFSAKRLQ TTRLGNHLED RVNKFLRRQN HPEAGEVFVR VVASSDKTVE VKPGMKSRFV  1380
DSGEMSESFP YRTKALFAFE EIDGVDVCFF GMHVQEYGSD CPPPNTRRVY ISYLDSIHFF  1440
RPRCLRTAVY HEILIGYLEY VKKLGYVTGH IWACPPSEGD DYIFHCHPPD QKIPKPKRLQ  1500
EWYKKMLDKA FAERIIHDYK DIFKQATEDR LTSAKELPYF EGDFWPNVLE ESIKELEQEE  1560
EERKKEESTA ASETTEGSQG DSKNAKKKNN KKTNKNKSSI SRANKKKPSM PNVSNDLSQK  1620
LYATMEKHKE VFFVIHLHAG PVINTLPPIV DPDPLLSCDL MDGRDAFLTL ARDKHWEFSS  1680
LRRSKWSTLC MLVELHTQGQ DRFVYTCNEC KHHVETRWHC TVCEDYDLCI NCYNTKSHAH  1740
KMVKWGLGLD DEGSSQGEPQ SKSPQESRRL SIQRCIQSLV HACQCRNANC SLPSCQKMKR  1800
VVQHTKGCKR KTNGGCPVCK QLIALCCYHA KHCQENKCPV PFCLNIKHKL RQQQIQHRLQ  1860
QAQLMRRRMA TMNTRNVPQQ SLPSPTSAPP GTPTQQPSTP QTPQPPAQPQ PSPVSMSPAG  1920
FPSVARTQPP TTVSTGKPTS QVPAPPPPAQ PPPAAVEAAR QIEREAQQQQ HLYRVNINNS  1980
MPPGRTGMGT PGSQMAPVSL NVPRPNQVSG PVMPSMPPGQ WQQAPLPQQQ PMPGLPRPVI  2040
SMQAQAAVAG PRMPSVQPPR SISPSALQDL LRTLKSPSSP QQQQQVLNIL KSNPQLMAAF  2100
IKQRTAKYVA NQPGMQPQPG LQSQPGMQPQ PGMHQQPSLQ NLNAMQAGVP RPGVPPQQQA  2160
MGGLNPQGQA LNIMNPGHNP NMASMNPQYR EMLRRQLLQQ QQQQQQQQQ QQQQQQGSAG  2220
MAGGMAGHGQ FQQPQGPGGY PPAMQQQQRM QQHLPLQGSS MGQMAAQMGQ LGQMGQPGLG  2280
ADSTPNIQQA LQQRILQQQQ MKQQIGSPGQ PNPMSPQQHM LSGQPQASHL PGQQIATSLS  2340
NQVRSPAPVQ SPRPQSQPPH SSPSPRIQPQ PSPHHVSPQT GSPHPGLAVT MASSIDQGHL  2400
GNPEQSAMLP QLNTPSRSAL SSELSLVGDT TGDTLEKFVE GL                     2442

SEQ ID NO: 2           moltype = AA  length = 2404
FEATURE                Location/Qualifiers
source                 1..2404
                       mol_type = protein
                       organism = Homo sapiens
SEQUENCE: 2
MAENLLDGPP NPKRAKLSSP GFSANDSTDF GSLFDLENDL PDELIPNGGE LGLLNSGNLV  60
PDAASKHKQL SELLRGGSGS SINPGIGNVS ASSPVQQGLG GQAQGQPNSA NMASLSAMGK  120
SPLSQGDSSA PSLPKQAAST SGPTPAASQA LNPQAQKQVG LATSSPATSQ TGPGICMNAN  180
FNQTHPGLLN SNSGHSLINQ ASQGQAQVMN GSLGAAGRGR GAGMPYPTPA MQGASSSVLA  240
ETLTQVSPQM TGHAGLNTAQ AGGMAKMGIT GNTSPFGQPF SQAGGQPMGA TGVNPQLASK  300
QSMVNSLPTF PTDIKNTSVT NVPNMSQMQT SVGIVPTQAI ATGPTADPEK RKLIQQQLVL  360
LLHAHKCQRR EQANGEVRAC SLPHCRTMKN VLNHMTHCQA GKACQAILGS PASGIQNTIG  420
SVGTGQQNAT SLSNPNPIDP SSMQRAYAAL GLPYMNQPQT QLQPQVPGQQ PAQPQTHQQM  480
RTLNPLGNNP MNIPAGGITT DQQPPNLISE SALPTSLGAT NPLMNDGSNS GNIGTLSTIP  540
TAAPPSSTGV RKGWHEHVTQ DLRSHLVHKL VQAIFPTPDP AALKDRRMEN LVAYAKKVEG  600
DMYESANSRD EYYHLLAEKI YKIQKELEEK RRSRLHKQGI LGNQPALPAP GAQPPVIPQA  660
QPVRPPNGPL SLPVNRMQVS QGMNSFNPMS LGNVQLPQAP MGPRAASPMN HSVQMNSMGS  720
VPGMAISPSR MPQPPNMMGA HTNNMMAQAP AQSQFLPQNQ FPSSSGAMSV GMGQPPAQTG  780
VSQGQVPGAA LPNPLNMLGP QASQLPCPPV TQSPLHPTPP PASTAAGMPS LQHTTPPGMT  840
PPQPAAPTQP STPVSSSGQT PTPTPGSVPS ATQTQSTPTV QAAAQAQVTP QPQTPVQPPS  900
VATPQSSQQQ PTPVHAQPPG TPLSQAAASI DNRVPTPSSV ASAETNSQQP GPDVPVLEMK  960
TETQAEDTEP DPGESKGEPR SEMMEEDLQG ASQVKEETDI AEQKSEPMEV DEKKPEVKVE  1020
VKEEEESSSN GTASQSTSPS QPRKKIFKPE ELRQALMPTL EALYRQDPES LPFRQPVDPQ  1080
LLGIPDYFDI VKNPMDLSTI KRKLDTGQYQ EPWQYVDDVW LMFNNAWLYN RKTSRVYKFC  1140
SKLAEVFEQE IDPVMQSLGY CCGRKYEFSP QTLCCYGKQL CTIPRDAAYY SYQNRYHFCE  1200
KCFTEIQGEN VTLGDDPSQP QTTISKDQFE KKKNDTLDPE PFVDCKECGR KMHQICVLHY  1260
DIIWPSGFVC DNCLKKTGRP RKENKFSAKR LQTTRLGNHL EDRVNKFLRR QNHPEAGEVF  1320
VRVVASSDKT VEVKPGMKSR FVDSGEMSES FPYRTKALFA FEEIDGVDVC FFGMHVQEYG  1380
SDCPPPNTRR VYISYLDSIH FFRPRCLRTA VYHEILIGYL EYVKKLGYVT GHIWACPPSE  1440
GDDYIFHCHP PDQKIPKPKR LQEWYKKMLD KAFAERIIHD YKDIFKQATE DRLTSAKELP  1500
YFEGDFWPNV LEESIKELEQ EEEERKKEES TAASETTEGS QGDSKNAKKK NNKKTNKNKS  1560
SISRANKKKP SMPNVSNDLS QKLYATMEKH KEVFFVIHLH AGPVINTLPP IVDPDPLLSC  1620
DLMDGRDAFL TLARDKHWEF SSLRRSKWST LCMLVELHTQ GQDRFVYTCN ECKHHVETRW  1680
HCTVCEDYDL CINCYNTKSH AHKMVKWGLG LDDEGSSQGE PQSKSPQESR RLSIQRCIQS  1740
LVHACQCRNA NCSLPSCQKM KRVVQHTKGC KRKTNGGCPV CKQLIALCCY HAKHCQENKC  1800
PVPFCLNIKH KLRQQQIQHR LQQAQLMRRR MATMNTRNVP QQSLPSPTSA PPGTPTQQPS  1860
TPQTPQPPAQ PQPSPVSMSP AGFPSVARTQ PPTTVSTGKP TSQVPAPPPP AQPPPAAVEA  1920
ARQIEREAQQ QQHLYRVNIN NSMPPGRTGM GTPGSQMAPV SLNVPRPNQV SGPVMPSMPP  1980
GQWQQAPLPQ QQPMPGLPRP VISMQAQAAV AGPRMPSVQP PRSISPSALQ DLLRTLKSPS  2040
```

-continued

```
SPQQQQQVLN ILKSNPQLMA AFIKQRTAKY VANQPGMQPQ PGLQSQPGMQ PQPGMHQQPS  2100
LQNLNAMQAG VPRPGVPPQQ QAMGGLNPQG QALNIMNPGH NPNMASMNPQ YREMLRRQLL  2160
QQQQQQQQQQ QQQQQQQQGS AGMAGGMAGH GQFQQPQGPG GYPPAMQQQQ RMQQHLPLQG  2220
SSMGQMAAQM GQLGQMGQPG LGADSTPNIQ QALQQRILQQ QQMKQQIGSP GQPNPMSPQQ  2280
HMLSGQPQAS HLPGQQIATS LSNQVRSPAP VQSPRPQSQP PHSSPSPRIQ PQPSPHHVSP  2340
QTGSPHPGLA VTMASSIDQG HLGNPEQSAM LPQLNTPSRS ALSSELSLVG DTTGDTLEKF  2400
VEGL                                                              2404

SEQ ID NO: 3            moltype = AA  length = 2414
FEATURE                 Location/Qualifiers
source                  1..2414
                        mol_type = protein
                        organism = Homo sapiens
SEQUENCE: 3
MAENVVEPGP PSAKRPKLSS PALSASASDG TDFGSLFDLE HDLPDELINS TELGLTNGGD  60
INQLQTSLGM VQDAASKHKQ LSELLRSGSS PNLNMGVGGP GQVMASQAQQ SSPGLGLINS  120
MVKSPMTQAG LTSPNMGMGT SGPNQGPTQS TGMMNSPVNQ PAMGMNTGMN AGMNPGMLAA  180
GNGQGIMPNQ VMNGSIGAGR GRQNMQYPNP GMGSAGNLLT EPLQQGSPQM GGQTGLRGPQ  240
PLKMGMMNNP NPYGSPYTQN PGQQIGASGL GLQIQTKTVL SNNLSPFAMD KKAVPGGGMP  300
NMGQQPAPQV QQPGLVTPVA QGMGSGAHTA DPEKRKLIQQ QLVLLLHAHK CQRREQANGE  360
VRQCNLPHCR TMKNVLNHMT HCQSGKSCQV AHCASSRQII SHWKNCTRHD CPVCLPLKNA  420
GDKRNQQPIL TGAPVGLGNP SSLGVGQQSA PNLSTVSQID PSSIERAYAA LGLPYQVNQM  480
PTQPQVQAKN QQNQQPGQSP QGMRPMSNMS ASPMGVNGGV GVQTPSLLSD SMLHSAINSQ  540
NPMMSENASV PSLGPMPTAA QPSTTGIRKQ WHEDITQDLR NHLVHKLVQA IFPTPDPAAL  600
KDRRMENLVA YARKVEGDMY ESANNRAEYY HLLAEKIYKI QKELEEKRRT RLQKQNMLPN  660
AAGMVPVSMN PGPNMGQPQP GMTSNGPLPD PSMIRGSVPN QMMPRITPQS GLNQFGQMSM  720
AQPPIVPRQT PPLQHHGQLA QPGALNPPMG YGPRMQQPSN QGQFLPQTQF PSQGMNVTNI  780
PLAPSSGQAP VSQAQMSSSS CPVNSPIMPP GSQGSHIHCP QLPQPALHQN SPSPVPSRTP  840
TPHHTPPSIG AQQPPATTIP APVPTPPAMP PGPQSQALHP PPRQTPTPPT TQLPQQVQPS  900
LPAAPSADQP QQQPRSQQST AASVPTPTAP LLPPQPATPL SQPAVSIEGQ VSNPPSTSST  960
EVNSQAIAEK QPSQEVKMEA KMEVDQPEPA DTQPEDISES KVEDCKMEST ETEERSTELK  1020
TEIKEEEDQP STSATQSSPA PGQSKKKIFK PEELRQALMP TLEALYRQDP ESLPFRQPVD  1080
PQLLGIPDYF DIVKSPMDLS TIKRKLDTGQ YQEPWQYVDD IWLMFNNAWL YNRKTSRVYK  1140
YCSKLSEVFE QEIDPVMQSL GYCCGRKLEF SPQTLCCYGK QLCTIPRDAT YYSYQNRYHF  1200
CEKCFNEIQG ESVSLGDDPS QPQTTINKEQ FSKRKNDTLD PELFVECTEC GRKMHQICVL  1260
HHEIIWPAGF VCDGCLKKSA RTRKENKFSA KRLPSTRLGT FLENRVNDFL RRQNHPESGE  1320
VTVRVVHASD KTVEVKPGMK ARFVDSGEMA ESFPYRTKAL FAFEEIDGVD LCFFGMHVQE  1380
YGSDCPPPNQ RRVYISYLDS VHFFRPKCLR TAVYHEILIG YLEYVKKLGY TTGHIWACPP  1440
SEGDDYIFHC HPPDQKIPKP KRLQEWYKKM LDKAVSERIV HDYKDIFKQA TEDRLTSAKE  1500
LPYFEGDFWP NVLEESIKEL EQEEEERKRE ENTSNESTDV TKGDSKNAKK KNNKKTSKNK  1560
SSLSRGNKKK PGMPNVSNDL SQKLYATMEK HKEVFFVIRL IAGPAANSLP PIVDPDPLIP  1620
CDLMDGRDAF LTLARDKHLE FSSLRRAQWS TMCMLVELHT QSQDRFVYTC NECKHHVETR  1680
WHCTVCEDYD LCITCYNTKN HDHKMEKLGL GLDDESNNQQ AAATQSPGDS RRLSIQRCIQ  1740
SLVHACQCRN ANCSLPSCQK MKRVVQHTKG CKRKTNGGCP ICKQLIALCC YHAKHCQENK  1800
CPVPFCLNIK QKLRQQQLQH RLQQAQMLRR RMASMQRTGV VGQQQGLPSP TPATPTTPTG  1860
QQPTTPQTPQ PTSQPQPTPP NSMPPYLPRT QAAGPVSQGK AAGQVTPPTP PQTAQPPLPG  1920
PPPAAVEMAM QIQRAAETQR QMAHVQIFQR PIQHQMPPMT PMAPMGMNPP PMTRGPSGHL  1980
EPGMGPTGMQ QQPPWSQGGL PQPQQLQSGM PRPAMMSVAQ HGQPLNMAPQ PGLGQVGISP  2040
LKPGTVSQQA LQNLLRTLRS PSSPLQQQQV LSILHANPQL LAAFIKQRAA KYANSNPQPI  2100
PGQPGMPQGQ PGLQPPTMPG QQGVHSNPAM QNMNPMQAGV QRAGLPQQQP QQQLQPPMGG  2160
MSPQAQQMNM NHNTMPSQFR DILRRQQMMQ QQQQQGAGPG IGPGMANHNQ FQQPQGVGYP  2220
PQQQQRMQHH MQQMQQGNMG QIGQLPQALG AEAGASLQAY QQRLLQQQMG SPVQPNPMSP  2280
QQHMLPNQAQ SPHLQGQQIP NSLSNQVRSP QPVPSPRPQS QPPHSSPSPR MQPQPSPHHV  2340
SPQTSSPHPG LVAAQANPME QGHFASPDQN SMLSQLASNP GMANLHGASA TDLGLSTDNS  2400
DLNSNLSQST LDIH                                                    2414
```

TERTIARY AMIDE DERIVATIVES SUBSTITUTED WITH 4-MEMBERED RING STRUCTURE

CROSS-REFERENCE TO RELATED APPLICATIONS

The present application is a continuation of U.S. application Ser. No. 19/047,358, filed Feb. 6, 2025, which is based on and claims the benefits of priority to International Application of PCT/JP2024/004222, filed on Feb. 7, 2024. The entire contents of all of the above applications are incorporated herein by reference.

REFERENCE TO A SEQUENCE LISTING

In accordance with 37 CFR § 1.831-1.835 and 37 CFR § 1.77 (b) (5), the specification makes reference to a Sequence Listing filed electronically as a .xml file named "556905US_041125_ST26.xml". The .xml file was generated on Apr. 11, 2025 and is 10,876 bytes in size. The entire contents of the Sequence Listing are hereby incorporated by reference.

TECHNICAL FIELD

The present disclosure relates to tertiary amide derivatives substituted with a quaternary carbon that are useful as medicines and pharmaceutically acceptable salts thereof, pharmaceutical compositions comprising the same, therapeutic agents and/or prophylactic agents for conditions in which CBP/P300 is involved, comprising the composition, and the like.

BACKGROUND ART

A chromosome dynamically controls gene replication and transcription by changing its higher order structure through methylation modification of its structural element DNA, and various modifications (such as acetylation, methylation, phosphorylation and ubiquitination) of histone (including histone H2A, H2B, H3 and H4) (Non-Patent Literature 1).

Acetylation of histone is post-translational modification that can frequently occur in a eukaryote, and acts to promote gene transcription. Histone acetyltransferases (HATs), which function during the acetylation modification of histones, are enzymes that transfer acetyl groups to the lysine side chains of histones. They are broadly classified into four types based on amino acid sequence homology, higher-order structure, and function. They are CBP/P300 (E1A binding protein p300/CREB Binding Protein), GCN5/PCAF (general control nonrepressed-protein 5/P300/CBP-associated factor), MYST (MOZ, Ybf2/Sas3, Sas2, and Tip60), and Rtt109 (Regulator of Tyl Transposition gene production 109). P300 and its paralogue CBP have an amino acid sequence homology of 90% or more, and include, in addition to the HAT domain, CH1/CH2/CH3 domains (cysteine-histidine rich domains), KIX domain, bromo domain and the like (Non-Patent Literature 2).

CBP/P300 were each discovered as respective binding partners of E1A adenoviral protein and cAMP-regulated enhancer binding protein (Non-Patent Literatures 3 to 5). Thereafter, it was found that CBP/P300 have HAT activity (Non-Patent Literatures 6 and 7), and their substrate specificity was also scrutinized, and as a result, it was reported that they acetylate not only a lysine residue of histone (H2A, H2B, H3 and H4) but also p53 (Non-Patent Literature 8), MyoD (Non-Patent Literature 9), STAT3 (Non-Patent Literature 10), Androgen receptor (Non-Patent Literature 11) and the like. Besides, CBP/P300 are also involved in a large number of biological reactions such as division, proliferation and differentiation (Non-Patent Literature 12).

It has been reported that CBP/P300 plays an important role in the proliferation of various cancers. Examples include prostate cancer (Non-Patent Literatures 13 and 14), liver cancer (Non-Patent Literatures 15 and 16), lung cancer (Non-Patent Literatures 17 to 19), breast cancer (Non-Patent Literature 20), colon cancer and gastric cancer (Non-Patent Literature 21), blood cancer (Non-Patent Literatures 22 and 23), pancreatic cancer (Non-Patent Literature 24), bladder cancer (Non-Patent Literature 25), gastrointestinal stromal tumor (Non-Patent Literature 26), NUT midline carcinoma (Non-Patent Literature 27), ovarian cancer (Non-Patent Literature 28), malignant rhabdoid tumor and epithelioid sarcoma (Patent Literature 11).

From the above, drugs that inhibit the function of CBP/P300 are expected to be useful as antitumor agents. To date, small molecule inhibitors targeting the HAT domain of CBP/P300 have been disclosed in Patent Literatures 1 to 10 and Non-Patent Literature 29.

CITATION LIST

Patent Literature

[PTL 1]
WO 2016/044770
[PTL 2]
WO 2018/235966
[PTL 3]
WO 2019/111980
[PTL 4]
WO 2019/049061
[PTL 5]
WO 2019/161157
[PTL 6]
WO 2019/161162
[PTL 7]
WO 2020/176558
[PTL 8]
WO 2019/201291
[PTL 9]
WO 2020/108500
[PTL 10]
WO 2020/198567
[PTL 11]
WO 2022/138944

Non-Patent Literature

[NPL 1]
Genes Dev. 2002, 16(14):1739-1742.
[NPL 2]
Mol Genet Metab. 2016,119(1-2):37-43.
[NPL 3]
Virology. 1985,147(1):142-153.
[NPL 4]
Mol Cell Biol. 1986, 6(5):1579-1589.
[NPL 5]
Nature. 1993,365(6449):855-859.
[NPL 6]
Cell. 1996, 87(5):953-959.
[NPL 7]
Nature. 1996,384(6610):641-643.

[NPL 8]
Cell. 1997, 90(4):595-606.
[NPL 9]
J Biol Chem. 2000,275(44):34359-34364.
[NPL 10]
Science. 2005,307(5707):269-273.
[NPL 11]
J Biol Chem. 2000,275(27), 20853-20860.
[NPL 12]
J Cell Sci. 2001,114(Pt 13):2363-2373.
[NPL 13]
Adv Exp Med Biol. 2008; 617:535-540.
[NPL 14]
Prostate. 2008, 68 (10):1097-1104.
[NPL 15]
Cancer Lett. 2011,310(2):140-147.
[NPL 16]
J Transl Med. 2011, 9:5.
[NPL 17]
Int J Clin Exp Pathol. 2014, 7(2):760-767.
[NPL 18]
Nat Genet. 2012, 44(10):1104-1110.
[NPL 19]
Clin Cancer Res. 2005, 11(2 Pt 1):512-519.
[NPL 20]
Genes Cancer. 2016, 7(3-4):98-109.
[NPL 21]
Oncogene. 1996, 12(7):1565-1569.
[NPL 22]
Proc Natl Acad Sci USA. 1997, 94(16):8732-8737.
[NPL 23]
Blood. 2012,120(15)3058-3068.
[NPL 24]
Nat Genet. 2000, 24(3):300-303.
[NPL 25]
Nat Genet. 2011, 43(9):875-878.
[NPL 26]
Oncol Rep. 2016, 36(5):2763-2770.
[NPL 27]
J Biol Chem. 2015,290(5):2744-2758.
[NPL 28]
Oncotarget. 2016, 7(14):17790-17804.
[NPL 29]
Bioorg Med Chem Lett. 2021, 39:127854-127859.

SUMMARY OF THE INVENTION

Solution to Problem

The present disclosure provides a compound that exerts an anticancer effect by inhibiting CBP/P300, which has been reported to be highly expressed, mutated, or hyperactive in various cancers. Preferably, the present disclosure provides a compound that has high CBP/P300 inhibitory activity, as well as "high water solubility enough to exert an anticancer effect when administered intravenously" and "high oral absorbability enough to exert an anticancer effect when administered orally." In other words, the present disclosure provides a compound that is extremely useful as an anti-cancer agent that can be expected to be applied to the treatment of a wide range of cancer types.

As a result of intensive studies, the present inventors have found that a compound represented by the following Formula (1) or a pharmaceutically acceptable salt thereof (hereinafter, also referred to as "the compound of the present disclosure") has a strong inhibitory action on the HAT domain of CBP/P300 and thereby exhibits an excellent anticancer effect, and exhibits high oral absorbability and high water solubility suitable for oral administration and intravenous administration, thereby completing the present disclosure.

Accordingly, the present disclosure is as follows.

[Item 1]

A compound represented by the following Formula (1)

[Chemical Formula 1]

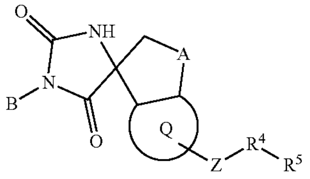

(1)

wherein

A represents CHF, or $CH_2$,

B represents the following Formula (B-1):

[Chemical Formula 2]

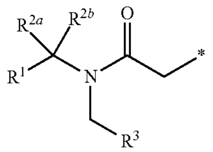

(B-1)

wherein * indicates the binding position to the nitrogen atom on the hydantoin ring, Ring Q represents an optionally substituted 6- to 10-membered aromatic hydrocarbon ring, or an optionally substituted 5- to 10-membered aromatic heterocycle, Z represents —O—, —N($R^{7a}$)—, an optionally substituted 6- to 10-membered divalent aromatic ring group, an optionally substituted 5- to 10-membered divalent aromatic heterocyclic group, or an optionally substituted 4- to 10-membered divalent non-aryl heterocyclic group, $R^1$ represents optionally substituted $C_{1-6}$ alkyl, or an optionally substituted $C_{3-10}$ alicyclic group, $R^{2a}$ and $R^{2b}$ each independently represent optionally substituted $C_{1-6}$ alkyl, wherein $R^{2a}$ and $R^{2b}$, together with the carbon atom to which they are attached, may form optionally substituted $C_{3-6}$ cycloalkylene, or an optionally substituted 4- to 6-membered divalent non-aryl heterocyclic group, $R^3$ represents optionally substituted $C_{6-10}$ aryl, optionally substituted 5- to 10-membered heteroaryl, an optionally substituted $C_{3-10}$ alicyclic group, or an optionally substituted 4- to 10-membered non-aryl heterocyclic group, $R^4$ represents a single bond, optionally substituted $C_{1-6}$ alkylene, optionally substituted $C_{3-10}$ cycloalkylene, or an optionally substituted 4- to 10-membered divalent non-aryl heterocyclic group, $R^5$ represents a hydrogen atom, a halogen atom, a hydroxyl group, cyano, optionally substituted $C_{1-6}$ alkyl, optionally substituted $C_{1-6}$ alkenyl, optionally substituted $C_{1-6}$ alkynyl, optionally substituted $C_{1-3}$ alkoxy, —$NR^{7b}R^{7c}$, —$SO_2R^{7d}$, —$CONR^{7e}R^{7f}$, an optionally substituted $C_{3-10}$ alicyclic group, an optionally substituted 4- to 10-membered non-aryl heterocyclic group, optionally substituted $C_{6-10}$ aryl, or optionally substituted 5- to 10-membered heteroaryl, and $R^{7a}$, $R^{7b}$, $R^{7c}$, $R^{7d}$, $R^{7e}$, and $R^{7f}$ each independently represent a hydrogen atom, or optionally substituted $C_{1-6}$ alkyl, or a pharmaceutically acceptable salt thereof.

[Item 2]

The compound or the pharmaceutically acceptable salt thereof of item 1, wherein the optionally substituted 6- to 10-membered aromatic hydrocarbon ring, the optionally substituted 5- to 10-membered aromatic heterocycle, the optionally substituted 6- to 10-membered divalent aromatic hydrocarbon ring group, the optionally substituted 5- to 10-membered divalent aromatic heterocyclic group, the optionally substituted $C_{6-10}$ aryl, the optionally substituted 5- to 10-membered heteroaryl, the optionally substituted 4- to 10-membered non-aryl heterocyclic group, the optionally substituted $C_{1-6}$ alkyl, the optionally substituted $C_{1-6}$ alkenyl, the optionally substituted $C_{1-6}$ alkynyl, the optionally substituted $C_{3-10}$ alicyclic group, the optionally substituted $C_{3-6}$ cycloalkylene, the optionally substituted 4- to 6-membered divalent non-aryl heterocyclic group, the optionally substituted $C_{1-6}$ alkylene, the optionally substituted $C_{3-10}$ cycloalkylene, the optionally substituted 4- to 10-membered divalent non-aryl heterocyclic group, or the optionally substituted $C_{1-3}$ alkoxy in $R^1$, $R^{2a}$, $R^{2b}$, $R^3$, $R^4$, $R^5$, $R^{7a}$, $R^{7b}$, $R^{7c}$, $R^{7d}$, $R^{7e}$, $R^{7f}$, $R^8$, $R^{9a}$, $R^{9b}$, Rings Q and Z are each independently optionally substituted with 1 to 5 of the same or different substituents selected from the group consisting of (1) a halogen atom,
(2) a hydroxyl group,
(3) $C_{6-10}$ aryl,
(4) 5- to 12-membered heteroaryl,
(5) $C_{1-6}$ alkyl,
(6) $C_{2-6}$ alkenyl,
(7) $C_{2-6}$ alkynyl,
(8) $C_{1-6}$ alkoxy,
(9) $C_{1-6}$ alkylthio
(10) a $C_{3-10}$ alicyclic group,
(11) a 3- to 10-membered non-aryl heterocyclic group,
(12) carboxyl,
(13) —$COR^{10}$,
(14) —$CO_2R^{10}$,
(15) —$CONR^{11}R^{12}$,
(16) —$NR^{11}R^{12}$,
(17) —$NR^{13}COR^{10}$,
(18) —$NR^{13}CO_2R^{10}$,
(19) —$NR^{13}SO_2R^{10}$,
(20) —$NR^{13}CONR^{11}R^{12}$,
(21) —$NR^{13}SO_2NR^{11}R^{12}$,
(22) —$SO_2R^{10}$,
(23) —$SO_2NR^{11}R^{12}$,
(24) —$OCOR^{10}$,
(25) —$OCO_2R^{10}$,
(26) —$OCONR^{11}R^{12}$,
(27) sulfo,
(28) a phosphoric acid group,
(29) cyano, and
(30) nitro, wherein the groups represented by the (3) $C_{6-10}$ aryl, (4) 5- to 12-membered heteroaryl, (5) $C_{1-6}$ alkyl, (6) $C_{2-6}$ alkenyl, (7) $C_{2-6}$ alkynyl, (8) $C_{1-6}$ alkoxy, (9) $C_{1-6}$ alkylthio, (10) a $C_{3-10}$ alicyclic group and (11) a 3- to 10-membered non-aryl heterocyclic group are optionally substituted with 1 to 5 of the same or different substituents selected from the group consisting of (a) a halogen atom,
(b) a hydroxyl group,
(c) $C_{6-10}$ aryl,
(d) 5- to 12-membered heteroaryl,
(e) $C_{1-6}$ alkyl,
(f) $C_{2-6}$ alkenyl,
(g) $C_{2-6}$ alkynyl,
(h) $C_{1-6}$ alkoxy,
(i) a $C_{3-10}$ alicyclic group,
(j) a 3- to 10-membered non-aryl heterocyclic group,
(k) carboxyl,
(l) —$COR^{10}$,
(m) —$CO_2R^{10}$,
(n) —$CONR^{11}R^{12}$,
(o) —$NR^{11}R^{12}$,
(p) —$NR^{13}COR^{10}$,
(q) —$NR^{13}SO_2R^{10}$,
(r) —$SO_2R^{10}$,
(s) —$SO_2NR^{11}R^{12}$,
(t) sulfo,
(u) a phosphoric acid group,
(v) cyano, and
(w) nitro, $R^{10}$, if there are multiple instances, are each independently $C_{1-6}$ alkyl, $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group, and $R^{13}$ is a hydrogen atom or $C_{1-6}$ alkyl.

[Item 3]

The compound or the pharmaceutically acceptable salt thereof of item 1 or 2, wherein the optionally substituted 6- to 10-membered aromatic hydrocarbon ring, the optionally substituted 5- to 10-membered aromatic heterocycle, the optionally substituted 6- to 10-membered divalent aromatic hydrocarbon ring group, the optionally substituted 5- to 10-membered divalent aromatic heterocyclic group, the optionally substituted $C_{6-10}$ aryl, the optionally substituted 5- to 10-membered heteroaryl, the optionally substituted 4- to 10-membered non-aryl heterocyclic group, the optionally substituted $C_{1-6}$ alkyl, the optionally substituted $C_{1-6}$ alkenyl, optionally substituted $C_{1-6}$ alkynyl, the optionally substituted $C_{3-10}$ alicyclic group, the optionally substituted $C_{3-6}$ cycloalkylene, the optionally substituted 4- to 6-membered divalent non-aryl heterocyclic group, the optionally substituted $C_{1-6}$ alkylene, the optionally substituted $C_{3-10}$ cycloalkylene, the optionally substituted 4- to 10-membered divalent non-aryl heterocyclic group, or the optionally substituted $C_{1-3}$ alkoxy in $R^1$, $R^{2a}$, $R^{2b}$, $R^3$, $R^4$, $R^5$, $R^{7a}$, $R^{7b}$, $R^{7c}$, $R^{7d}$, $R^{7e}$, $R^{7f}$, $R^8$, $R^{9a}$, $R^{9b}$, Rings Q and Z are each independently optionally substituted with 1 to 5 of the same or different substituents selected from the group consisting of (1) a halogen atom,
(2) a hydroxyl group,
(3) $C_{6-10}$ aryl,
(4) 5- to 12-membered heteroaryl,
(5) $C_{1-6}$ alkyl optionally substituted with 1 to 3 halogen atoms,
(6) $C_{2-6}$ alkenyl, (7) $C_{2-6}$ alkynyl,
(8) $C_{1-6}$ alkoxy,
(9) a $C_{3-10}$ alicyclic group,
(10) a 3- to 10-membered non-aryl heterocyclic group,
(11) carboxyl,
(12) —$COR^{10}$,
(13) —$CO_2R^{10}$,
(14) —$CONR^{11}R^{12}$,
(15) —$NR^{11}R^{12}$,
(16) —$SO_2R^{10}$,
(17) —$SO_2NR^{11}R^{12}$,
(18) sulfo,
(19) a phosphoric acid group,
(20) cyano, and
(21) nitro, $R^{10}$, if there are multiple instances, are each independently $C_{1-6}$ alkyl, and $R^{11}$ and $R^{12}$ each independently represent a hydrogen atom or $C_{1-6}$ alkyl, and if there are multiple instances of $R^{11}$ or $R^{12}$ each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 4]

The compound or the pharmaceutically acceptable salt thereof of any one of items 1 to 3, wherein the optionally substituted 6- to 10-membered aromatic hydrocarbon ring, the optionally substituted 5- to 10-membered aromatic heterocycle, the optionally substituted 6- to 10-membered divalent aromatic hydrocarbon ring group, the optionally substituted 5- to 10-membered divalent aromatic heterocyclic group, the optionally substituted $C_{6-10}$ aryl, the optionally substituted 5- to 10-membered heteroaryl, the optionally substituted 4- to 10-membered non-aryl heterocyclic group, the optionally substituted $C_{1-6}$ alkyl, the optionally substituted $C_{1-6}$ alkenyl, the optionally substituted $C_{1-6}$ alkynyl, the optionally substituted $C_{3-10}$ alicyclic group, the optionally substituted $C_{3-6}$ cycloalkylene, the optionally substituted 4- to 6-membered divalent non-aryl heterocyclic group, the optionally substituted $C_{1-6}$ alkylene, the optionally substituted $C_{3-10}$ cycloalkylene, the optionally substituted 4- to 10-membered divalent non-aryl heterocyclic group, or the optionally substituted $C_{1-3}$ alkoxy in $R^1$, $R^{2a}$, $R^{2b}$, $R^3$, $R^4$, $R^5$, $R^{7a}$, $R^{7b}$, $R^{7c}$, $R^{7d}$, $R^{7e}$, $R^{7f}$, $R^8$, $R^{9a}$, $R^{9b}$, Rings Q and Z are each independently optionally substituted with 1 to 5 of the same or different substituents selected from the group consisting of (1) a halogen atom,
(2) a hydroxyl group,
(3) phenyl,
(4) 5- to 6-membered heteroaryl,
(5) $C_{1-6}$ alkyl optionally substituted with 1 to 3 halogen atoms,
(6) $C_{1-6}$ alkoxy,
(7) a $C_{3-7}$ alicyclic group,
(8) a 3- to 7-membered non-aryl heterocyclic group,
(9) —$COR^{10}$,
(10) —$CO_2R^{10}$,
(11) —$CONR^{11}R^{12}$,
(12) —$NR^{11}R^{12}$,
(13) —$SO_2R^{10}$,
(14) —$SO_2NR^{11}R^{12}$, and
(15) cyano, $R^{10}$, if there are multiple instances, are each independently $C_{1-6}$ alkyl, and $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 5]

The compound or the pharmaceutically acceptable salt thereof of any one of items 1 to 4, wherein B is the following Formula (B-2), (B-3), or (B-4):

[Chemical Formula 3]

(B-2)

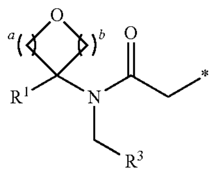

(B-3)

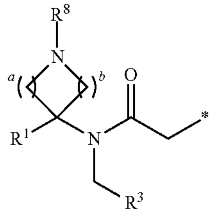

(B-4)

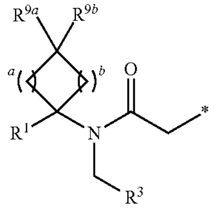

wherein * indicates the binding position to the nitrogen atom on the hydantoin ring, a represents 0, 1, or 2, b represents 1, or 2, $R^8$ represents a hydrogen atom, or optionally substituted $C_{1-6}$ alkyl, and $R^{9a}$ and $R^{9b}$ each independently represent a hydrogen atom, a halogen atom, or optionally substituted $C_{1-6}$ alkyl.

[Item 6]

The compound or the pharmaceutically acceptable salt thereof of any one of items 1 to 5, wherein $R^1$ is $C_{1-3}$ alkyl so optionally substituted with 1 to 3 fluorine atoms.

[Item 7]

The compound or the pharmaceutically acceptable salt thereof of any one of items 1 to 6, wherein $R^1$ is $CF_3$.

[Item 8]

The compound or the pharmaceutically acceptable salt thereof of any one of items 1 to 7, wherein $R^3$ is $C_{6-10}$ aryl (the aryl is optionally substituted with 1 to 3 of the same or different substituents selected from the group consisting of a halogen atom and optionally substituted $C_{1-6}$ alkyl), or 5- to 10-membered heteroaryl (the heteroaryl is optionally substituted with 1 to 3 of the same or different substituents selected from the group consisting of a halogen atom and $C_{1-6}$ alkyl).

[Item 9]

The compound or the pharmaceutically acceptable salt thereof of any one of items 1 to 8, wherein $R^3$ is 4-fluorophenyl, 4-(trifluoromethyl)phenyl, or 4-fluoro-2-pyridyl.

[Item 10]

The compound or the pharmaceutically acceptable salt thereof of any one of items 1 to 9, wherein $R^3$ is 4-fluorophenyl, or 4-fluoro-2-pyridyl.

[Item 11]

The compound or the pharmaceutically acceptable salt thereof of any one of items 1 to 10, wherein Ring Q is a 6- to 10-membered aromatic hydrocarbon ring (the aromatic hydrocarbon ring is optionally substituted with 1 to 3 of the same or different substituents selected from the group consisting of a halogen atom and $C_{1-6}$ alkyl).

[Item 12]

The compound or the pharmaceutically acceptable salt thereof of any one of items 1 to 11, wherein Ring Q is a benzene ring (the benzene ring is optionally substituted with 1 to 3 of the same or different substituents selected from the group consisting of a halogen atom and $C_{1-6}$ alkyl).

[Item 13]

The compound or the pharmaceutically acceptable salt thereof of any one of items 1 to 12, wherein a is 1, or 2.

[Item 14]

The compound or the pharmaceutically acceptable salt thereof of any one of items 1 to 13, wherein a is 1.

[Item 15]

The compound or the pharmaceutically acceptable salt thereof of any one of items 1 to 14, wherein b is 1.

[Item 16]

The compound or the pharmaceutically acceptable salt thereof of any one of items 1 to 15, wherein a is 1, and b is 1.

[Item 17]

The compound or the pharmaceutically acceptable salt thereof of item 1, wherein Formula (1) is the following Formula (2):

[Chemical Formula 4]

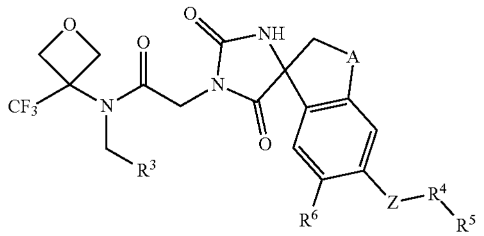

(2)

wherein

A represents CHF, or $CH_2$, $R^3$ represents 4-fluorophenyl, or 4-fluoro-2-pyridyl, Z represents

—O—, a 6- to 10-membered divalent aromatic ring group (the divalent aromatic ring group is optionally substituted with 1 to 3 of the same or different substituents selected from the group consisting of a halogen atom, $C_{1-6}$ alkyl and $—NR^{11}R^{12}$), a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and $—NR^{11}R^{12}$), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $—NR^{11}R^{12}$), $R^4$ represents a single bond, $C_{1-6}$ alkylene (the alkylene is optionally substituted with 1 to 3 of the same or different substituents selected from the group consisting of a halogen atom and $C_{1-6}$ alkyl), $C_{3-10}$ cycloalkylene (the cycloalkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $—NR^{11}R^{12}$), $R^5$ represents a hydrogen atom, a halogen atom, a hydroxyl group, cyano, $—NR^{7b}R^{7c}$, $—SO_2R^{7d}$, $—CONR^{7e}R^{7f}$, $C_{1-6}$ alkyl (the alkyl is optionally substituted with 1 to 3 of the same or different substituents selected from the group consisting of a halogen atom, $C_{1-6}$ alkyl, a hydroxyl group and $—NR^{11}R^{12}$), $C_{1-6}$ alkenyl (the alkenyl is optionally substituted with 1 to 3 of the same or different substituents selected from the group consisting of a halogen atom, $C_{1-6}$ alkyl, a hydroxyl group and $—NR^{11}R^{12}$), $C_{1-6}$ alkynyl (the alkynyl is optionally substituted with 1 to 3 of the same or different substituents selected from the group consisting of a halogen atom, $C_{1-6}$ alkyl, a hydroxyl group and $—NR^{11}R^{12}$), $C_{1-6}$ alkoxy (the alkoxy is optionally substituted with 1 to 3 of the same or different substituents selected from the group consisting of a halogen atom, $C_{1-6}$ alkyl and $—NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and $—NR^{11}R^{12}$), $C_{6-10}$ aryl (the aryl is optionally substituted with 1 to 3 of the same or different substituents selected from the group consisting of a halogen atom, $C_{1-6}$ alkyl and $—NR^{11}R^{12}$), 5- to 10-membered heteroaryl (the heteroaryl is optionally substituted with 1 to 3 of the same or different substituents selected from the group consisting of a halogen atom, $C_{1-6}$ alkyl and $—NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and $—NR^{11}R^{12}$), $R^6$ represents a hydrogen atom, or a halogen atom, $R^{7b}$, $R^{7c}$, $R^{7d}$, $R^{7e}$, and $R^{7f}$ each independently represent a hydrogen atom, or $C_{1-6}$ alkyl (the alkyl is optionally substituted with 1 to 3 of the same or different substituents selected from the group consisting of a halogen atom and $C_{1-6}$ alkyl), and $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 18]

The compound or the pharmaceutically acceptable salt thereof of item 17, wherein A is CHF.

[Item 19]

The compound or the pharmaceutically acceptable salt thereof of item 17 or 18, wherein $R^6$ is a hydrogen atom.

[Item 20]

The compound or the pharmaceutically acceptable salt thereof of any one of items 17 to 19, wherein Z is a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), or a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$).

[Item 21]

The compound or the pharmaceutically acceptable salt thereof of any one of items 17 to 20, wherein Z is a 5-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$).

[Item 22]

The compound or the pharmaceutically acceptable salt thereof of any one of items 17 to 21, wherein $R^4$ is a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$).

[Item 23]

The compound or the pharmaceutically acceptable salt thereof of any one of items 17 to 22, wherein $R^5$ is a hydrogen atom, a halogen atom, cyano, —$NR^{7b}R^{7c}$, $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), $C_{1-6}$ alkoxy (the alkoxy is optionally substituted with 1 to 3 of the same or different substituents selected from the group consisting of a halogen atom, $C_{1-6}$ alkyl and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$).

[Item 24]

The compound or the pharmaceutically acceptable salt thereof of item 1, wherein Formula (1) is the following Formula (3):

[Chemical Formula 5]

(3)

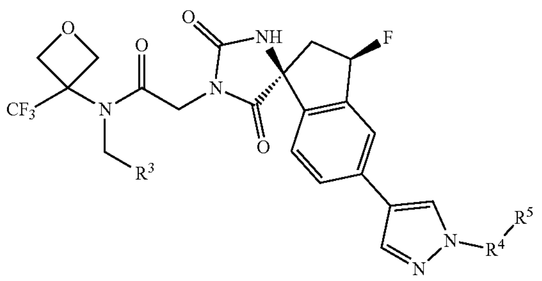

wherein $R^3$ represents 4-fluorophenyl, or 4-fluoro-2-pyridyl, $R^4$ represents a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), $R^5$ represents $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), and $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 25]

The compound or the pharmaceutically acceptable salt thereof of item 24, wherein $R^3$ is 4-fluorophenyl.

[Item 26]

The compound or the pharmaceutically acceptable salt thereof of item 24 or 25, wherein $R^3$ is 4-fluoro-2-pyridyl.

[Item 27]

The compound or the pharmaceutically acceptable salt thereof of any one of items 24 to 26, wherein $R^4$ is a 4- to 10-membered divalent non-aryl heterocyclic group.

[Item 28]

The compound or the pharmaceutically acceptable salt thereof of any one of items 24 to 27, wherein $R^4$ is a 4- to 6-membered divalent non-aryl heterocyclic group.

[Item 29]

The compound or the pharmaceutically acceptable salt thereof of any one of items 24 to 28, wherein $R^4$ is azetidinylene, or piperidinylene.

[Item 30]

The compound or the pharmaceutically acceptable salt thereof of any one of items 24 to 29, wherein $R^5$ is $C_{1-6}$ alkyl, or a 4- to 10-membered non-aryl heterocyclic group (the non-aryl heterocyclic group is optionally substituted with 1 to 3 of the same or different substituents selected from the group consisting of a halogen atom and $C_{1-6}$ alkyl).

[Item 31]

The compound or the pharmaceutically acceptable salt thereof of any one of items 24 to 30, wherein $R^5$ is $C_{1-3}$ alkyl, or a 4- to 6-membered non-aryl heterocyclic group (the non-aryl heterocyclic group is optionally substituted with 1 to 3 of the same or different substituents selected from the group consisting of a halogen atom and $C_{1-6}$ alkyl).

[Item 32]

The compound or the pharmaceutically acceptable salt thereof of any one of items 24 to 31, wherein $R^5$ is methyl.

[Item 33]

The compound or the pharmaceutically acceptable salt thereof of any one of items 24 to 31, wherein $R^5$ is oxetanyl.

[Item 34]

The compound or the pharmaceutically acceptable salt thereof of any one of items 24 to 33, wherein $R^{11}$ and $R^{12}$ are methyl groups.

[Item 35]

The compound or the pharmaceutically acceptable salt thereof of item 1, wherein Formula (1) is the following Formula (4):

[Chemical Formula 6]

(4)

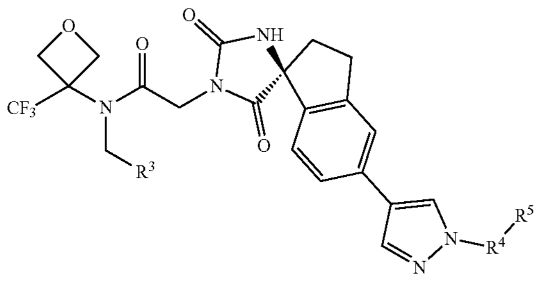

wherein $R^3$ represents 4-fluorophenyl, or 4-fluoro-2-pyridyl, $R^4$ represents a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), $R^5$ represents $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), and $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 36]

The compound or the pharmaceutically acceptable salt thereof of item 35, wherein $R^4$ is a 4- to 10-membered divalent non-aryl heterocyclic group.

[Item 37]

The compound or the pharmaceutically acceptable salt thereof of item 35 or 36, wherein $R^4$ is a 4- to 6-membered divalent non-aryl heterocyclic group.

[Item 38]

The compound or the pharmaceutically acceptable salt thereof of any one of items 35 to 37, wherein $R^4$ is azetidinylene.

[Item 39]

The compound or the pharmaceutically acceptable salt thereof of any one of items 35 to 38, wherein $R^5$ is $C_{1-6}$ alkyl, or a 4- to 10-membered non-aryl heterocyclic group (the non-aryl heterocyclic group is optionally substituted with 1 to 3 of the same or different substituents selected from the group consisting of a halogen atom and $C_{1-6}$ alkyl).

[Item 40]

The compound or the pharmaceutically acceptable salt thereof of any one of items 35 to 39, wherein $R^5$ is $C_{1-3}$ alkyl, or a 4- to 6-membered non-aryl heterocyclic group (the non-aryl heterocyclic group is optionally substituted with 1 to 3 of the same or different substituents selected from the group consisting of a halogen atom and $C_{1-6}$ alkyl).

[Item 41]

The compound or the pharmaceutically acceptable salt thereof of any one of items 35 to 40, wherein $R^5$ is oxetanyl.

[Item 42]

The compound or the pharmaceutically acceptable salt thereof of item 1, wherein Formula (1) is the following Formula (5)

[Chemical Formula 7]

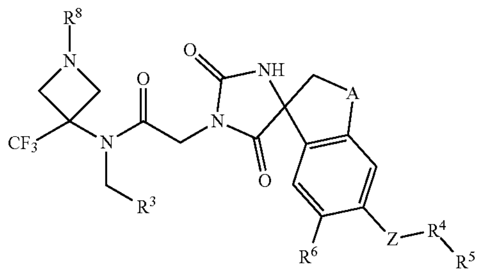

(5)

wherein

A represents CHF, or $CH_2$, $R^3$ represents 4-fluorophenyl, or 4-fluoro-2-pyridyl, Z represents a 6- to 10-membered divalent aromatic ring group (the divalent aromatic ring group is optionally substituted with 1 to 3 of the same or different substituents selected from the group consisting of a halogen atom, $C_{1-6}$ alkyl and —$NR^{11}R^{12}$), a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), $R^4$ represents a single bond, $C_{1-6}$ alkylene (the alkylene is optionally substituted with 1 to 3 of the same or different substituents selected from the group consisting of a halogen atom and $C_{1-6}$ alkyl), $C_{3-10}$ cycloalkylene (the cycloalkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), $R^5$ represents a hydrogen atom, a halogen atom, a hydroxyl group, cyano, —$NR^{7b}R^{7c}$, —$SO_2R^{7d}$, —$CONR^{7e}R^{7f}$, $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), $C_{1-6}$ alkenyl (the alkenyl is optionally substituted with 1 to 3 of the same or different substituents selected from the group consisting of a halogen atom, $C_{1-6}$ alkyl, a hydroxyl group and —$NR^{11}R^{12}$), $C_{1-6}$ alkynyl (the alkynyl is optionally substituted with 1 to 3 of the same or different substituents selected from the group consisting of a halogen atom, $C_{1-6}$ alkyl, a hydroxyl group and —$NR^{11}R^{12}$), $C_{1-3}$ alkoxy (the alkoxy is optionally substituted with 1 to 3 of the same or different substituents selected from the group consisting of a halogen atom, $C_{1-6}$ alkyl and —$NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and —$NR^{11}R^{12}$), $C_{6-10}$ aryl (the aryl is optionally substituted with 1 to 3 of the same or different substituents selected from the group consisting of a halogen atom, $C_{1-6}$ alkyl and —$NR^{11}R^{12}$), 5- to 10-membered heteroaryl (the heteroaryl is optionally substituted with 1 to 3 of the same or different substituents selected from the group consisting of a halogen atom, $C_{1-6}$ alkyl and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), $R^6$ represents a hydrogen atom, or a halogen atom, $R^{7b}$, $R^{7c}$, $R^{7d}$, $R^{7e}$, and $R^{7f}$ each independently represent a hydrogen atom, or $C_{1-6}$ alkyl (the alkyl is optionally substituted with 1 to 3 of the same or different substituents selected from the group consisting of a halogen atom and $C_{1-6}$ alkyl), $R^{10}$ represents a hydrogen atom, or $C_{1-6}$ alkyl (the alkyl is optionally substituted with 1 to 3 of the same or different substituents selected from the group consisting of a halogen atom and $C_{1-6}$ alkyl), and $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 43]

The compound or the pharmaceutically acceptable salt thereof of item 42, wherein A is CHF.

[Item 44]

The compound or the pharmaceutically acceptable salt thereof of item 42 or 43, wherein $R^6$ is a hydrogen atom.

[Item 45]

The compound or the pharmaceutically acceptable salt thereof of any one of items 42 to 44, wherein Z is a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), or a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and $—NR^{11}R^{12}$).

[Item 46]

The compound or the pharmaceutically acceptable salt thereof of any one of items 42 to 45, wherein Z is a 5-membered divalent aromatic heterocyclic group (the divalent aromatic heterocyclic group is optionally substituted with 1 to 3 of the same or different substituents selected from the group consisting of a halogen atom, $C_{1-6}$ alkyl and $—NR^{11}R^{12}$).

[Item 47]

The compound or the pharmaceutically acceptable salt thereof of any one of items 42 to 46, wherein $R^4$ is a single bond, $C_{1-6}$ alkylene (the alkylene is optionally substituted with 1 to 3 of the same or different substituents selected from the group consisting of a halogen atom and $C_{1-6}$ alkyl), or $C_{3-10}$ cycloalkylene (the cycloalkylene is optionally substituted with 1 to 3 of the same or different substituents selected from the group consisting of a halogen atom and $C_{1-6}$ alkyl).

[Item 48]

The compound or the pharmaceutically acceptable salt thereof of any one of items 42 to 47, wherein $R^5$ is a hydrogen atom, a hydroxyl group, cyano, $C_{1-6}$ alkyl (the alkyl is optionally substituted with 1 to 3 of the same or different substituents selected from the group consisting of a halogen atom, $C_{1-6}$ alkyl, a hydroxyl group and $—NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and $—NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and $—NR^{11}R^{12}$), and $R^{7d}$ is $C_{1-6}$ alkyl (the alkyl is optionally substituted with 1 to 3 of the same or different substituents selected from the group consisting of a halogen atom and $C_{1-6}$ alkyl).

[Item 49]

The compound or the pharmaceutically acceptable salt thereof of any one of items 42 to 48, wherein $R^{10}$ is $C_{1-6}$ alkyl.

[Item 50]

The compound or the pharmaceutically acceptable salt thereof of any one of items 42 to 49, wherein $R^8$ is a methyl group.

[Item 51]

The compound or the pharmaceutically acceptable salt thereof of item 1, wherein Formula (1) is the following Formula (6):

[Chemical Formula 8]

(6)

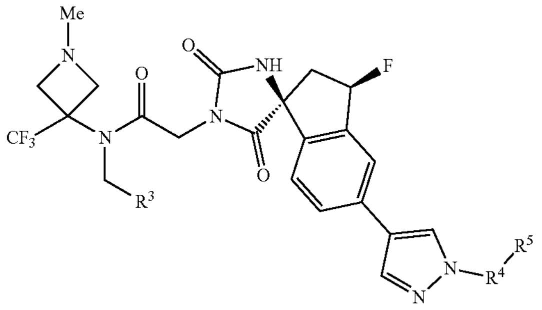

wherein $R^3$ represents 4-fluorophenyl, or 4-fluoro-2-pyridyl, $R^4$ represents a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $—NR^{11}R^{12}$), $R^5$ represents a hydrogen atom, a hydroxyl group, cyano, $C_{1-6}$ alkyl (the alkyl is optionally substituted with 1 to 3 of the same or different substituents selected from the group consisting of a halogen atom, $C_{1-6}$ alkyl, a hydroxyl group and $—NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and $—NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and $—NR^{11}R^{12}$), and $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 52]

The compound or the pharmaceutically acceptable salt thereof of item 51, wherein $R^3$ is 4-fluorophenyl.

[Item 53]

The compound or the pharmaceutically acceptable salt thereof of item 51 or 52, wherein $R^3$ is 4-fluoro-2-pyridyl.

[Item 54]

The compound or the pharmaceutically acceptable salt thereof of any one of items 51 to 53, wherein $R^4$ is a single bond, or $C_{1-6}$ alkylene (the alkylene is optionally substituted with 1 to 3 of the same or different substituents selected from the group consisting of a halogen atom and $C_{1-6}$ alkyl).

[Item 55]

The compound or the pharmaceutically acceptable salt thereof of any one of items 51 to 54, wherein $R^4$ is a single bond.

[Item 56]

The compound or the pharmaceutically acceptable salt thereof of any one of items 51 to 54, wherein $R^4$ is $C_{1-6}$ alkylene (the alkylene is optionally substituted with 1 to 3 of the same or different substituents selected from the group consisting of a halogen atom and $C_{1-6}$ alkyl).

[Item 57]

The compound or the pharmaceutically acceptable salt thereof of any one of items 51 to 56, wherein $R^5$ is a hydroxyl group, cyano, $C_{1-6}$ alkyl, a $C_{3-10}$ alicyclic group, or a 4- to 10-membered non-aryl heterocyclic group.

[Item 58]

The compound or the pharmaceutically acceptable salt thereof of any one of items 51 to 57, wherein $R^5$ is a methyl group.

[Item 59]

The compound or the pharmaceutically acceptable salt thereof of any one of items 51 to 57, wherein $R^5$ is oxetanyl.

[Item 60]

The compound or the pharmaceutically acceptable salt thereof of item 1, wherein Formula (1) is the following Formula (7):

[Chemical Formula 9]

(7)

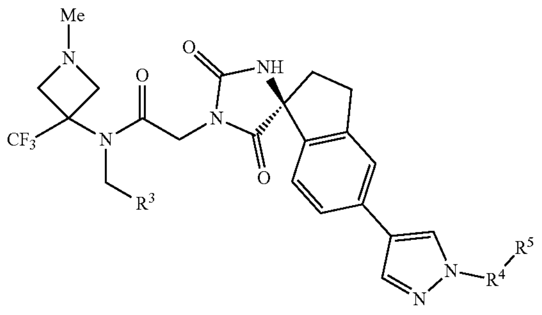

wherein $R^3$ represents 4-fluorophenyl, or 4-fluoro-2-pyridyl, $R^4$ represents a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $-NR^{11}R^{12}$), $R^5$ represents a hydrogen atom, cyano, $C_{1-6}$ alkyl (the alkyl is optionally substituted with 1 to 3 of the same or different substituents selected from the group consisting of a halogen atom, $C_{1-6}$ alkyl, a hydroxyl group and $-NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and $-NR^{11}R^{12}$), and $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 61]

The compound or the pharmaceutically acceptable salt thereof of item 60, wherein $R^4$ is a single bond, or $C_{1-6}$ alkylene (the alkylene is optionally substituted with 1 to 3 of the same or different substituents selected from the group consisting of a halogen atom and $C_{1-6}$ alkyl).

[Item 62]

The compound or the pharmaceutically acceptable salt thereof of item 60 or 61, wherein $R^4$ is a single bond.

[Item 63]

The compound or the pharmaceutically acceptable salt thereof of any one of items 60 to 62, wherein $R^4$ is $C_{1-6}$ alkylene (the alkylene is optionally substituted with 1 to 3 of the same or different substituents selected from the group consisting of a halogen atom and $C_{1-6}$ alkyl).

[Item 64]

The compound or the pharmaceutically acceptable salt thereof of any one of items 60 to 63, wherein $R^5$ is $C_{1-6}$ alkyl, or cyano.

[Item 65]

The compound or the pharmaceutically acceptable salt thereof of any one of items 60 to 64, wherein $R^5$ is a methyl group.

[Item 66]

The compound or the pharmaceutically acceptable salt thereof of any one of items 60 to 64, wherein $R^5$ is cyano.

[Item 67]

The compound or the pharmaceutically acceptable salt thereof of item 1, wherein Formula (1) is the following Formula (8):

[Chemical Formula 10]

(8)

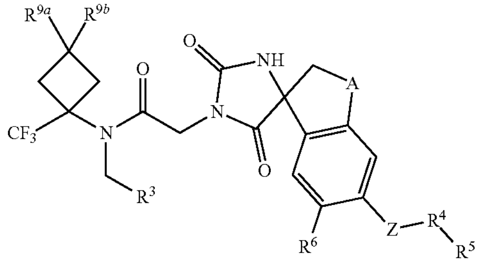

wherein

A represents CHF, or $CH_2$, $R^3$ represents 4-fluorophenyl, or 4-fluoro-2-pyridyl, Z represents a 6- to 10-membered divalent aromatic ring group (the divalent aromatic ring group is optionally substituted with 1 to 3 of the same or different substituents selected from the group consisting of a halogen atom, $C_{1-6}$ alkyl and —$NR^{11}R^{12}$), a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), $R^4$ represents a single bond, $C_{1-6}$ alkylene (the alkylene is optionally substituted with 1 to 3 of the same or different substituents selected from the group consisting of a halogen atom and $C_{1-6}$ alkyl), $C_{3-10}$ cycloalkylene (the cycloalkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), $R^5$ represents a hydrogen atom, a halogen atom, a hydroxyl group, cyano, —$NR^{7b}R^{7c}$, —$SO_2R^{7d}$, —$CONR^{7e}R^{7f}$, $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), $C_{1-6}$ alkenyl (the alkenyl is optionally substituted with 1 to 3 of the same or different substituents selected from the group consisting of a halogen atom, $C_{1-6}$ alkyl, a hydroxyl group and —$NR^{11}R^{12}$), $C_{1-6}$ alkynyl (the alkynyl is optionally substituted with 1 to 3 of the same or different substituents selected from the group consisting of a halogen atom, $C_{1-6}$ alkyl, a hydroxyl group and —$NR^{11}R^{12}$), $C_{1-3}$ alkoxy (the alkoxy is optionally substituted with 1 to 3 of the same or different substituents selected from the group consisting of a halogen atom, $C_{1-6}$ alkyl and —$NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and —$NR^{11}R^{12}$), $C_{6-10}$ aryl (the aryl is optionally substituted with 1 to 3 of the same or different substituents selected from the group consisting of a halogen atom, $C_{1-6}$ alkyl and —$NR^{11}R^{12}$), 5- to 10-membered heteroaryl (the heteroaryl is optionally substituted with 1 to 3 of the same or different substituents selected from the group consisting of a halogen atom, $C_{1-6}$ alkyl and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), $R^6$ represents a hydrogen atom, or a halogen atom, $R^{7b}$, $R^{7c}$, $R^{7d}$, $R^{7e}$, and $R^{7f}$ each independently represent a hydrogen atom, or $C_{1-6}$ alkyl (the alkyl is optionally substituted with 1 to 3 of the same or different substituents selected from the group consisting of a halogen atom and $C_{1-6}$ alkyl), $R^{9a}$ and $R^{9b}$ each independently represent a hydrogen atom, a halogen atom, or $C_{1-6}$ alkyl (the alkyl is optionally substituted with 1 to 3 of the same or different substituents selected from the group consisting of a halogen atom and $C_{1-6}$ alkyl), and $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 68]

The compound or the pharmaceutically acceptable salt thereof of item 67, wherein A is CHF.

[Item 69]

The compound or the pharmaceutically acceptable salt thereof of item 67 or 68, wherein $R^6$ is a hydrogen atom.

[Item 70]

The compound or the pharmaceutically acceptable salt thereof of any one of items 67 to 69, wherein Z is a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), or a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$).

[Item 71]

The compound or the pharmaceutically acceptable salt thereof of any one of items 67 to 70, wherein Z is a 5-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$).

[Item 72]

The compound or the pharmaceutically acceptable salt thereof of any one of items 67 to 71, wherein $R^4$ is a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$).

[Item 73]

The compound or the pharmaceutically acceptable salt thereof of any one of items 67 to 72, wherein $R^5$ is a hydrogen atom, cyano, —$NR^{7b}R^{7c}$, $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$).

[Item 74]

The compound or the pharmaceutically acceptable salt thereof of any one of items 67 to 73, wherein $R^{9a}$ and $R^{9b}$ are fluorine atoms.

[Item 75]

The compound or the pharmaceutically acceptable salt thereof of item 1, wherein Formula (1) is the following Formula (9):

[Chemical Formula 11]

(9)

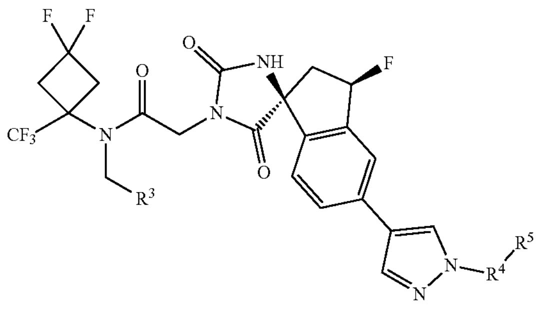

wherein $R^3$ represents 4-fluorophenyl, or 4-fluoro-2-pyridyl, $R^4$ represents a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), $R^5$ represents a hydrogen atom, cyano, $C_{1-6}$ alkyl, $C_{1-6}$ alkenyl, $C_{1-6}$ alkynyl, or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), and $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 76]

The compound or the pharmaceutically acceptable salt thereof of item 75, wherein $R^3$ is 4-fluorophenyl.

[Item 77]

The compound or the pharmaceutically acceptable salt thereof of item 75 or 76, wherein $R^3$ is 4-fluoro-2-pyridyl.

[Item 78]

The compound or the pharmaceutically acceptable salt thereof of any one of items 75 to 77, wherein $R^4$ is a 4- to 10-membered divalent non-aryl heterocyclic group.

[Item 79]

The compound or the pharmaceutically acceptable salt thereof of any one of items 75 to 78, wherein $R^4$ is a 4- to 6-membered divalent non-aryl heterocyclic group.

[Item 80]

The compound or the pharmaceutically acceptable salt thereof of any one of items 75 to 79, wherein $R^4$ is azetidinylene.

[Item 81]

The compound or the pharmaceutically acceptable salt thereof of any one of items 75 to 80, wherein $R^5$ is a 4- to 10-membered non-aryl heterocyclic group.

[Item 82]

The compound or the pharmaceutically acceptable salt thereof of any one of items 75 to 81, wherein $R^5$ is a 4- to 6-membered non-aryl heterocyclic group.

[Item 83]

The compound or the pharmaceutically acceptable salt thereof of any one of items 75 to 82, wherein $R^5$ is oxetanyl.

[Item 84]

The compound or the pharmaceutically acceptable salt thereof of item 1, wherein Formula (1) is the following Formula (10):

[Chemical Formula 12]

(10)

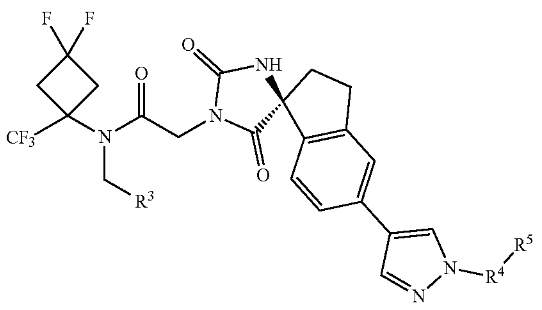

wherein $R^3$ represents 4-fluorophenyl, or 4-fluoro-2-pyridyl, $R^4$ represents a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the non-aryl heterocyclic group is optionally substituted with 1 to 3 of the same or different substituents selected from the group consisting of a halogen atom, $C_{1-6}$ alkyl and $—NR^{11}R^{12}$), $R^5$ represents a hydrogen atom, cyano, $C_{1-6}$ alkyl, $C_{1-6}$ alkenyl, $C_{1-6}$ alkynyl, or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and $—NR^{11}R^{12}$), and $R^{11}$ and $R^{12}$ each independently represent a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

[Item 85]

The compound or the pharmaceutically acceptable salt thereof of item 84, wherein $R^4$ is a 4- to 10-membered divalent non-aryl heterocyclic group.

[Item 86]

The compound or the pharmaceutically acceptable salt thereof of item 84 or 85, wherein $R^4$ is a 4- to 6-membered divalent non-aryl heterocyclic group.

[Item 87]

The compound or the pharmaceutically acceptable salt thereof of any one of items 84 to 86, wherein $R^4$ is azetidinylene.

[Item 88]

The compound or the pharmaceutically acceptable salt thereof of any one of items 84 to 87, wherein $R^5$ is a 4- to 10-membered non-aryl heterocyclic group.

[Item 89]

The compound or the pharmaceutically acceptable salt thereof of any one of items 84 to 88, wherein $R^5$ is a 4- to 6-membered non-aryl heterocyclic group.

[Item 90]

The compound or the pharmaceutically acceptable salt thereof of any one of items 84 to 89, wherein $R^5$ is oxetanyl.

[Item 91]

The compound or the pharmaceutically acceptable salt thereof of item 1, wherein the compound is selected from the following compounds:

N-[(4-fluorophenyl)methyl]-2-[(1'S)-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]-N-[3-(trifluoromethyl)oxetan-3-yl]acetamide (Example 1), 2-[(1'S)-5'-{1-[(3-fluoro-1-methylazetidin-3-yl)methyl]-1H-pyrazol-4-yl}-2,5-dioxo-2',3'-dihydrospiro[imidazolidine-4,1'-inden]-1-yl]-N-[(4-fluorophenyl)methyl]-N-[3-(trifluoromethyl)oxetan-3-yl]acetamide (Example 2), 2-[(1'S,3'R)-3'-fluoro-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]-N-[(4-fluorophenyl)methyl]-N-[3-(trifluoromethyl)oxetan-3-yl]acetamide (Example 3), N-[3,3-difluoro-1-(trifluoromethyl)cyclobutyl]-2-[(1'S,3'R)-3'-fluoro-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]-N-[(4-fluorophenyl)methyl]acetamide (Example 4), N-[3,3-difluoro-1-(trifluoromethyl)cyclobutyl]-N-[(4-fluorophenyl)methyl]-2-[(1'S)-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]acetamide (Example 5), N-[(5-fluoropyridin-2-yl)methyl]-2-[(1'S)-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]-N-[3-(trifluoromethyl)oxetan-3-yl]acetamide (Example 6), 2-[(1'S,3'R)-3'-fluoro-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]-N-[(5-fluoropyridin-2-yl)methyl]-N-[3-(trifluoromethyl)oxetan-3-yl]acetamide (Example 7), N-[3,3-difluoro-1-(trifluoromethyl)cyclobutyl]-N-[(5-fluoropyridin-2-yl)methyl]-2-[(1'S)-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]acetamide (Example 8), N-[3,3-difluoro-1-(trifluoromethyl)cyclobutyl]-2-[(1'S,3'R)-3'-fluoro-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]-N-[(5-fluoropyridin-2-yl)methyl]acetamide (Example 9), 2-[(1'S,3'R)-3'-fluoro-5'-(1-methyl-1H-pyrazol-4-yl)-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide (Example 10), 2-{(1'S,3'R)-5'-[1-(2-cyanopropan-2-yl)-1H-pyrazol-4-yl]-3'-fluoro-2,5-dioxo-2',3'-dihydrospiro[imidazolidine-4,1'-inden]-1-yl}-N-[(4-fluorophenyl)methyl]-N-[1-methyl-3-(trifluoromethyl)azetidin-3-yl]acetamide (Example 11), N-[(4-fluorophenyl)methyl]-2-[(1'S)-5'-(1-methyl-1H-pyrazol-4-yl)-2,5-dioxo-2',3'-dihydrospiro[imidazolidine-4,1'-inden]-1-yl]-N-[1-methyl-3-(trifluoromethyl)azetidin-3-yl]acetamide (Example 12), 2-{(1'S)-5'-[1-(2-cyanopropan-2-yl)-1H-pyrazol-4-yl]-2,5-dioxo-2',3'-dihydrospiro[imidazolidine-4,1'-inden]-1-yl}-N-[(4-fluorophenyl)methyl]-N-[1-methyl-3-(trifluoromethyl)azetidin-3-yl]acetamide (Example 13), 2-[(1'S, 3'R)-3'-fluoro-5'-(5-methyl-4,5,6,7-tetrahydropyrazolo[1,5-a]pyrazin-3-yl)-2,5-dioxo-2',3'-dihydrospiro[imidazolidine-4,1'-inden]-1-yl]-N-[(4-fluorophenyl)methyl]-N-[3-(trifluoromethyl)oxetan-3-yl]acetamide (Example 14), 2-[(1'S,3'R)-3'-fluoro-5'-(5-fluoro-1-methyl-1H-pyrazol-4-yl)-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide (Example 15), 2-[(1'S)-5'-(5-fluoro-1-methyl-1H-pyrazol-4-yl)-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide (Example 16), 2-[(1'S,3'R)-3'-fluoro-5'-(3-fluoro-1-methyl-1H-pyrazol-4-yl)-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide (Example 17), 2-[(1'S)-5'-(3-fluoro-1-methyl-1H-pyrazol-4-yl)-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide (Example 18), 2-{(1'S,3'R)-3'-fluoro-5'-[1-(oxan-4-yl)-1H-pyrazol-4-yl]-2,5-dioxo-2',3'-dihydrospiro[imidazolidine-4,1'-inden]-1-yl}-N-[(4-fluorophenyl)methyl]-N-[1-methyl-3-(trifluoromethyl)azetidin-3-yl]acetamide (Example 19), 2-[(1'S,3'R)-3'-fluoro-5'-(1-methyl-1H-pyrazol-4-yl)-2,5-dioxo-2',3'-dihydrospiro[imidazolidine-4,1'-inden]-1-yl]-N-[(5-fluoropyridin-2-yl)methyl]-N-[1-methyl-3-(trifluoromethyl)azetidin-3-yl]acetamide (Example 20), N-[(5-fluoropyridin-2-yl)methyl]-2-[(1'S)-5'-(1-methyl-1H-pyrazol-4-yl)-2,5-dioxo-2',3'-dihydrospiro[imidazolidine-4,1'-inden]-1-yl]-N-[1-methyl-3-(trifluoromethyl)azetidin-3-yl]acetamide (Example 21), 2-[(1'S,3'R)-5'-(1-{[3-(dimethylamino)oxetan-3-yl]methyl}-1H-pyrazol-4-yl)-3'-fluoro-2,5-dioxo-2',3'-dihydrospiro[imidazolidine-4,1'-inden]-1-yl]-N-[(4-fluorophenyl)methyl]-N-[3-(trifluoromethyl)oxetan-3-yl]acetamide (Example 22), 2-[(1'S,3'R)-3'-fluoro-5'-{1-[1-(oxetan-3-yl)piperidin-4-yl]-1H-pyrazol-4-yl}-2,5-dioxo-2',3'-dihydrospiro[imidazolidine-4,1'-inden]-1-yl]-N-[(5-fluoropyridin-2-yl)methyl]-N-[3-(trifluoromethyl)oxetan-3-yl]acetamide (Example 23), 2-{(1'S,3'R)-3'-fluoro-5'-[1-(oxetan-3-yl)-1H-pyrazol-4-yl]-2,5-dioxo-2',3'-dihydrospiro[imidazolidine-4,1'-inden]-1-yl}-N-[(5-fluoropyridin-2-yl)methyl]-N-[1-methyl-3-(trifluoromethyl)azetidin-3-yl]acetamide (Example 24), 2-[(1'S,3'R)-3'-fluoro-5'-{1-[(oxetan-3-yl)methyl]-1H-pyrazol-4-yl}-2,5-dioxo-2',3'-dihydrospiro[imidazolidine-4,1'-inden]-1-yl]-N-[(5-fluoropyridin-2-yl)methyl]-N-[1-methyl-3-(trifluoromethyl)azetidin-3-yl]acetamide (Example 25), 2-{(1'S,3'R)-5'-[1-(2-cyanopropan-2-yl)-1H-pyrazol-4-yl]-3'-fluoro-2,5-dioxo-2',3'-dihydrospiro[imidazolidine-4,1'-inden]-1-yl}-N-[(5-fluoropyridin-2-yl)methyl]-N-[1-methyl-3-(trifluoromethyl)azetidin-3-yl]acetamide (Example 26), 2-{(1'S,3'R)-3'-fluoro-5'-[1-(1-hydroxy-2-methylpropan-2-yl)-1H-pyrazol-4-yl]-2,5-dioxo-2',3'-dihydrospiro[imidazolidine-4,1'-inden]-1-yl}-N-[(5-fluoropyridin-2-yl)methyl]-N-[1-methyl-3-(trifluoromethyl)azetidin-3-yl]acetamide (Example 27), 2-[(1'R,3'S)-3',6'-difluoro-5'-(1-methyl-1H-pyrazol-4-yl)-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide (Example 28), 2-[(1'S,3'R)-3',6'-difluoro-5'-(1-methyl-1H-pyrazol-4-yl)-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide (Example 29), 2-[(1'S,3'R)-5'-(1-ethyl-1H-pyrazol-4-yl)-3'-fluoro-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide (Example 30), 2-{(1'S,3'R)-3'-fluoro-2,5-dioxo-5'-[1-(propan-2-yl)-1H-pyrazol-4-yl]-2',3'-dihydrospiro[imidazolidine-4,1'-inden]-1-yl}-N-[(4-fluorophenyl)methyl]-N-[1-methyl-3-(trifluoromethyl)azetidin-3-yl]acetamide (Example 31), 2-[(1'S,3'R)-5'-(1-ethyl-1H-pyrazol-4-yl)-3'-fluoro-2,5-dioxo-2',3'-dihydrospiro[imidazolidine-4,1'-inden]-1-yl]-N-[(5-fluoropyridin-2-yl)methyl]-N-[1-methyl-3-(trifluoromethyl)azetidin-3-yl]acetamide (Example 32), 2-{(1'S,3'R)-3'-fluoro-2,5-dioxo-5'-[1-(propan-2-yl)-1H-pyrazol-4-yl]-2',3'-dihydrospiro[imidazolidine-4,1'-inden]-1-yl}-N-[(5-fluoropyridin-2-yl)methyl]-N-[1-methyl-3-(trifluoromethyl)azetidin-3-yl]acetamide (Example 33), 2-[(1'S,3'R)-5'-(1-cyclobutyl-1H-pyrazol-4-yl)-3'-fluoro-2,5-dioxo-2',3'-dihydrospiro[imidazolidine-4,1'-inden]-1-yl]-N-[(5-fluoropyridin-2-yl)methyl]-N-[1-methyl-3-(trifluoromethyl)azetidin-3-yl]acetamide (Example 34), and 2-[(1'S,3'R)-3'-fluoro-5'-(1-methyl-1H-pyrazol-4-yl)-2,5-dioxo-2',3'-dihydrospiro[imidazolidine-4,1'-inden]-1-yl]-N-[1-methyl-3-(trifluoromethyl)azetidin-3-yl]-N-{[4-(trifluoromethyl)phenyl]methyl}acetamide (Example 35).

[Item 92]

The compound or the pharmaceutically acceptable salt thereof of item 1, wherein the compound is selected from the following compounds:

2-[(1'S,3'R)-3'-fluoro-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]-N-[(5-fluoropyridin-2-yl)methyl]-N-[3-(trifluoromethyl)oxetan-3-yl]acetamide (Example 7), 2-[(1'S,3'R)-3'-fluoro-5'-(1-methyl-1H-pyrazol-4-yl)-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide (Example 10), 2-[(1'S,3'R)-3'-fluoro-5'-(1-methyl-1H-pyrazol-4-yl)-2,5-dioxo-2',3'-dihydrospiro[imidazolidine-4,1'-inden]-1-yl]-N-[(5-fluoropyridin-2-yl)methyl]-N-[1-methyl-3-(trifluoromethyl)azetidin-3-yl]acetamide (Example 20), 2-[(1'S,3'R)-3'-fluoro-5'-{1-[1-(oxetan-3-yl)piperidin-4-yl]-1H-pyrazol-4-yl}-2,5-dioxo-2',3'-dihydrospiro[imidazolidine-4,1'-inden]-1-yl]-N-[(5-fluoropyridin-2-yl)methyl]-N-[3-(trifluoromethyl)oxetan-3-yl]acetamide (Example 23), 2-{(1'S,3'R)-3'-fluoro-5'-[1-(oxetan-3-yl)-1H-pyrazol-4-yl]-2,5-dioxo-2',3'-dihydrospiro[imidazolidine-4,1'-inden]-1-yl}-N-[(5-fluoropyridin-2-yl)methyl]-N-[1-methyl-3-(trifluoromethyl)azetidin-3-yl]acetamide (Example 24), 2-[(1'S,3'R)-3'-fluoro-5'-{1-[(oxetan-3-yl)methyl]-1H-pyrazol-4-yl}-2,5-dioxo-2',3'-dihydrospiro[imidazolidine-4,1'-inden]-1-yl]-N-[(5-fluoropyridin-2-yl)methyl]-N-[1-methyl-3-(trifluoromethyl)azetidin-3-yl]acetamide (Example 25), 2-[(1'S,3'R)-5'-(1-ethyl-1H-pyrazol-4-yl)-3'-fluoro-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide (Example 30), 2-{(1'S,3'R)-3'-fluoro-2,5-dioxo-5'-[1-(propan-2-yl)-1H-pyrazol-4-yl]-2',3'-dihydrospiro[imidazolidine-4,1'-inden]-1-yl}-N-[(4-fluorophenyl)methyl]-N-[1-methyl-3-(trifluoromethyl)azetidin-3-yl]acetamide (Example 31), 2-[(1'S,3'R)-5'-(1-ethyl-1H-pyrazol-4-yl)-3'-fluoro-2,5-dioxo-2',3'-dihydrospiro[imidazolidine-4,1'-inden]-1-yl]-N-[(5-fluoropyridin-2-yl)methyl]-N-[1-methyl-3-(trifluoromethyl)azetidin-3-yl]acetamide (Example 32), 2-{(1'S,3'R)-3'-fluoro-2,5-dioxo-5'-[1-(propan-2-yl)-1H-pyrazol-4-yl]-2',3'-dihydrospiro[imidazolidine-4,1'-inden]-1-yl}-N-[(5-fluoropyridin-2-yl)methyl]-N-[1-methyl-3-(trifluoromethyl)azetidin-3-yl]acetamide (Example 33), and 2-[(1'S,3'R)-5'-(1-cyclobutyl-1H-pyrazol-4-yl)-3'-fluoro-2,5-dioxo-2',3'-dihydrospiro[imidazolidine-4,1'-inden]-1-yl]-N-[(5-fluoropyridin-2-yl)methyl]-N-[1-methyl-3-(trifluoromethyl)azetidin-3-yl]acetamide (Example 34).

[Item 93]

A medicament comprising the compound or the pharmaceutically acceptable salt thereof of any one of items 1 to 92 as an active ingredient.

[Item 94]

A pharmaceutical composition comprising the compound or the pharmaceutically acceptable salt thereof of any one of items 1 to 92.

[Item 95]

A therapeutic agent and/or prophylactic agent for cancer, non-alcoholic fatty liver disease (NAFLD), acute liver disorder, cardiac disease, or metabolic disease, comprising the compound or the pharmaceutically acceptable salt thereof of any one of items 1 to 92 as an active ingredient.

[Item 96]

A therapeutic agent and/or prophylactic agent for cancer, comprising the compound or the pharmaceutically acceptable salt thereof of any one of items 1 to 92 as an active ingredient.

[Item 97]

The therapeutic agent and/or prophylactic agent of item 95 or 96, wherein the cancer is at least one type of cancer selected from the group consisting of SMARC deficient cancer, SS18-SSX fusion cancer and ARID deficient cancer.

[Item 98]

The therapeutic agent and/or prophylactic agent of any one of items 95 to 97, wherein the cancer is at least one type of cancer selected from the group consisting of malignant rhabdoid tumor, epithelioid sarcoma, atypical teratoid/rhabdoid tumor, nerve sheath tumor, chordoid meningioma, neuroepithelial tumor, glioneuronal tumor, craniopharyngioma, glioblastoma, chordoma, myoepithelial tumor, extraskeletal myxoid chondrosarcoma, synovial sarcoma, ossifying fibromyxoid tumor, basaloid squamous cell carcinoma of the paranasal sinus, esophageal cancer, papillary thyroid cancer, follicular thyroid cancer, gastrointestinal stromal tumor, pancreatic undifferentiated rhabdoid tumor, gastrointestinal rhabdoid tumor, renal medullary carcinoma, endometrial cancer, myoepithelioma-like tumor of the vulvar region, colon cancer, mesothelioma, pulmonary adenocarcinoma, large cell lung carcinoma, lung neuroendocrine tumor, gastroesophageal junction cancer, gastric cancer, bladder cancer, squamous cell lung cancer, pancreatic cancer, medulloblastoma, renal clear cell carcinoma, liver cancer, pleomorphic carcinoma, thoracic sarcoma, small cell carcinoma of the ovary, primary gallbladder tumor, uterine sarcoma, granulosa cell tumor of the ovary, adrenocortical carcinoma, small cell lung cancer, ovarian cancer, uterine cancer, neuroblastoma, mucinous ovarian tumor, nasal and paranasal sinus cancer, sarcoma in the thoracic cavity, bile duct cancer, neuroblastoma, melanoma, breast cancer, undifferentiated round cell sarcoma, rhabdomyosarcoma, and Ewing sarcoma.

[Item 99]

A method for treating and/or preventing cancer, non-alcoholic fatty liver disease (NAFLD), acute liver disorder, cardiac disease, or metabolic disease, comprising administering a therapeutically and/or prophylactically effective amount of the compound or the pharmaceutically acceptable salt thereof of any one of items 1 to 92, to a patient in need thereof.

[Item 100]

Use of the compound or the pharmaceutically acceptable salt thereof of any one of items 1 to 92, for the manufacture of a therapeutic agent and/or prophylactic agent for cancer, non-alcoholic fatty liver disease (NAFLD), acute liver disorder, cardiac disease, or metabolic disease.

[Item 101]

The compound or the pharmaceutically acceptable salt thereof of any one of items 1 to 92, for use in the treatment and/or prophylaxis of cancer, non-alcoholic fatty liver disease (NAFLD), acute liver disorder, cardiac disease, or metabolic disease.

[Item 102]

The compound or the pharmaceutically acceptable salt thereof of any one of items 1 to 92, for treating cancer in combination with an additional drug or a pharmaceutically acceptable salt thereof, wherein the additional drug is at least one selected from the group consisting of a hormonal therapy agent, a chemotherapeutic agent, an immunotherapeutic agent, and an agent inhibiting a cell growth factor and a receptor action thereof.

[Item 103]

A pharmaceutical composition comprising the compound or the pharmaceutically acceptable salt thereof of any one of items 1 to 92, comprised as a combination with an additional drug, wherein the additional drug is at least one selected from the group consisting of a hormonal therapy agent, a chemotherapeutic agent, an immunotherapeutic agent, and an agent inhibiting a cell growth factor and a receptor action thereof.

Effect of the Invention

The present disclosure provides CBP/P300 inhibitors, including tertiary amide derivatives substituted with a quaternary carbon and pharmaceutically acceptable salts thereof.

The present disclosure provides drugs that inhibit the function of CBP/P300, applicable to a wide range of diseases and administration methods. The present disclosure also provides compounds represented by Formula (1), which are tertiary amide derivatives substituted with a quaternary carbon and can be used as such drugs, and drugs related thereto.

The compounds of the present disclosure exhibit excellent CBP/P300 inhibitory activity and are useful as therapeutic agents for diseases in which CBP/P300 is involved, and are specifically applicable to patients with cancer, non-alcoholic fatty liver disease (NAFLD), acute liver disorder, cardiac disease, or metabolic disease and the like.

DESCRIPTION OF EMBODIMENTS

The present disclosure is described hereinafter in more detail. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present disclosure pertains. In case of a contradiction, the present specification (including the definitions) takes precedence.

The terms that are used herein are described hereinafter.

As used herein, the number of substituents in a group defined as "optionally substituted" is not particularly limited, as long as they are substitutable. When the number of substituents is specified and it is described as "substituted" with that number of substituents, it indicates that it is substituted with that number of substituents. For example, "substituted with 2 to 5 substituents" indicates that it is substituted with 2, 3, 4, or 5 substituents. The description of each group is also applicable when the group is a substituent or a part of another group, unless specifically noted otherwise.

"Halogen atom" includes a fluorine atom, a chlorine atom, a bromine atom, an iodine atom, and the like. The preferred is a fluorine atom or a chlorine atom.

"$C_{1-6}$ alkyl" refers to a linear or branched saturated hydrocarbon group with 1 to 6 carbon atoms, and "$C_6$ alkyl" refers to alkyl with 6 carbon atoms. The same applies to other numbers. $C_{1-6}$ alkyl is preferably "$C_{1-4}$ alkyl", and more preferably "$C_{1-3}$ alkyl". Specific examples of "$C_{1-3}$ alkyl" include methyl, ethyl, propyl, 1-methylethyl, and the like. Specific examples of "$C_{1-4}$ alkyl" include, in addition to the specific examples for the "$C_{1-3}$ alkyl" described above, butyl, 1,1-dimethylethyl, 1-methylpropyl, 2-methylpropyl, and the like. Specific examples of "$C_{1-6}$ alkyl" include, in addition to the specific examples for the "$C_{1-4}$ alkyl" described above, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, hexyl, and the like.

"$C_{2-6}$ alkenyl" refers to a linear or branched unsaturated hydrocarbon group with 2 to 6 carbon atoms, comprising 1 to 3 double bonds. "$C_{2-6}$ alkenyl" is preferably "$C_{2-4}$ alkenyl". Specific examples of "$C_{2-4}$ alkenyl" include vinyl, propenyl, methylpropenyl, butenyl, and the like. Specific examples of "$C_{2-6}$ alkenyl" include, in addition to the specific examples for the "$C_{2-4}$ alkenyl" described above, pentenyl, hexenyl, and the like.

"$C_{2-6}$ alkynyl" refers to a linear or branched unsaturated hydrocarbon group with 2 to 6 carbon atoms, comprising one triple bond. "$C_{2-6}$ alkynyl" is preferably "$C_{2-4}$ alkynyl". Specific examples of "$C_{2-4}$ alkynyl" include propynyl, methylpropynyl, butynyl, and the like. Specific examples of "$C_{2-6}$ alkynyl" include, in addition to the specific examples for the "$C_{2-4}$ alkynyl" described above, methylbutynyl, pentynyl, so hexynyl, and the like.

"$C_{1-6}$ alkoxy" is "$C_{1-6}$ alkyloxy", and the "$C_{1-6}$ alkyl" moiety is defined the same as the "$C_{1-6}$ alkyl". "$C_{1-6}$ alkoxy" is preferably "$C_{1-4}$ alkoxy", and more preferably "$C_{1-3}$ alkoxy". Specific examples of "$C_{1-3}$ alkoxy" include methoxy, ethoxy, propoxy, 1-methylethoxy, and the like. Specific examples of "$C_{1-4}$ alkoxy" include, in addition to the specific examples for the "$C_{1-3}$ alkoxy" described above, butoxy, 1,1-dimethylethoxy, 1-methylpropoxy, 2-methylpropoxy, and the like. Specific examples of "$C_{1-6}$ alkoxy" include, in addition to the specific examples for the "$C_{1-4}$ alkoxy" described above, pentyloxy, 1,1-dimethylpropoxy, 1,2-dimethylpropoxy, 1-methylbutoxy, 2-methylbutoxy, 4-methylpentyloxy, 3-methylpentyloxy, 2-methylpentyloxy, 1-methylpentyloxy, hexyloxy, and the like.

The "$C_{1-6}$ alkyl" moiety of "$C_{1-6}$ alkylthio" is defined by the same as the "$C_{1-6}$ alkyl". "$C_{1-6}$ alkylthio" is preferably "$C_{1-4}$ alkylthio", and more preferably "$C_{1-3}$ alkylthio". Specific examples of "$C_{1-3}$ alkylthio" include methylthio, ethylthio, propylthio, 1-methylethylthio, and the like. Specific examples of "$C_{1-4}$ alkylthio" include, in addition to the specific examples for the "$C_{1-3}$ alkylthio" described above, butylthio, 1,1-dimethylethylthio, 1-methylpropylthio, 2-methylpropylthio, and the like. Specific examples of "$C_{1-6}$ alkylthio" include, in addition to the specific examples for the "$C_{1-4}$ alkylthio" described above, pentylthio, 1,1-dimethylpropylthio, 1,2-dimethylpropylthio, 1-methylbutylthio, 2-methylbutylthio, 4-methylpentylthio, 3-methylpentylthio, 2-methylpentylthio, 1-methylpentylthio, hexylthio, and the like.

"$C_{1-6}$ alkylene" refers to a linear or branched divalent saturated hydrocarbon group with 1 to 6 carbon atoms. "$C_{1-6}$ alkylene" is preferably "$C_{1-4}$ alkylene", and more preferably "$C_{1-3}$ alkylene". Specific examples of "$C_{1-3}$ alkylene" include a methylene group, an ethylene group, a propylene group, and the like. Specific examples of "$C_{1-4}$ alkylene" include, in addition to the specific examples for the "$C_{1-3}$ alkylene" described above, a butylene group, a 1,1-dimethylethylene group, a 1,2-dimethylethylene group, a 1-methyltrimethylene group, a 2-methyltrimethylene group, and the like. Specific examples of "$C_{1-6}$ alkylene" include, in addition to the specific examples for the "$C_{1-4}$ alkylene" described above, a pentylene group, a 1,1-dimethyltrimethylene group, a 1,2-dimethyltrimethylene group, a 1-methylbutylene group, a 2-methylbutylene group, a 1-methylpentylene group, a 2-methylpentylene group, a 3-methylpentylene group, a hexylene group, and the like.

"$C_{2-6}$ alkenylene" refers to a linear or branched divalent unsaturated hydrocarbon group with 2 to 6 carbon atoms, containing 1 to 3 double bonds. "$C_{2-6}$ alkenylene" is preferably "$C_{2-4}$ alkenylene". Specific examples of "$C_{2-4}$ alkenylene" include a vinylene group, a vinylidene group, a propenylene group, a methylpropenylene group, a butenylene group and the like. Specific examples of "$C_{2-6}$ alkenyl" include, in addition to the specific examples for the "$C_{2-4}$ alkenyl" described above, a pentenylene group, a hexenylene group and the like.

"$C_{3-10}$ alicyclic group" refers to a cyclic saturated hydrocarbon group with 3 to 10 carbon atoms, including those with partially an unsaturated bond and those with a cross-linked structure. "$C_{3-10}$ alicyclic group" is preferably "$C_{3-7}$ alicyclic group". Specific examples of "$C_{3-7}$ alicyclic group" include cyclopropyl, cyclobutyl, cyclopentyl, cyclohexyl, cycloheptyl, and the like. Specific examples of "$C_{3-10}$ alicyclic group" include, in addition to the specific examples for the "$C_3$-7 alicyclic group" described above, cyclooctyl, cyclononyl, cyclodecyl, adamantyl, and the like.

"$C_{3-10}$ alicyclic group" also encompasses those with a bicyclic structure in which the $C_{3-10}$ alicyclic group described above is fused with an aromatic hydrocarbon ring. Specific examples of such a fused compound include the structures represented by the following formulas, and the like.

[Chemical Formula 13]

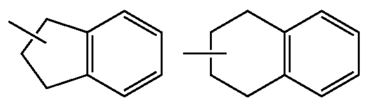

Specific examples of the crosslinked structure described above include the structures represented by the following formulas, and the like.

[Chemical Formula 14]

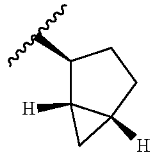

"$C_{3-10}$ cycloalkylene" refers to a cyclic divalent saturated hydrocarbon group with 3 to 10 carbon atoms, including those with partially an unsaturated bond and those with a crosslinked structure. "$C_3$-10 cycloalkylene" is preferably "$C_3$-7 cycloalkylene". Specific examples of "$C_3$-7 cycloalkylene" include cyclopropylene, cyclobutylene, cyclopentylene, cyclohexylene, cycloheptylene, and the like. Specific examples of "$C_3$-10 cycloalkylene" include, in addition to the specific examples for the "$C_3$-7 cycloalkylene" described above, cyclooctylene, cyclononylene, cyclodecylene, adamantylene, and the like.

Specific examples of the crosslinked structure described above include the structures represented by the following formulas, and the like.

[Chemical Formula 15]

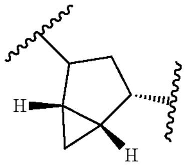

"$C_{3-10}$ cycloalkenylene" refers to a cyclic divalent unsaturated hydrocarbon group with 3 to 10 carbon atoms, including those with a crosslinked structure. Specific examples of "$C_{3-10}$ cycloalkenylene" include cyclobutenylene, cyclopentenylene, cyclohexenylene and the like.

"3- to 10-membered saturated carbocyclic ring" refers to a cyclic saturated hydrocarbon with 3 to 10 carbon atoms. "3- to 10-membered saturated carbocyclic ring" is preferably "4- to 6-membered saturated carbocyclic ring". Specific examples of "4- to 6-membered saturated carbocyclic ring" include a cyclobutane ring, a cyclopentane ring, a cyclohexane ring, and the like. Specific examples of "3- to 10-membered saturated carbocyclic ring" include, in addition to the specific examples for the "4- to 6-membered saturated carbocyclic ring" described above, a cyclopropane ring, a cycloheptane ring, cyclooctane, cyclononane, cyclodecane, and the like.

"4- to 10-membered non-aryl heterocyclic group" refers to a monovalent non-aryl heterocyclic group comprised of 1 to 2 atoms independently selected from the group consisting of a nitrogen atom, an oxygen atom and a sulfur atom, and 2 to 9 carbon atoms, including those with partially an unsaturated bond and those with a crosslinked structure. Ring-constituting atoms may include oxidized atoms such as —C(O)—, —S(O)—, or —$SO_2$—. "4- to 10-membered non-aryl heterocyclic group" is preferably "4- to 6-membered non-aryl heterocyclic group". Specific examples of "4- to 6-membered non-aryl heterocyclic group" include oxetanyl, azetidinyl, pyrrolidinyl, imidazolidinyl, oxazolidinyl, thiazolidinyl, oxoimidazolidinyl, dioxoimidazolidinyl, oxooxazolidinyl, dioxooxazolidinyl, dioxothiazolidinyl, tetrahydrofuranyl, piperidinyl, morpholinyl, thiomorpholinyl, dioxothiomorpholinyl, tetrahydropyranyl and the like. Examples of "4- to 10-membered non-aryl heterocyclic group" include, in addition to the specific examples for the "4- to 6-membered non-aryl heterocyclic group" described above, azepanyl and the like.

"4- to 10-membered non-aryl heterocyclic group" also encompasses those with a bicyclic structure in which the 4- to 10-membered non-aryl heterocyclic group is fused with a 6-membered aromatic hydrocarbon ring or a 6-membered aromatic heterocycle. Examples of the 6-membered aromatic hydrocarbon ring for forming a fused ring group include a benzene ring and the like. Examples of the 6-membered aromatic heterocycle for forming a fused ring group include pyridine, pyrimidine, pyridazine, and the like. Specific examples of bicyclic "4- to 10-membered non-aryl heterocyclic group" forming a fused ring group include dihydroindolyl, dihydroisoindolyl, dihydropurinyl, dihydrothiazolopyrimidinyl, dihydrobenzodioxanyl, isoindolyl, indazolyl, tetrahydroquinolinyl, tetrahydroisoquinolinyl, tetrahydronaphthyridinyl and the like.

"4- to 10-membered divalent non-aryl heterocyclic group" refers to a divalent non-aryl heterocyclic group comprised of 1 to 2 atoms independently selected from the group consisting of a nitrogen atom, an oxygen atom and a sulfur atom, and 2 to 9 carbon atoms, including those with partially an unsaturated bond and those with a crosslinked structure. Ring-constituting atoms may include oxidized atoms such as —C(O)—, —S(O)—, or —$SO_2$—. "4- to 10-membered divalent non-aryl heterocyclic group" is preferably "4- to 6-membered divalent non-aryl heterocyclic group" Specific examples of "4- to 6-membered divalent non-aryl heterocyclic group" include oxetanylene, azetidinylene, tetrahydrofurylene, pyrrolidinylene, imidazolidinylene, piperidinylene, molpholinylene, thiomolpholinylene, dioxothiomolpholinylene, hexamethyleniminylene, oxazolidinylene, thiazolidinylene, oxoimidazolidinylene, dioxoimidazolidinylene, oxooxazolidinylene, dioxooxazolidinylene, dioxothiazolidinylene, tetrahydrofranylene, tetrahydropyranylene and the like. Examples of "4- to 10-membered divalent non-aryl heterocyclic group" include, in addition to the specific examples for the "4- to 6-membered divalent non-aryl heterocyclic group" described above, azepanylene and the like. As used herein, "azetidinylene" and the like refer to divalent groups derived from "azetidinyl" and the like.

"4- to 10-membered divalent non-aryl heterocyclic group" also encompasses those with a bicyclic structure in which the 4- to 10-membered divalent non-aryl heterocyclic group is fused with a 6-membered aromatic hydrocarbon ring or a 6-membered aromatic heterocycle. Examples of the 6-membered aromatic hydrocarbon ring for forming a fused ring group include a benzene ring and the like. Examples of the 6-membered aromatic heterocycle for forming a fused ring group include pyridine, pyrimidine, pyridazine, and the like. Specific examples of bicyclic "4- to 10-membered divalent non-aryl heterocyclic group" forming a fused ring group include dihydroindolylene, dihydroisoindolylene, dihydropurinylene, dihydrothiazolopyrimidinylene, dihydrobenzodioxanylene, isoindolylene, indazolylene, tetrahydroquinolylene, tetrahydroisoquinolylene, tetrahydronaphthyridinylene and the like.

"$C_{6-10}$ aryl" refers to an aromatic hydrocarbon ring group with 6 to 10 carbon atoms. Specific examples of "$C_{6-10}$ aryl"

include phenyl, 1-naphthyl, 2-naphthyl, and the like. Preferred examples thereof include phenyl.

"$C_{6-10}$ aryl" also encompasses those with a bicyclic structure in which the $C_{6-10}$ aryl is fused with a $C_{4-6}$ alicyclic group or a 5- to 6-membered non-aryl heterocycle. Specific examples of bicyclic "$C_{6-10}$ aryl" forming a fused ring group include the groups represented by the following and the like.

[Chemical Formula 16]

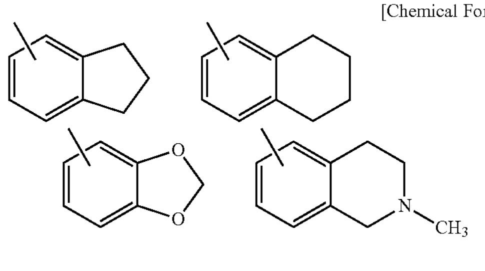

"Aromatic hydrocarbon ring" refers to the cyclic moiety of the "$C_{6-10}$ aryl" described above.

"5- to 10-membered heteroaryl" refers to a cyclic group derived from a monocyclic 5- to 7-membered aromatic heterocycle or a cyclic group derived from a bicyclic 8- to 10-membered aromatic heterocycle, each containing 1 to 4 atoms independently selected from the group consisting of a nitrogen atom, an oxygen atom and a sulfur atom. This is preferably "5- to 7-membered monocyclic heteroaryl", more preferably pyridyl, pyrimidinyl, quinolyl, or isoquinolyl, and still more preferably pyridyl. Specific examples of "5- to 7-membered monocyclic heteroaryl" include pyridyl, pyridazinyl, isothiazolyl, pyrrolyl, furyl, thienyl, thiazolyl, imidazolyl, pyrimidinyl, thiadiazolyl, pyrazolyl, oxazolyl, isoxazolyl, pyrazinyl, triazinyl, triazolyl, oxadiazolyl, triazolyl, tetrazolyl, and the like. Specific examples of "5- to 12-membered heteroaryl" include, in addition to the specific examples for the "5- to 7-membered monocyclic heteroaryl" described above, indolyl, indazolyl, chromenyl, quinolyl, isoquinolyl, benzofuranyl, benzothienyl, benzoxazolyl, benzothiazolyl, benzoisoxazolyl, benzoisothiazolyl, benzotriazolyl, benzoimidazolyl, and the like.

"Aromatic heterocycle" refers to a cyclic moiety of the "5- to 12-membered heteroaryl" described above.

"3- to 10-membered cycloalkane" refers to a cyclic saturated hydrocarbon with 3 to 10 carbon atoms, including those with partially an unsaturated bond and those with a crosslinked structure, and a part of which may be fused with another ring. Specific examples of "3- to 10-membered cycloalkane" include cyclobutane, cyclopentane, cyclohexane, cycloheptane and the like.

"6- to 10-membered aromatic hydrocarbon ring" refers to a cyclic aromatic hydrocarbon with 6 to 10 carbon atoms, and a part of which may be fused with another ring. Specific examples of "6- to 10-membered aromatic hydrocarbon ring" include a benzene ring, naphthalene and the like.

"5- to 10-membered aromatic heterocycle" refers to a monocyclic 5- to 7-membered aromatic heterocycle, or a bicyclic 8- to 10-membered aromatic heterocycle, each containing 1 to 4 atoms independently selected from the group consisting of a nitrogen atom, an oxygen atom and a sulfur atom, and a part of which may be fused with another ring. This is preferably "5- to 6-membered aromatic heterocycle", "5-membered aromatic heterocycle", or "6-membered aromatic heterocycle". Specific examples of "5- to 6-membered aromatic heterocycle" include furan, thiophene, oxazole, pyrazole, pyridine, pyrazine, pyrimidine, pyridazine and the like. Specific examples of "5-membered aromatic heterocycle" include pyrazole, furan, thiophene, oxazole and the like. Specific examples of "6-membered aromatic heterocycle" include pyridine, pyrazine, pyrimidine, pyridazine and the like.

"6- to 10-membered divalent aromatic hydrocarbon ring group" refers to a monocyclic and bicyclic divalent aromatic hydrocarbon ring group with 6 to 10 carbon atoms. "6- to 10-membered divalent aromatic hydrocarbon ring group" is preferably "6-membered divalent aromatic hydrocarbon ring group". Specific examples of "6- to 10-membered divalent aromatic hydrocarbon ring group" and "6-membered divalent aromatic hydrocarbon ring group" include a divalent benzene ring.

"5- to 10-membered divalent aromatic heterocyclic group" refers to a divalent cyclic group derived from a monocyclic 5- to 7-membered aromatic heterocycle, or a divalent cyclic group derived from a bicyclic 8- to 10-membered aromatic heterocycle, each containing 1 to 4 atoms independently selected from the group consisting of a nitrogen atom, an oxygen atom and a sulfur atom. This is preferably "5- to 6-membered divalent aromatic heterocyclic group", more preferably "5-membered divalent aromatic heterocyclic group". Specific examples of "5-membered divalent aromatic heterocyclic group" divalent pyrazole, divalent furan, divalent thiophene, divalent oxazole and the like. Examples of "5- to 10-membered divalent aromatic heterocyclic group" and "5- to 6-membered divalent aromatic heterocyclic group" include, in addition to the specific examples for the "5-membered divalent aromatic heterocyclic group" described above, divalent pyridine, divalent pyrimidine, divalent pyrazine, divalent pyridazine and the like.

"Cancer" refers to malignancy, and encompasses carcinoma, sarcoma, and hematologic malignancy. Specific examples of "cancer" include acoustic neuroma, acute leukemia, acute lymphocytic leukemia, acute myelocytic leukemia (monocytic, myeloblastic, adenocarcinoma, angiosarcoma, astrocytoma, myelomonocytic, and promyelocytic), acute T-cell leukemia, basal cell carcinoma, gall bladder/bile duct cancer, bladder cancer, brain cancer, breast cancer, bronchial cancer, cervical cancer, chondrosarcoma, choriocarcinoma, chorioepithelioma, urothelial carcinoma, chronic leukemia, chronic lymphocytic leukemia, chronic myelocytic (granulocytic) leukemia, chronic myleogeneous leukemia, colorectal cancer, cystadenocarcinoma, diffuse large B-cell lymphoma, dysproliferative changes (dysplasias and metaplasias), embryonal carcinoma, endometrial cancer, epithelial sarcoma, ependymoma, epithelial cancer, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin, and uterus, lymphoid malignancies of T-cell or B-cell origin, leukemia, lymphoma, medullary carcinoma, medulloblastoma, melanoma, meningioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinoma, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, stomach cancer, squamous cell carcinoma, synovioma, sweat gland carcinoma, thyroid cancer, Waldenstrom's macroglobulinemia, testicular tumor, uterine cancer, Wilms' tumor, malignant rhabdoid tumor, epithelioid sarcoma, atypical teratoid/rhabdoid tumor, nerve sheath tumor, chordoid meningioma, neuroepithelial tumor, glioneuronal tumor, craniopharyngioma, glioblastoma, chordoma, myoepithelial tumor, extraskeletal myxoid chondrosarcoma, synovial sarcoma, ossifying fibromyxoid tumor, basaloid squamous cell carcinoma of the paranasal cavity, esophageal adenocarcinoma, papillary thyroid cancer, follicular thyroid cancer, gastrointestinal stromal tumor, pancreatic undifferentiated rhabdoid tumor, digestive system rhabdoid tumor, renal medullary carcinoma, endometrial cancer, myoepithelioma-like tumor in the female vulvar region, colon cancer, mesothelioma, and the like.

"CBP" and "P300" herein are both histone acetyltransferases involved in the regulation of chromatin and are paralogs in relation to each other. "CBP/P300" means "CBP" and "P300". Histone acetyltransferase is mainly, but not solely, an enzyme which transfers an acetyl group to a lysine residue that is present on the amino terminal tail of a histone protein. CBP and P300 mainly, but not solely, acetylate histone H2A, H2B, H3, or H4. In particular, histone H3 mainly, but not solely, acetylates lysine 18, lysine 27, lysine 56, and lysine 122 (H3K18, H3K27, H3K56, and H3K122, respectively) residues. In particular, acetylation of histone H3K27 is known as a marker for an open chromatin, and serves a critical role in the regulation of gene expression (J Hum Genet. 2013 July; 58 (7): 439-45). p53 (Cell. 1997 August; 90(4): 595-606), MyoD (J Biol Chem. 2000 November; 275(44): 34359-34364), STAT3 (Science. 2005 January; 307 (5707): 269-273), Androgen receptor (J Biol Chem. 2000 July; 275 (27): 20853-20860), etc. have been reported as substrates other than histone. When expressed as "CBP" and "P300" herein, a protein is generally referred, but may refer to a nucleic acid encoding the same or a gene as a concept in accordance with the situation. Those skilled in the art can appropriately understand the term in accordance with the context.

Important functional domains of CBP and P300 include HAT domain, bromo domain (BRD), CH1/CH2/CH3 domain (cysteine-histidine rich domains), KIX domain, etc. (Mol Genet Metab. 2016. 119 (1-2): 37-43). HAT domain is mainly, but not solely, a domain that has activity to transfer an acetyl group to a lysine residue that is present on an amino terminal tail of a histone protein. A bromo domain is mainly, but not solely, a protein domain that recognizes an N-acetylated lysine residue found on an amino terminal tail of a histone protein.

The term "CBP" as used herein refers to any naturally-occurring CBP derived from any vertebrate source including mammals such as primates (e.g., human) and rodents (e.g., mouse and rat), unless specified otherwise. The term encompasses unprocessed CBP and any form of CBP resulting from processing in a cell. The term also encompasses naturally-occurring variants of CBP such as splice variants and allelic variants. Human CBP is registered as UniProt Accession Number: Q92793. Representative amino acid sequences of human CBP are set forth in UniProt Q92793-1 (SEQ ID NO: 1) and UniProt Q92793-2 (SEQ ID NO: 2).

The term "P300" as used herein refers to any naturally-occurring P300 derived from any vertebrate source including mammals such as primates (e.g., human) and rodents (e.g., mouse and rat), unless specified otherwise. The term encompasses unprocessed P300 and any form of P300 resulting from processing in a cell. The term also encompasses naturally-occurring variants of P300 such as splice variants and allelic variants. Human P300 is registered as UniProt Accession Number: Q09472. A representative amino acid sequence of human P300 is set forth in UniProt Q09472-1 (SEQ ID NO: 3).

"CBP/P300 inhibitor" is a substance that inactivates, reduces the activity of, and/or reduces the expression of CBP and/or P300. "Reduced expression of CBP/P300" may be expression manifested at any stage such as the level prior to transcription (e.g., genome stage), transcription level, post-transcription regulation level, translation level, or post-translation modification level. "CBP/P300 inhibitor" is preferably a HAT inhibitor or BRD inhibitor, and more preferably a HAT inhibitor.

"HAT inhibitor" is a compound that inhibits the histone acetyltransferase (HAT) activity of CBP and/or P300. For example, a method of detecting CoA-SH generated as a byproduct in a histone acetyltransferase reaction by fluorescence (e.g., Gao T. et al., Methods Mol Biol. 2013; 981: 229-38), a method of detection using a radioisotope (e.g., Lau 0 D et al. J Biol Chem. 2000; 275(29): 21953-9), a method of detecting acetylated histone peptide by TR-FRET (e.g., PerkinElmer, LANCE Ultra or AlphaLISA products), a method of detection using NADH (e.g., Berndsen et al., Methods. 2005; 36(4): 321-31), etc. can be utilized for the detection of histone acetyltransferase activity. Examples of HAT inhibitors include compounds disclosed in WO 2016/044770, WO 2016/044771, WO 2016/044777, WO 2018/235966, WO 2019/111980, WO 2019/049061, WO 2019/161162, WO 2019/161157, WO 2019/201291, and WO 2020/108500.

"BRD inhibitor" is a compound that inhibits the function of a bromo domain (BRD) of CBP and/or P300. For example, a method of detecting a bond between a bromo domain and an acetylated lysine residue by TR-FRET (e.g., Acta Pharmacol Sin. 2020; 41(2): 286-292), etc. can be utilized for the detection of the function of a bromo domain. Examples of BRD inhibitors include compounds disclosed in WO 2017/205538, WO 2016/086200, WO 2018/073586, WO 2019/055877, WO 2017/140728, WO 2019/191667, and WO 2019/195846.

Histone acetyltransferase (HAT) activity is enzymatic activity that transfers an acetyl group to a lysine residue of a substrate protein. Examples of the substrate include a histone protein and p53.

Bromo domain is a protein domain that recognizes an N-acetylated lysine residue. An N-acetylated lysine residue is found on, for example, an amino terminal tail of a histone protein.

In the compounds of the present disclosure represented by Formula (1), (2), (3), (4), (5), (6), (7), (8), (9) or (10), preferred A, B, $R^1$, $R^{2a}$, $R^{2b}$, $R^3$, $R^4$, $R^5$, $R^6$, $R^{7a}$, $R^{7b}$, $R^{7c}$, $R^{7d}$, $R^{7e}$, $R^{7f}$, $R^8$, $R^{9a}$, $R^{9b}$, a, b, Rings Q and Z are as follows, but the technical scope of the present disclosure is not limited to the range of the compounds listed below.

Preferred embodiments of A include CHF, and $CH_2$.

More preferred embodiments of A include CHF.

Other more preferred embodiments of A include $CH_2$.

Preferred embodiments of B include the following Formula (B-1).

[Chemical Formula 17]

(B-1)

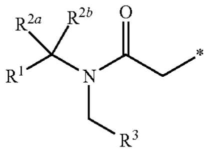

wherein * indicates the binding position to the nitrogen atom on the hydantoin ring.

More preferred embodiments of B include the following Formulas (B-2), (B-3) and (B-4).

[Chemical Formula 18]

(B-2)

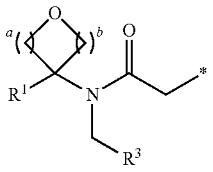

(B-3)

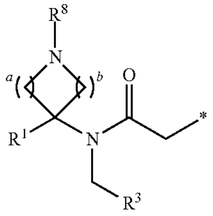

(B-4)

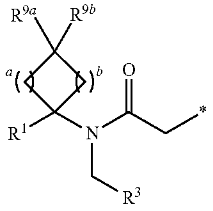

wherein * indicates the binding position to the nitrogen atom on the hydantoin ring.

Preferred embodiments of $R^1$ include $C_{1-6}$ alkyl, and a $C_{3-10}$ alicyclic group (the alkyl or alicyclic group is optionally substituted with 1 to 3 of the same or different halogen atoms).

More preferred embodiments of $R^1$ include $C_{1-6}$ alkyl, and a $C_{3-10}$ alicyclic group (the alkyl or alicyclic group is optionally substituted with 1 to 3 fluorine atoms).

Still more preferred embodiments of $R^1$ include $C_{1-3}$ alkyl optionally substituted with 1 to 3 fluorine.

Yet still more preferred embodiments of $R^1$ include $CF_3$.

Preferred embodiments of $R^{2a}$ and $R^{2b}$ each independently include $C_{1-6}$ alkyl optionally substituted with 1 to 3 of the same or different halogen atoms.

Other preferred embodiments of $R^{2a}$ and $R^{2b}$ include an embodiment in which $R^{2a}$ and $R^{2b}$, together with the carbon atom to which they are attached, form $C_{3-6}$ cycloalkylene, or a 4- to 6-membered divalent non-aryl heterocyclic group (the cycloalkylene or divalent non-aryl heterocyclic group is optionally substituted with 1 to 3 of the same or different halogen atoms).

Most preferred embodiments of $R^{2a}$ and $R^{2b}$ include an embodiment in which $R^{2a}$ and $R^{2b}$, together with the carbon atom to which they are attached, form $C_{3-6}$ cycloalkylene, or a 4- to 6-membered divalent non-aryl heterocyclic group (the cycloalkylene or divalent non-aryl heterocyclic group is optionally substituted with 1 to 3 fluorine atoms).

Preferred embodiments of $R^3$ include $C_{6-10}$ aryl, 5- to 10-membered heteroaryl, a $C_{3-10}$ alicyclic group, and a 4- to 10-membered non-aryl heterocyclic group (the aryl, heteroaryl, alicyclic group or non-aryl heterocyclic group is optionally substituted with 1 to 3 of the same or different substituents selected from the group consisting of a halogen atom and $C_{1-6}$ alkyl).

More preferred embodiments of $R^3$ include $C_{6-10}$ aryl (the aryl is optionally substituted with 1 to 3 of the same or different substituents selected from the group consisting of a halogen atom and $C_{1-6}$ alkyl), and 5- to 10-membered heteroaryl (the heteroaryl is optionally substituted with 1 to 3 of the same or different substituents selected from the group consisting of a halogen atom and $C_{1-6}$ alkyl).

Still more preferred embodiments of $R^3$ include $C_{6-10}$ aryl and 5- to 10-membered heteroaryl (the heteroaryl is optionally substituted with 1 to 3 of the same or different substituents selected from the group consisting of a fluorine atom and $C_{1-6}$ alkyl).

Yet still more preferred embodiments of $R^3$ include 4-fluorophenyl, 4-(trifluoromethyl)phenyl, and 4-fluoro-2-pyridyl, and more preferred embodiments include 4-fluorophenyl, and 4-fluoro-2-pyridyl.

Most preferred embodiments of $R^3$ include 4-fluorophenyl.

Other most preferred embodiments of $R^3$ include 4-fluoro-2-pyridyl.

Preferred embodiments of $R^4$ include a single bond, $C_{1-6}$ alkylene (the alkylene is optionally substituted with 1 to 3 of the same or different substituents selected from the group consisting of a halogen atom and $C_{1-6}$ alkyl), $C_{3-10}$ cycloalkylene (the cycloalkylene is optionally substituted with 1 to 3 of the same or different substituents selected from the group consisting of a halogen atom and $C_{1-6}$ alkyl), and a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $—NR^{11}R^{12}$).

More preferred embodiments of $R^4$ include a single bond, $C_{1-6}$ alkylene (the alkylene is optionally substituted with 1 to 3 of the same or different substituents selected from the group consisting of a halogen atom and $C_{1-6}$ alkyl), and a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $—NR^{11}R^{12}$).

Still more preferred embodiments of $R^4$ include a single bond, $C_{1-6}$ alkylene, and a 4- to 6-membered divalent non-aryl heterocyclic group.

Yet still more preferred embodiments of $R^4$ include a single bond.

Yet still more preferred embodiments of $R^4$ include $C_{1-6}$ alkylene.

Yet still more preferred embodiments of $R^4$ include a 4- to 6-membered divalent non-aryl heterocyclic group.

Most preferred embodiments of $R^4$ include azetidinylene.

Other most preferred embodiments of $R^4$ include methylene.

Preferred embodiments of $R^5$ include a hydrogen atom, a halogen atom, a hydroxyl group, cyano, —$NR^{7b}R^{7c}$, —$SO_2R^{7d}$, —$CONR^{7e}R^{7f}$, $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), $C_{1-6}$ alkenyl (the alkenyl is optionally substituted with 1 to 3 of the same or different substituents selected from the group consisting of a halogen atom, $C_{1-6}$ alkyl, a hydroxyl group and —$NR^{11}R^{12}$), $C_{1-6}$ alkynyl (the alkynyl is optionally substituted with 1 to 3 of the same or different substituents selected from the group consisting of a halogen atom, $C_{1-6}$ alkyl, a hydroxyl group and —$NR^{11}R^{12}$), $C_{1-6}$ alkoxy (the alkoxy is optionally substituted with 1 to 3 of the same or different substituents selected from the group consisting of a halogen atom, $C_{1-6}$ alkyl and —$NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and —$NR^{11}R^{12}$), $C_{6-10}$ aryl (the aryl is optionally substituted with 1 to 3 of the same or different substituents selected from the group consisting of a halogen atom, $C_{1-6}$ alkyl and —$NR^{11}R^{12}$), 5- to 10-membered heteroaryl (the heteroaryl is optionally substituted with 1 to 3 of the same or different substituents selected from the group consisting of a halogen atom, $C_{1-6}$ alkyl and —$NR^{11}R^{12}$), and a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$).

More preferred embodiments of $R^5$ include a hydrogen atom, so a halogen atom, a hydroxyl group, cyano, $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), and a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$).

Still more preferred embodiments of $R^5$ include cyano, $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), and a 4- to 6-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$).

Yet still more preferred embodiments of $R^5$ include $C_{1-6}$ alkyl, and a 4- to 6-membered non-aryl heterocyclic group.

Most preferred embodiments of $R^5$ include a methyl group, and an oxetanyl group.

Preferred embodiments of $R^6$ include a hydrogen atom, and a fluorine atom.

More preferred embodiments of $R^6$ include a hydrogen atom.

Preferred embodiments of $R^{7a}$, $R^{7b}$, $R^{7c}$, $R^{7d}$, $R^{7e}$ and $R^{7f}$ each independently include a hydrogen atom, and $C_{1-6}$ alkyl (the alkyl is optionally substituted with 1 to 3 of the same or different substituents selected from the group consisting of a halogen atom and $C_{1-6}$ alkyl).

More preferred embodiments of $R^{7a}$, $R^{7b}$, $R^{7c}$, $R^{7d}$, $R^{7e}$ and $R^{7f}$ each independently include a hydrogen atom, and a methyl group.

Preferred embodiments of $R^8$ include a hydrogen atom, and $C_{1-6}$ alkyl (the alkyl is optionally substituted with 1 to 3 of the same or different substituents selected from the group consisting of a halogen atom and $C_{1-6}$ alkyl).

More preferred embodiments of $R^{10}$ include $C_{1-6}$ alkyl (the alkyl is optionally substituted with 1 to 3 of the same or different substituents selected from the group consisting of a halogen atom and $C_{1-6}$ alkyl).

Still more preferred embodiments of $R^{10}$ include a methyl group.

Preferred embodiments of $R^{9a}$ and $R^{9b}$ each independently include a hydrogen atom, a halogen atom, and $C_{1-6}$ alkyl (the alkyl is optionally substituted with 1 to 3 of the same or different substituents selected from the group consisting of a halogen atom and $C_{1-6}$ alkyl).

More preferred embodiments of $R^{9a}$ and $R^{9b}$ each independently include a halogen atom.

Still more preferred embodiments of $R^{9a}$ and $R^{9b}$ include a fluorine atom.

Preferred embodiments of $R^{10}$ include $C_{1-6}$ alkyl.

Preferred embodiments of $R^{11}$ and $R^{12}$ each independently include a hydrogen atom and $C_{1-6}$ alkyl.

Other Preferred embodiments of $R^{11}$ and $R^{12}$ include an embodiment in which $R^{11}$ and $R^{12}$ that attach to the same nitrogen atom, when both are $C_{1-6}$ alkyl, together with the nitrogen atom to which each is attached, form a 3- to 8-membered nitrogen-containing non-aryl heterocyclic group.

More preferred embodiments of $R^{11}$ and $R^{12}$ include a methyl group.

Preferred embodiments of Ring Q include a 6- to 10-membered aromatic hydrocarbon ring (the aromatic hydrocarbon ring is optionally substituted with 1 to 3 of the same or different substituents selected from the group consisting of a halogen atom and $C_{1-6}$ alkyl).

More preferred embodiments of Ring Q include a benzene ring (the benzene ring is optionally substituted with 1 to 3 of the same or different substituents selected from the group consisting of a halogen atom and $C_{1-6}$ alkyl).

Still more preferred embodiments of Ring Q include a benzene ring.

Preferred embodiments of Z include —O—, a 6- to 10-membered divalent aromatic ring group (the divalent aromatic ring group is optionally substituted with 1 to 3 of the same or different substituents selected from the group consisting of a halogen atom, $C_{1-6}$ alkyl and —$NR^{11}R^{12}$), a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$), and a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$).

More preferred embodiments of Z include a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), and a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$).

Still more preferred embodiments of Z include a 5-membered divalent aromatic heterocyclic group (the divalent aromatic heterocyclic group is optionally substituted with 1 to 3 of the same or different substituents selected from the group consisting of a halogen atom, $C_{1-6}$ alkyl and $—NR^{11}R^{12}$).

Yet still more preferred embodiments of Z include a divalent pyrazole group.

Preferred embodiments of a include 0, 1, and 2.

More preferred embodiments of a include 1, and 2.

Still more preferred embodiments of a include 1.

Preferred embodiments of b include 1, and 2.

More preferred embodiments of b include 1.

More preferred embodiments of a and b include an embodiment in which both are 1.

One embodiment of the compound represented by Formula (1) includes the following (A).

(A) A compound or a pharmaceutically acceptable salt thereof, wherein

A is CHF, or $CH_2$,

B is the following Formula (B-1):

[Chemical Formula 19]

(B-1)

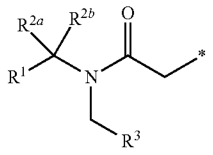

wherein * indicates the binding position to the nitrogen atom on the hydantoin ring, Ring Q is a 6- to 10-membered aromatic hydrocarbon ring (the aromatic hydrocarbon ring is optionally substituted with 1 to 3 of the same or different substituents selected from the group consisting of a halogen atom and $C_{1-6}$ alkyl), Z is —O—, a 6- to 10-membered divalent aromatic ring group (the divalent aromatic ring group is optionally substituted with 1 to 3 of the same or different substituents selected from the group consisting of a halogen atom, $C_{1-6}$ alkyl and $—NR^{11}R^{12}$), a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and $—NR^{11}R^{12}$), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $—NR^{11}R^{12}$), $R^1$ is $C_{1-3}$ alkyl optionally substituted with 1 to 3 fluorine, $R^{2a}$ and $R^{2b}$, together with the carbon atom to which they are attached, form $C_{3-6}$ cycloalkylene, or a 4- to 6-membered divalent non-aryl heterocyclic group (the cycloalkylene or divalent non-aryl heterocyclic group is optionally substituted with 1 to 3 fluorine atoms), $R^3$ is $C_{6-10}$ aryl (the aryl is optionally substituted with 1 to 3 of the same or different substituents selected from the group consisting of a halogen atom and optionally substituted $C_{1-6}$ alkyl), or 5- to 10-membered heteroaryl (the heteroaryl is optionally substituted with 1 to 3 of the same or different substituents selected from the group consisting of a halogen atom and $C_{1-6}$ alkyl), $R^4$ is a single bond, $C_{1-6}$ alkylene (the alkylene is optionally substituted with 1 to 3 of the same or different substituents selected from the group consisting of a halogen atom and $C_{1-6}$ alkyl), $C_{3-10}$ cycloalkylene (the cycloalkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $—NR^{11}R^{12}$), $R^5$ is a hydrogen atom, a halogen atom, a hydroxyl group, cyano, $—NR^{7b}R^{7c}$, $—SO_2R^{7d}$, $—CONR^{7e}R^{7f}$, $C_{1-6}$ alkyl (the alkyl is optionally substituted with 1 to 3 of the same or different substituents selected from the group consisting of a halogen atom, $C_{1-6}$ alkyl, a hydroxyl group and $—NR^{11}R^{12}$), $C_{1-6}$ alkenyl (the alkenyl is optionally substituted with 1 to 3 of the same or different substituents selected from the group consisting of a halogen atom, $C_{1-6}$ alkyl, a hydroxyl group and $—NR^{11}R^{12}$), $C_{1-6}$ alkynyl (the alkynyl is optionally substituted with 1 to 3 of the same or different substituents selected from the group consisting of a halogen atom, $C_{1-6}$ alkyl, a hydroxyl group and $—NR^{11}R^{12}$), $C_{1-6}$ alkoxy (the alkoxy is optionally substituted with 1 to 3 of the same or different substituents selected from the group consisting of a halogen atom, $C_{1-6}$ alkyl and $—NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and $—NR^{11}R^{12}$), $C_{6-10}$ aryl (the aryl is optionally substituted with 1 to 3 of the same or different substituents selected from the group consisting of a halogen atom, $C_{1-6}$ alkyl and $—NR^{11}R^{12}$), 5- to 10-membered heteroaryl (the heteroaryl is optionally substituted with 1 to 3 of the same or different substituents selected from the group consisting of a halogen atom, $C_{1-6}$ alkyl and $—NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and $—NR^{11}R^{12}$), $R^{7b}$, $R^{7c}$, $R^{7d}$, $R^{7e}$ and $R^{7f}$ are each independently a hydrogen atom, or $C_{1-6}$ alkyl (the alkyl is optionally substituted with 1 to 3 of the same or different substituents selected from the group consisting of a halogen atom and $C_{1-6}$ alkyl), and $R^{11}$ and $R^{12}$ are each independently a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

One embodiment of the compound represented by Formula (1) includes the following (B).

(B) A compound or a pharmaceutically acceptable salt thereof, wherein

A is CHF, or $CH_2$,

B is the following Formula (B-2), (B-3), or (B-4):

[Chemical Formula 20]

(B-2)

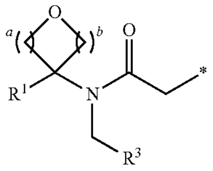

(B-3)

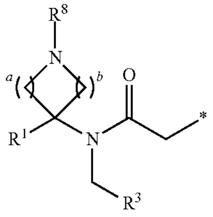

(B-4)

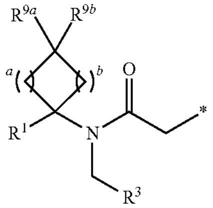

wherein * indicates the binding position to the nitrogen atom on the hydantoin ring, a is 0, 1, or 2, b is 1, or 2, $R^3$ is a hydrogen atom, or $C_{1-6}$ alkyl (the alkyl is optionally substituted with 1 to 3 of the same or different substituents selected from the group consisting of a halogen atom and $C_{1-6}$ alkyl), $R^{9a}$ and $R^{9b}$ are each independently a hydrogen atom, a halogen atom, or $C_{1-6}$ alkyl (the alkyl is optionally substituted with 1 to 3 of the same or different substituents selected from the group consisting of a halogen atom and $C_{1-6}$ alkyl), Ring Q is a 6- to 10-membered aromatic hydrocarbon ring (the aromatic hydrocarbon ring is optionally substituted with 1 to 3 of the same or different substituents selected from the group consisting of a halogen atom and $C_{1-6}$ alkyl), Z is —O—, a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and $—NR^{11}R^{12}$), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $—NR^{11}R^{12}$), $R^1$ is $CF_3$, $R^3$ is 4-fluorophenyl, 4-(trifluoromethyl)phenyl, or 4-fluoro-2-pyridyl, $R^4$ is a single bond, $C_{1-6}$ alkylene (the alkylene is optionally substituted with 1 to 3 of the same or different substituents selected from the group consisting of a halogen atom and $C_{1-6}$ alkyl), $C_{3-10}$ cycloalkylene (the cycloalkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $—NR^{11}R^{12}$), $R^5$ is a hydrogen atom, a halogen atom, a hydroxyl group, cyano, $—NR^{7b}R^{7c}$, $—SO_2R^{7d}$, $—CONR^{7e}R^{7f}$, $C_{1-6}$ alkyl (the alkyl is optionally substituted with 1 to 3 of the same or different substituents selected from the group consisting of a halogen atom, $C_{1-6}$ alkyl, a hydroxyl group and $—NR^{11}R^{12}$), $C_{1-6}$ alkenyl (the alkenyl is optionally substituted with 1 to 3 of the same or different substituents selected from the group consisting of a halogen atom, $C_{1-6}$ alkyl, a hydroxyl group and $—NR^{11}R^{12}$), $C_{1-6}$ alkynyl (the alkynyl is optionally substituted with 1 to 3 of the same or different substituents selected from the group consisting of a halogen atom, $C_{1-6}$ alkyl, a hydroxyl group and $—NR^{11}R^{12}$), $C_{1-6}$ alkoxy (the alkoxy is optionally substituted with 1 to 3 of the same or different substituents selected from the group consisting of a halogen atom, $C_{1-6}$ alkyl and $—NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and $—NR^{11}R^{12}$), $C_{6-10}$ aryl (the aryl is optionally substituted with 1 to 3 of the same or different substituents selected from the group consisting of a halogen atom, $C_{1-6}$ alkyl and $—NR^{11}R^{12}$), 5- to 10-membered heteroaryl (the heteroaryl is optionally substituted with 1 to 3 of the same or different substituents selected from the group consisting of a halogen atom, $C_{1-6}$ alkyl and $—NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and $—NR^{11}R^{12}$), $R^{7b}$, $R^{7c}$, $R^{7d}$, $R^{7e}$ and $R^{7f}$ are each independently a hydrogen atom, or $C_{1-6}$ alkyl (the alkyl is optionally substituted with 1 to 3 of the same or different substituents selected from the group consisting of a halogen atom and $C_{1-6}$ alkyl), and $R^{11}$ and $R^{12}$ are each independently a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

One embodiment of the compound represented by Formula (2) includes the following (C).

(C) A compound or a pharmaceutically acceptable salt thereof, wherein

A is CHF, or $CH_2$, $R^3$ is 4-fluorophenyl, or 4-fluoro-2-pyridyl,

Z is a 4- to 10-membered divalent aromatic ring group (the divalent aromatic ring group is optionally substituted with 1 to 3 of the same or different substituents selected from the group consisting of a halogen atom, $C_{1-6}$ alkyl and —$NR^{11}R^{12}$), or a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$), $R^4$ is a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), $R^5$ is $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), $R^6$ is a hydrogen atom, or a halogen atom, and $R^{11}$ and $R^{12}$ are each independently a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

One embodiment of the compound represented by Formula (2) includes the following (D).

(D) A compound or a pharmaceutically acceptable salt thereof, wherein

A is CHF,

Z is a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), or a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$), $R^4$ is a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), $R^5$ is $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), $R^6$ is a hydrogen atom, and $R^{11}$ and $R^{12}$ are each independently a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

One embodiment of the compound represented by Formula (3) includes the following (E).

(E) A compound or a pharmaceutically acceptable salt thereof, wherein $R^3$ is 4-fluorophenyl, or 4-fluoro-2-pyridyl, $R^4$ is a single bond, $C_{1-6}$ alkylene (the alkylene is optionally substituted with 1 to 3 of the same or different substituents selected from the group consisting of a halogen atom and $C_{1-6}$ alkyl), or a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), $R^5$ is $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), and $R^{11}$ and $R^{12}$ are each independently a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

One embodiment of the compound represented by Formula (3) includes the following (F).

(F) A compound or a pharmaceutically acceptable salt thereof, wherein $R^3$ is 4-fluorophenyl, or 4-fluoro-2-pyridyl, $R^4$ is a 4- to 6-membered divalent non-aryl heterocyclic group, and $R^5$ is $C_{1-3}$ alkyl, or a 4- to 6-membered non-aryl heterocyclic group (the non-aryl heterocyclic group is optionally substituted with 1 to 3 of the same or different substituents selected from the group consisting of a halogen atom and $C_{1-6}$ alkyl).

One embodiment of the compound represented by Formula (3) includes the following (G).

(G) A compound or a pharmaceutically acceptable salt thereof, wherein $R^3$ is 4-fluorophenyl, or 4-fluoro-2-pyridyl, $R^4$ is azetidinylene or piperidinylene, and $R^5$ is oxetanyl.

One embodiment of the compound represented by Formula (4) includes the following (H).

(H) A compound or a pharmaceutically acceptable salt thereof, wherein $R^3$ is 4-fluorophenyl, or 4-fluoro-2-pyridyl, $R^4$ is azetidinylene, and $R^5$ is oxetanyl.

One embodiment of the compound represented by Formula (5) includes the following (I).

(I) A compound or a pharmaceutically acceptable salt thereof, wherein

A is CHF, or $CH_2$,

Z is a 6- to 10-membered divalent aromatic ring group (the divalent aromatic ring group is optionally substituted with 1 to 3 of the same or different substituents selected from the group consisting of a halogen atom, $C_{1-6}$ alkyl and —$NR^{11}R^{12}$), or a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$), $R^3$ is 4-fluorophenyl, or 4-fluoro-2-pyridyl, $R^4$ is a single bond, $C_{1-6}$ alkylene (the alkylene is optionally substituted with 1 to 3 of the same or different substituents selected from the group consisting of a halogen atom and $C_{1-6}$ alkyl), or $C_{3-10}$ cycloalkylene (the cycloalkylene is optionally substituted with 1 to 3 of the same or different substituents selected from the group consisting of a halogen atom and $C_{1-6}$ alkyl), $R^5$ is a hydrogen atom, a hydroxyl group, cyano, $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), $R^6$ is a hydrogen atom, or a halogen atom, $R^3$ is $C_{1-6}$ alkyl, and $R^{11}$ and $R^{12}$ are each independently a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

One embodiment of the compound represented by Formula (5) includes the following (J).

(J) A compound or a pharmaceutically acceptable salt thereof, wherein

A is CHF,

Z is a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and —$NR^{11}R^{12}$), or a 5- to 10-membered divalent aromatic heterocyclic group (the divalent aromatic heterocyclic group is optionally substituted with 1 to 3 of the same or different substituents selected from the group consisting of a halogen atom, $C_{1-6}$ alkyl and —$NR^{11}R^{12}$), $R^3$ is 4-fluorophenyl, or 4-fluoro-2-pyridyl, $R^4$ is a single bond, or $C_{1-6}$ alkylene (the alkylene is optionally substituted with 1 to 3 of the same or different substituents selected from the group consisting of a halogen atom and $C_{1-6}$ alkyl), $R^5$ is a hydroxyl group, cyano, $C_{1-6}$ alkyl (the alkyl is optionally substituted with 1 to 3 of the same or different substituents selected from the group consisting of a halogen atom, $C_{1-6}$ alkyl, a hydroxyl group and —$NR^{11}R^{12}$), a $C_{3-10}$ alicyclic group (the alicyclic group is optionally substituted with 1 to 3 of the same or different substituents selected from the group consisting of a halogen atom, $C_{1-6}$ alkyl and —$NR^{11}R^{12}$), or a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and —$NR^{11}R^{12}$), $R^6$ is a hydrogen atom, $R^{10}$ is a methyl group, and $R^{11}$ and $R^{12}$ are each independently a hydrogen atom or $C_{1-6}$ alkyl, and if there are multiple instances of $R^{11}$ or $R^{12}$, each of $R^{11}$ or $R^{12}$ may be the same or different, wherein $R^{11}$ and $R^{12}$ that attach to the same nitrogen atom, when both are $C_{1-6}$ alkyl, together with the nitrogen atom to which each is attached, may form a 3- to 8-membered nitrogen-containing non-aryl heterocyclic group.

One embodiment of the compound represented by Formula (6) includes the following (K).

(K) A compound or a pharmaceutically acceptable salt thereof, wherein $R^3$ is 4-fluorophenyl, or 4-fluoro-2-pyridyl, $R^4$ is a single bond, or $C_{1-6}$ alkylene (the alkylene is optionally substituted with 1 to 3 of the same or different substituents selected from the group consisting of a halogen atom and $C_{1-6}$ alkyl), and $R^5$ is a hydroxyl group, cyano, $C_{1-6}$ alkyl, a $C_{3-10}$ alicyclic group, or a 4- to 10-membered non-aryl heterocyclic group.

One embodiment of the compound represented by Formula (6) includes the following (L).

(L) A compound or a pharmaceutically acceptable salt thereof, wherein $R^3$ is 4-fluorophenyl, or 4-fluoro-2-pyridyl, $R^4$ is a single bond, or $C_{1-6}$ alkylene (the alkylene is optionally substituted with 1 to 3 of the same or different substituents selected from the group consisting of a halogen atom and $C_{1-6}$ alkyl), and $R^5$ is a methyl group, or oxetanyl.

One embodiment of the compound represented by Formula (6) includes the following (M).

(M) A compound or a pharmaceutically acceptable salt thereof, wherein $R^3$ is 4-fluorophenyl, or 4-fluoro-2-pyridyl, $R^4$ is a single bond, and $R^5$ is a methyl group.

One embodiment of the compound represented by Formula (7) includes the following (N).

(N) A compound or a pharmaceutically acceptable salt thereof, wherein $R^3$ is 4-fluorophenyl, or 4-fluoro-2-pyridyl, $R^4$ is a single bond, and $R^5$ is a methyl group.

One embodiment of the compound represented by Formula (8) includes the following (O).

(O) A compound or a pharmaceutically acceptable salt thereof, wherein

A is CHF, or $CH_2$,

Z is a 5-membered divalent aromatic heterocyclic group (the divalent aromatic heterocyclic group is optionally substituted with 1 to 3 of the same or different substituents selected from the group consisting of a halogen atom, $C_{1-6}$ alkyl and $—NR^{11}R^{12}$), $R^3$ is 4-fluorophenyl, or 4-fluoro-2-pyridyl, $R^4$ is a 4- to 10-membered divalent non-aryl heterocyclic group (the divalent non-aryl heterocyclic group is optionally substituted with 1 to 3 of the same or different substituents selected from the group consisting of a halogen atom, $C_{1-6}$ alkyl and $—NR^{11}R^{12}$), $R^5$ is a 4- to 10-membered non-aryl heterocyclic group (the non-aryl heterocyclic group is optionally substituted with 1 to 3 of the same or different substituents selected from the group consisting of a halogen atom, $C_{1-6}$ alkyl and $—NR^{11}R^{12}$), $R^6$ is a hydrogen atom, or a halogen atom, and $R^{9a}$ and $R^{9b}$ are fluorine atoms.

One embodiment of the compound represented by Formula (9) includes the following (P).

(P) A compound or a pharmaceutically acceptable salt thereof, wherein $R^3$ is 4-fluorophenyl, or 4-fluoro-2-pyridyl, $R^4$ is a 4- to 6-membered divalent non-aryl heterocyclic group, and $R^5$ is a 4- to 6-membered non-aryl heterocyclic group.

One embodiment of the compound represented by Formula (9) includes the following (Q).

(Q) A compound or a pharmaceutically acceptable salt thereof, wherein $R^3$ is 4-fluorophenyl, or 4-fluoro-2-pyridyl, $R^4$ is azetidinylene, and $R^5$ is oxetanyl.

One embodiment of the compound represented by Formula (10) includes the following (R).

(R) A compound or a pharmaceutically acceptable salt thereof, wherein $R^3$ is 4-fluorophenyl, or 4-fluoro-2-pyridyl, $R^4$ is a 4- to 6-membered divalent non-aryl heterocyclic group, and $R^5$ is a 4- to 6-membered non-aryl heterocyclic group.

One embodiment of the compound represented by Formula (10) includes the following (S).

(S) A compound or a pharmaceutically acceptable salt thereof, wherein $R^3$ is 4-fluorophenyl, or 4-fluoro-2-pyridyl, $R^4$ is azetidinylene, and $R^5$ is oxetanyl.

The route of administration of the compound of the present disclosure may be oral administration, parenteral administration, or rectal administration, and the daily dosage may vary depending on the type of compound, the administration method, the symptoms and age of the patient, etc. For example, in the case of oral administration, usually about 0.01 to 1000 mg, more preferably about 0.1 to 500 mg per kg body weight of a human or mammal can be administered once or several times in divided doses. In the case of parenteral administration such as intravenous injection, for example, usually about 0.01 mg to 300 mg, more preferably about 1 mg to 100 mg per kg body weight of a human or mammal can be administered. The administration schedule may include, for example, a single administration, administration once a day for three consecutive days, or administration twice a day for one week. Furthermore, each administration method described above may be repeated at intervals of about 1 day to about 60 days.

The compound of the present disclosure can be administered parenterally or orally, directly or by preparation using an appropriate dosage form. Examples of dosage forms include, but are not limited to, tablets, capsules, powders, granules, liquids, suspensions, injections, patches, poultices, etc. The preparations are produced by known methods using pharmaceutically acceptable additives. Depending on the purpose, the additives may be excipients, disintegrants, binders, glidants, lubricants, coating agents, solvents, solubilizing agents, thickeners, dispersants, stabilizers, sweeteners, flavors and the like. Specific examples of the additives include lactose, mannitol, crystalline cellulose, low-substituted hydroxypropyl cellulose, corn starch, partially pregelatinized starch, carmellose calcium, croscarmellose sodium, hydroxypropyl cellulose, hydroxypropyl methyl cellulose, polyvinyl alcohol, magnesium stearate, sodium stearyl fumarate, polyethylene glycol, propylene glycol, titanium oxide, talc and the like.

The production method of the compounds of the present disclosure represented by Formulas (1)-(10) will be described below with examples, but the production method of the compound of the present disclosure is not limited thereto. The compounds used in the following production method may form a salt, as long as they do not adversely affect the reaction.

The compound of the present disclosure can be produced from a known compound as a starting raw material by, for example, Production Method A, B, C, or D described below, or a method analogous thereto, or in appropriate combination with a synthetic method well known to those skilled in the art.

Production Method A

Compound (1-11), which is the compound represented by Formula (1) wherein A is CHF, and Q is a benzene ring, can be produced by, for example, the following production method.

wherein $R^1$, $R^{2a}$, $R^{2b}$, $R^3$, $R^4$, $R^5$ and Z are as defined in [Item 1] above, and $R^6$ is as defined in [Item 16] above.

Step 1-1: Production Process for Compound (1-3)

Compound (1-3) can be produced by reacting Compound (1-1) with Compound (1-2) in the presence of a reducing agent in an inert solvent.

Examples of the reducing agent include sodium borohydride, sodium triacetoxyborohydride, sodium cyanoborohydride and the like.

Examples of the inert solvent include halogenated hydrocarbons such as chloroform, dichloromethane and the like; aromatic hydrocarbons such as toluene and the like; ether solvents such as diethyl ether, tetrahydrofuran (THF), 1,4-dioxane and the like; acetonitrile, acetone, methyl ethyl ketone, dimethylformamide, N-methyl-2-pyrrolidinone and the like.

The reaction temperature is not particularly limited, but is selected from the range of usually 0° C. to 150° C., preferably 0° C. to 25° C. The reaction time is usually 1 hours to 72 hours, preferably 1 hours to 24 hours.

[Chemical Formula 21]

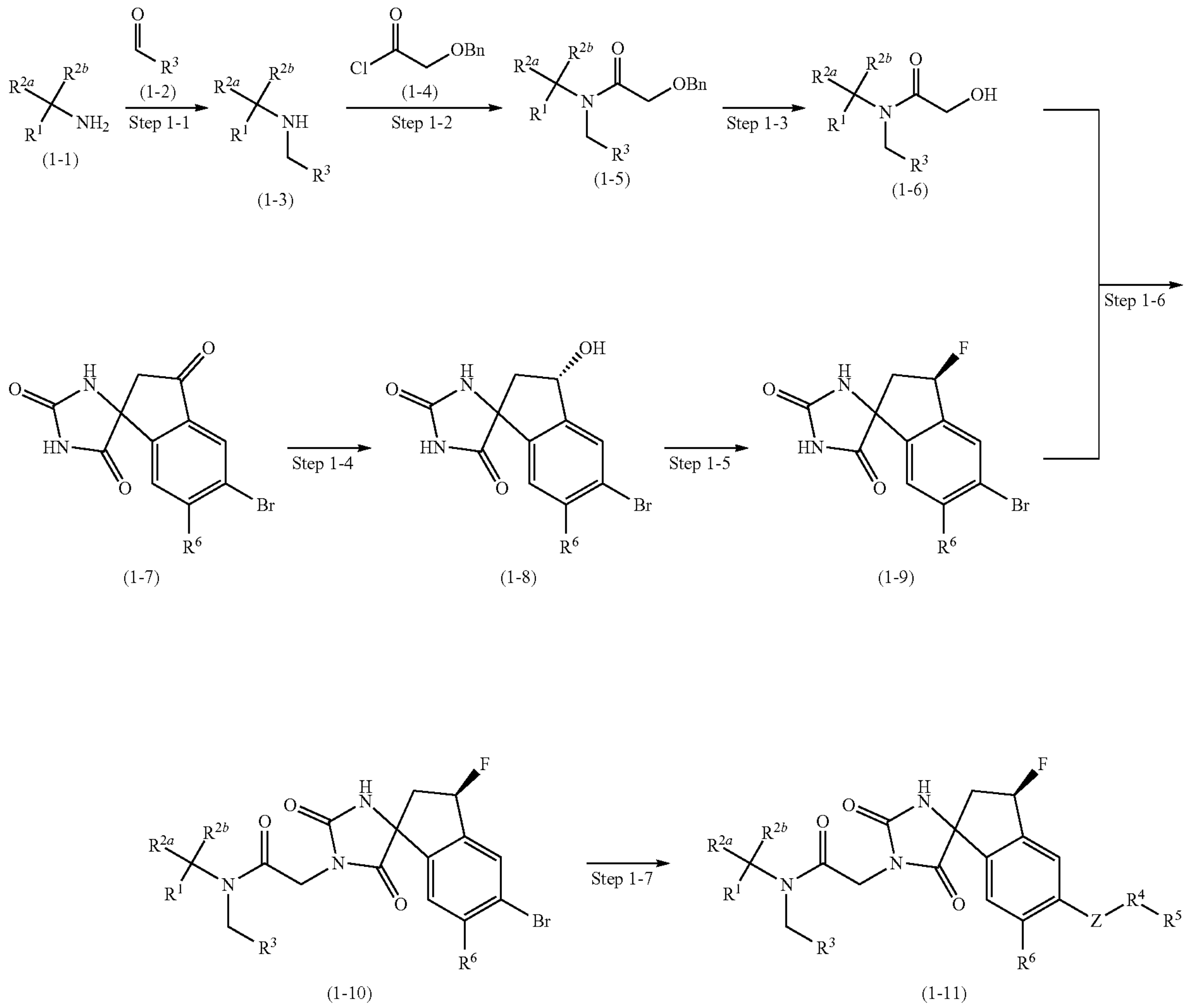

Step 1-2: Production Process for Compound (1-5)

Compound (1-5) can be produced by subjecting Compound (1-3) to an amidation reaction with Compound (1-4) in the presence of a base in an inert solvent.

Examples of the base include inorganic bases such as potassium hydroxide, sodium hydroxide, sodium hydride and the like; metal alkoxides such as sodium methoxide, potassium tert-butoxide and the like, and the like.

Examples of the inert solvent include halogenated hydrocarbons such as chloroform, dichloromethane and the like; aromatic hydrocarbons such as toluene and the like; ether solvents such as diethyl ether, tetrahydrofuran (THF), 1,4-dioxane and the like; aprotic polar solvents such as acetonitrile, acetone, methyl ethyl ketone, N,N-dimethylformamide, N-methyl-2-pyrrolidinone, N,N-dimethylpropylene urea and the like, and the like.

The reaction temperature is not particularly limited, but is selected from the range of usually 0° C. to 150° C., preferably 25° C. to 100° C. The reaction time is usually 1 hours to 72 hours, preferably 1 hours to 24 hours.

Step 1-3: Production Process for Compound (1-6)

Compound (1-6) can be produced by removing the benzyl group of Compound (1-5). For example, catalytic reduction using a metal catalyst such as palladium/carbon, palladium hydroxide/carbon or the like under hydrogen atmosphere, or the like is applied.

The reaction temperature is not particularly limited, but is selected from the range of usually 0° C. to 100° C., preferably 0° C. to 25° C. The reaction time is usually 1 hours to 72 hours, preferably 1 hours to 24 hours.

Step 1-4: Production Process for Compound (1-8)

Compound (1-8) can be produced by reacting Compound (1-7) with a reducing agent. Compound (1-7) can be synthesized by the method described in WO 2016/044770.

Examples of the reducing agent include sodium borohydride, sodium triacetoxyborohydride, sodium cyanoborohydride and the like.

The reaction temperature is not particularly limited, but is selected from the range of usually −78° C. to 150° C., preferably −78° C. to 25° C. The reaction time is usually 30 minutes to 72 hours, preferably 30 minutes to 24 hours.

Step 1-5: Production Process for Compound (1-9)

Compound (1-9) can be produced by reacting Compound (1-8) with a fluorinating agent in an inert solvent.

Examples of the inert solvent include halogenated hydrocarbons such as chloroform, dichloromethane and the like; aromatic hydrocarbons such as toluene and the like; ether solvents such as diethyl ether, tetrahydrofuran (THF), 1,4-dioxane and the like; aprotic polar solvents such as acetonitrile, acetone, methyl ethyl ketone, N,N-dimethylformamide, N-methyl-2-pyrrolidinone, N,N-dimethylpropylene urea and the like, and the like.

Examples of the fluorinating agent include (diethylamino) sulfur trifluoride, FLUOLEAD™ and the like.

The reaction temperature is not particularly limited, but is selected from the range of usually −78° C. to 150° C., preferably −78° C. to 25° C. The reaction time is usually 1 hours to 72 hours, preferably 1 hours to 24 hours.

Step 1-6: Production Process for Compound (1-10)

Compound (1-10) can be produced by subjecting Compound (1-9) to Mitsunobu reaction with Compound (1-6) in the presence of Mitsunobu reagent an inert solvent.

Examples of the inert solvent include aromatic hydrocarbons such as toluene and the like; ether solvents such as diethyl ether, tetrahydrofuran (THF), 1,4-dioxane and the like, and the like.

Examples of the Mitsunobu reagent include a combination of diethyl azodicarboxylate (DEAD), diisopropyl azodicarboxylate (DIAD), bis(2-methoxyethyl) azodicarboxylate, or N,N,N',N'-tetramethylazodicarboxamide with triphenylphosphine or tributylphosphine and the like. Cyanomethylenetrimethylphosphorane (Tsunoda reagent) can also be used.

The reaction temperature is not particularly limited, but is selected from the range of usually 0° C. to 100° C. The reaction time is usually 1 hours to 72 hours, preferably 1 hours to 24 hours.

Step 1-7: Production Process for Compound (1-11)

Compound (1-11) can be produced by subjecting Compound (1-10) to a palladium-catalyzed cross-coupling reaction with various coupling reagents in an inert solvent.

Examples of the inert solvent include aromatic hydrocarbons such as toluene and the like; ether solvents such as diethyl ether, tetrahydrofuran (THF), 1,4-dioxane and the like; aprotic polar solvents such as acetonitrile, acetone, methyl ethyl ketone, N,N-dimethylformamide, N-methyl-2-pyrrolidinone, N,N-dimethylpropylene urea and the like, and the like.

Examples of the palladium reagent include tetrakis(triphenylphosphine)palladium(0), bis(dibenzylideneacetone)palladium(0), tris(dibenzylideneacetone)dipalladium(0), bis(tri-tert-butylphosphine)palladium(0), [1,1'-bis(diphenylphosphino)ferrocene]palladium(II) dichloride and the like.

Examples of the base include inorganic bases such as potassium carbonate, sodium carbonate, cesium carbonate, potassium phosphate, potassium hydroxide, sodium hydroxide and the like.

Examples of the coupling reagent include a boronic acid to which Z is bonded, a boronic acid pinacol ester to which Z is bonded, and the like.

The reaction temperature is not particularly limited, but is selected from the range of usually 0° C. to 150° C., preferably 25° C. to 100° C. The reaction time is usually 1 hours to 72 hours, preferably 1 hours to 24 hours.

Production Method B

Compound (1-14), which is the compound represented by Formula (1) wherein Q is a benzene ring, can also be produced by, for example, the following production method.

[Chemical Formula 22]

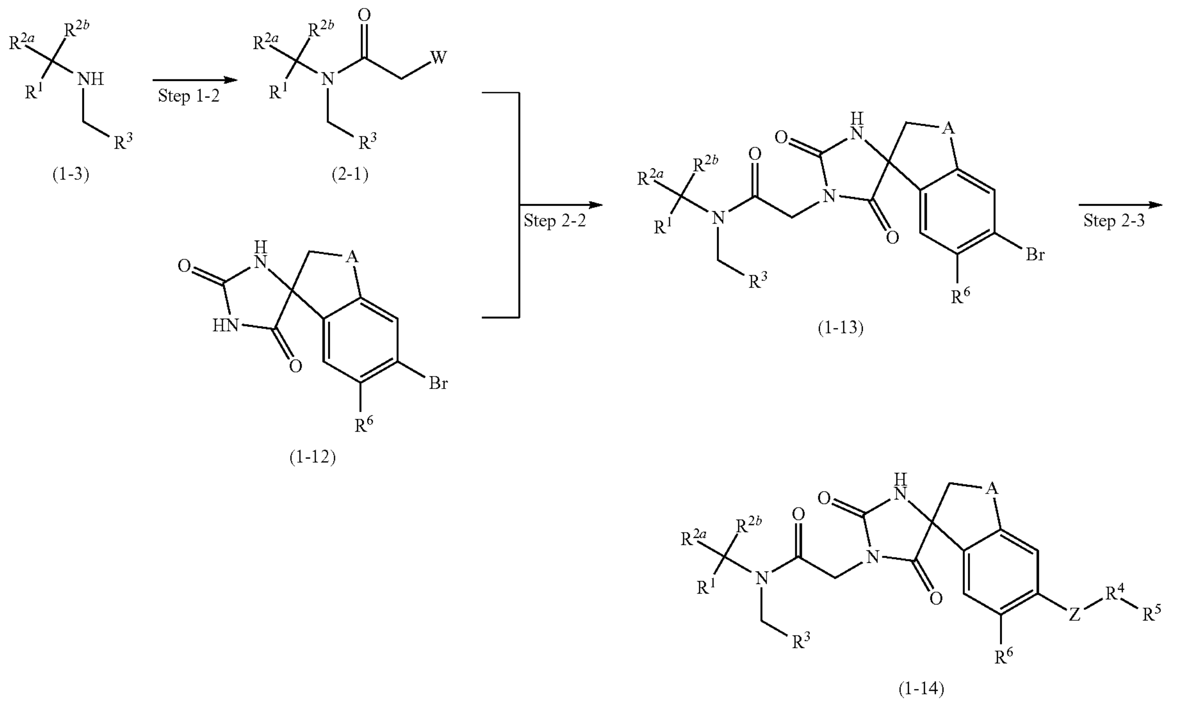

(1-3) (2-1) (1-12) (1-13) (1-14)

wherein A, $R^1$, $R^{2a}$, $R^{2b}$, $R^3$, $R^4$, $R^5$, and Z are as defined in [Item 1] above. $R^6$ is as defined in [Item 16] above. W represents a halogen atom.

Step 2-1: Production Process for Compound (2-1)

Compound (2-1) can be produced by reacting Compound (1-3) with an amidating agent in an inert solvent.

Examples of the amidating agent include chloroacetyl chloride, bromoacetyl chloride, chloroacetic anhydride and the like.

Examples of the inert solvent include halogenated hydrocarbons such as chloroform, dichloromethane and the like; aromatic hydrocarbons such as toluene and the like; ether solvents such as diethyl ether, tetrahydrofuran (THF), 1,4-dioxane and the like; aprotic polar solvents such as acetonitrile, acetone, methyl ethyl ketone, N,N-dimethylformamide, N-methyl-2-pyrrolidinone, N,N-dimethylpropylene urea and the like, pyridine and the like.

The reaction temperature is not particularly limited, but is selected from the range of usually 0° C. to 150° C., preferably 25° C. to 100° C. The reaction time is usually 1 hours to 72 hours, preferably 1 hours to 24 hours.

Step 2-2: Production Process for Compound (1-13)

Compound (1-13) can be produced by subjecting Compound (1-12) to an alkylation reaction with Compound (2-1) in the presence of a base in an inert solvent.

Examples of the inert solvent include aromatic hydrocarbons such as toluene and the like; ether solvents such as diethyl ether, tetrahydrofuran (THF), 1,4-dioxane and the like; aprotic polar solvents such as acetonitrile, acetone, methyl ethyl ketone, N,N-dimethylformamide, N-methyl-2-pyrrolidinone, N,N-dimethylpropylene urea and the like, and the like.

Examples of the base include inorganic bases such as potassium carbonate, cesium carbonate and the like; metal alkoxides such as sodium methoxide, potassium tert-butoxide and the like, and the like.

The reaction temperature is not particularly limited, but is selected from the range of usually 0° C. to 100° C. The reaction time is usually 1 hours to 72 hours, preferably 1 hours to 24 hours.

Step 2-3: Production Process for Compound (1-14)

Compound (1-14) can be produced by subjecting Compound (1-13) to a palladium-catalyzed cross-coupling reaction with various coupling reagents in an inert solvent.

Examples of the inert solvent include aromatic hydrocarbons such as toluene and the like; ether solvents such as diethyl ether, tetrahydrofuran (THF), 1,4-dioxane and the like; aprotic polar solvents such as acetonitrile, acetone, methyl ethyl ketone, N,N-dimethylformamide, N-methyl-2-pyrrolidinone, N,N-dimethylpropylene urea and the like, and the like.

Examples of the palladium reagent include tetrakis(triphenylphosphine)palladium(0), bis(dibenzylideneacetone)palladium(0), tris(dibenzylideneacetone)dipalladium(0), bis(tri-tert-butylphosphine)palladium(0), [1,1'-bis(diphenylphosphino)ferrocene]palladium(II) dichloride and the like.

Examples of the base include inorganic bases such as potassium carbonate, sodium carbonate, cesium carbonate, potassium phosphate, potassium hydroxide, sodium hydroxide and the like.

Examples of the coupling reagent include a boronic acid to which Z is bonded, a boronic acid pinacol ester to which Z is bonded, and the like.

The reaction temperature is not particularly limited, but is selected from the range of usually 0° C. to 150° C., preferably 25° C. to 100° C. The reaction time is usually 1 hours to 72 hours, preferably 1 hours to 24 hours.

Production Method C

Compound (1-14), which is the compound represented by Formula (1) wherein Q is a benzene ring, can also be produced by, for example, the following production method.

Examples of the coupling reagent include a boronic acid to which Z is bonded, a boronic acid pinacol ester to which Z is bonded, and the like.

The reaction temperature is not particularly limited, but is selected from the range of usually 0° C. to 150° C., preferably 25° C. to 100° C. The reaction time is usually 1 hours to 72 hours, preferably 1 hours to 24 hours.

[Chemical Formula 23]

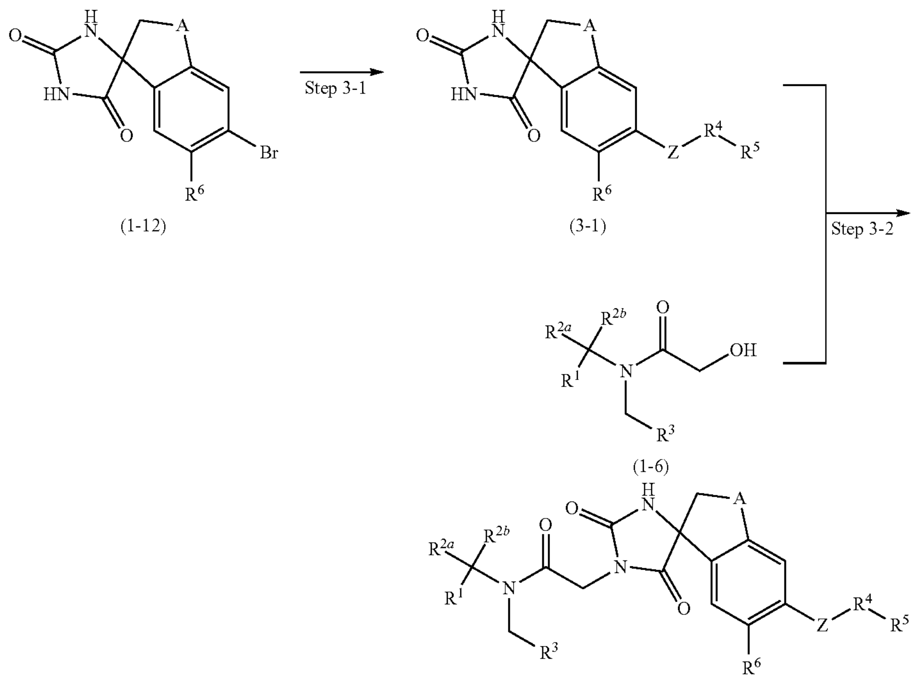

(1-12) (3-1) (1-6) (1-14)

wherein A, $R^1$, $R^{2a}$, $R^{2b}$, $R^3$, $R^4$, $R^5$, and Z are as defined in [Item 1] above. $R^6$ is as defined in [Item 16] above.

Step 3-1: Production Process for Compound (3-1)

Compound (3-1) can be produced by subjecting Compound (1-12) to a palladium-catalyzed cross-coupling reaction with various coupling reagents in an inert solvent.

Examples of the inert solvent include aromatic hydrocarbons such as toluene and the like; ether solvents such as diethyl ether, tetrahydrofuran (THF), 1,4-dioxane and the like; aprotic polar solvents such as acetonitrile, acetone, methyl ethyl ketone, N,N-dimethylformamide, N-methyl-2-pyrrolidinone, N,N-dimethylpropylene urea and the like, and the like.

Examples of the palladium reagent include tetrakis(triphenylphosphine)palladium(0), bis(dibenzylideneacetone)palladium(0), tris(dibenzylideneacetone)dipalladium(0), bis(tri-tert-butylphosphine)palladium(0), [1,1'-bis(diphenylphosphino)ferrocene]palladium(II) dichloride and the like.

Examples of the base include inorganic bases such as potassium carbonate, sodium carbonate, cesium carbonate, potassium phosphate, potassium hydroxide, sodium hydroxide and the like.

Step 3-2: Production Process for Compound (1-14)

Compound (1-14) can be produced by subjecting Compound (3-1) to Mitsunobu reaction with Compound (1-6) in the presence of Mitsunobu reagent in an inert solvent.

Examples of the inert solvent include aromatic hydrocarbons such as toluene and the like; ether solvents such as diethyl ether, tetrahydrofuran (THF), 1,4-dioxane and the like, and the like.

Examples of the Mitsunobu reagent include a combination of diethyl azodicarboxylate (DEAD), diisopropyl azodicarboxylate (DIAD), bis(2-methoxyethyl) azodicarboxylate, or N,N,N',N'-tetramethylazodicarboxamide with triphenylphosphine or tributylphosphine and the like. Cyanomethylenetrimethylphosphorane (Tsunoda reagent) can also be used.

The reaction temperature is not particularly limited, but is selected from the range of usually 0° C. to 100° C. The reaction time is usually 1 hours to 72 hours, preferably 1 hours to 24 hours.

Production Method D

Compound (1-14), which is the compound represented by Formula (1) wherein Q is a benzene ring, can also be produced by, for example, the following production method.

[Chemical Formula 24]

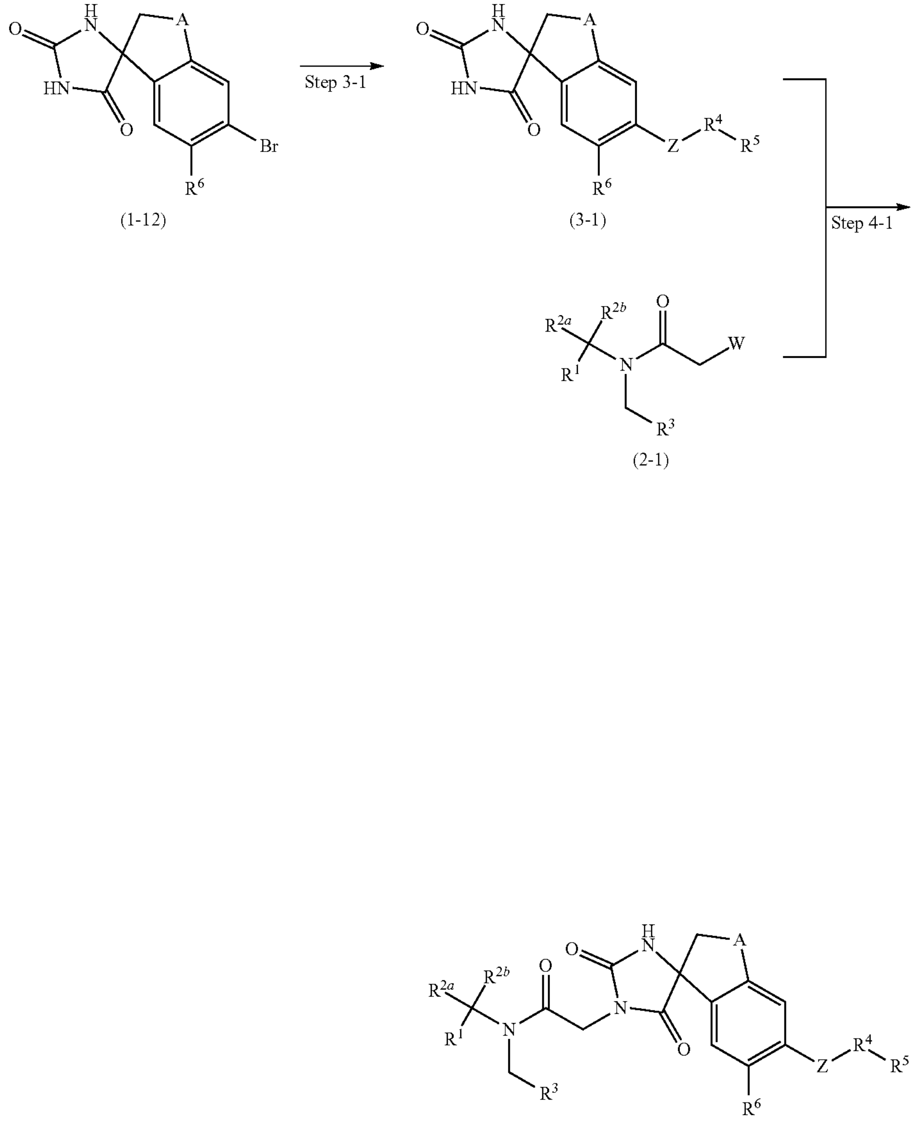

(1-12) (3-1) (2-1) (1-14)

wherein A, $R^1$, $R^{2a}$, $R^{2b}$, $R^3$, $R^4$, $R^5$, and Z are as defined in [Item 1] above. $R^6$ is as defined in [Item 16] above. W represents a halogen atom.

Step 4-1: Production Process for Compound (1-14)

Compound (1-14) can be produced by subjecting Compound (3-1) to an alkylation reaction with Compound (2-1) in the presence of a base in an inert solvent.

Examples of the inert solvent include aromatic hydrocarbons such as toluene and the like; ether solvents such as diethyl ether, tetrahydrofuran (THF), 1,4-dioxane and the like; aprotic polar solvents such as acetonitrile, acetone, methyl ethyl ketone, N,N-dimethylformamide, N-methyl-2-pyrrolidinone, N,N-dimethylpropylene urea and the like, and the like.

Examples of the base include inorganic bases such as potassium carbonate, cesium carbonate and the like; metal alkoxides such as sodium methoxide, potassium tert-butoxide and the like, and the like.

The reaction temperature is not particularly limited, but is selected from the range of usually 0° C. to 100° C. The reaction time is usually 1 hours to 72 hours, preferably 1 hours to 24 hours.

Production Method E

Compound (1-17), which is the compound represented by Formula (1) wherein A is $CH_2$, and Q is a benzene ring, can be produced by, for example, the following production method.

[Chemical Formula 25]

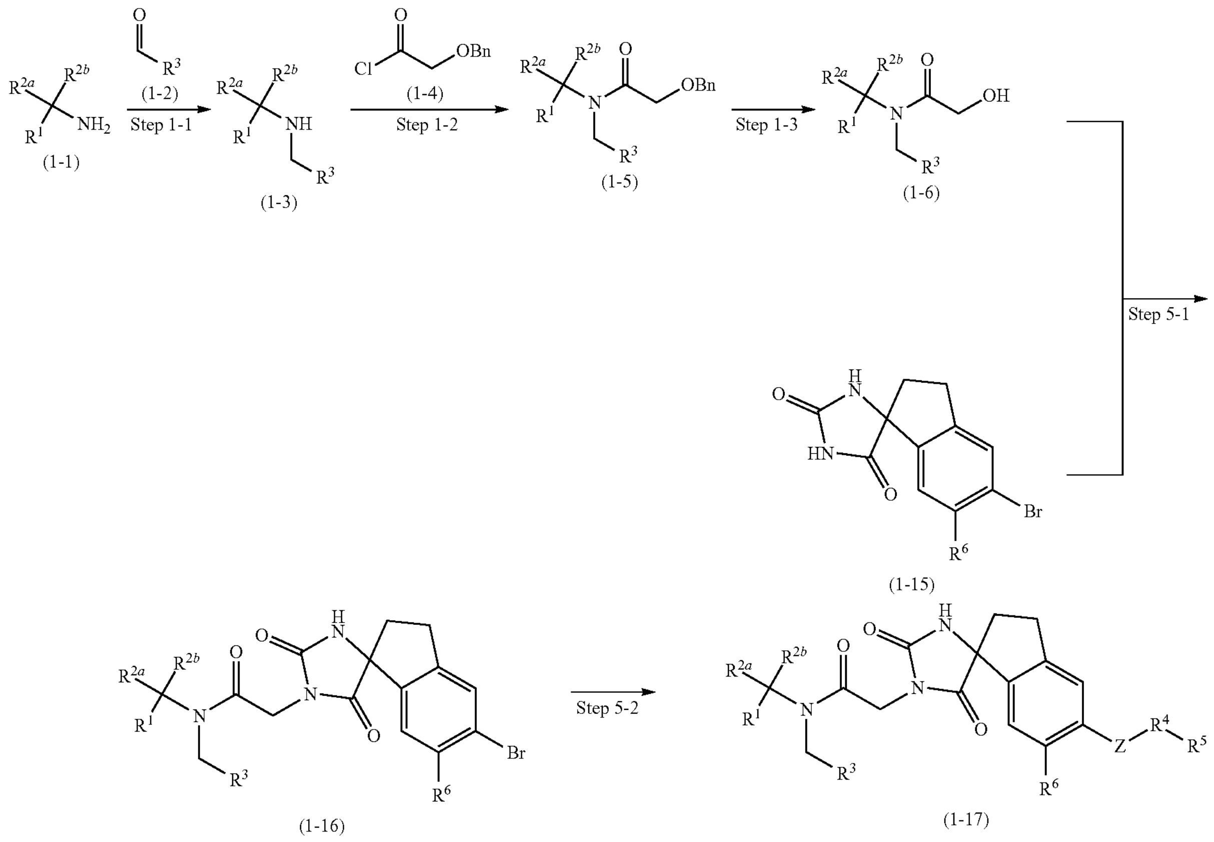

wherein $R^1$, $R^{2a}$, $R^{2b}$, $R^3$, $R^4$, $R^5$ and Z are as defined in [Item 1] above, and $R^6$ is as defined in [Item 16] above.

Step 5-1: Production Process for Compound (1-16)

Compound (1-16) can be produced by subjecting Compound (1-15) to Mitsunobu reaction with Compound (1-6) in the presence of Mitsunobu reagent in an inert solvent. Compound (1-15) can be synthesized by the method described in WO 2016/044770.

Examples of the inert solvent include aromatic hydrocarbons such as toluene and the like; ether solvents such as diethyl ether, tetrahydrofuran (THF), 1,4-dioxane and the like, and the like.

Examples of the Mitsunobu reagent include a combination of diethyl azodicarboxylate (DEAD), diisopropyl azodicarboxylate (DIAD), bis(2-methoxyethyl) azodicarboxylate, or N,N,N',N'-tetramethylazodicarboxamide with triphenylphosphine or tributylphosphine and the like. Cyanomethylenetrimethylphosphorane (Tsunoda reagent) can also be used.

The reaction temperature is not particularly limited, but is selected from the range of usually 0° C. to 100° C. The reaction time is usually 1 hours to 72 hours, preferably 1 hours to 24 hours.

Step 5-2: Production Process for Compound (1-17)

Compound (1-17) can be produced by subjecting Compound (1-16) to a palladium-catalyzed cross-coupling reaction with various coupling reagents in an inert solvent.

Examples of the inert solvent include aromatic hydrocarbons such as toluene and the like; ether solvents such as diethyl ether, tetrahydrofuran (THF), 1,4-dioxane and the like; aprotic polar solvents such as acetonitrile, acetone, methyl ethyl ketone, N,N-dimethylformamide, N-methyl-2-pyrrolidinone, N,N-dimethylpropylene urea and the like, and the like.

Examples of the palladium reagent include tetrakis(triphenylphosphine)palladium(0), bis(dibenzylideneacetone)palladium(0), tris(dibenzylideneacetone)dipalladium(0), bis(tri-tert-butylphosphine)palladium(0), [1,1'-bis(diphenylphosphino)ferrocene]palladium(II) dichloride and the like.

Examples of the base include inorganic bases such as potassium carbonate, sodium carbonate, cesium carbonate, potassium phosphate, potassium hydroxide, sodium hydroxide and the like.

Examples of the coupling reagent include a boronic acid to which Z is bonded, a boronic acid pinacol ester to which Z is bonded, and the like.

The reaction temperature is not particularly limited, but is selected from the range of usually 0° C. to 150° C., preferably 25° C. to 100° C. The reaction time is usually 1 hours to 72 hours, preferably 1 hours to 24 hours.

In the production method described above, the starting raw materials and intermediates for which the production method is not described are available as commercial products, or can be synthesized from a commercially available product by a method known to those skilled in the art or a method analogous thereto.

In each reaction of the production methods described above, protecting groups can be used as necessary, even if the use of protecting groups is not explicitly described. For example, the target compound can be obtained by protecting the portion other than the reaction point as necessary and deprotecting the portion after the completion of the reaction or series of reactions, if any functional group other than the reaction point changes under the described reaction condition or if the absence of a protecting group is unsuitable for carrying out the described method.

As the protecting group, the protecting group described in Protective Groups in Organic Synthesis (Theodora W. Greene, Peter G. M. Wuts, published by John Wiley & Sons, Inc., 1999) etc., or the like can be used. Specific examples of amino-protecting group include benzyloxycarbonyl, tert-butoxycarbonyl, acetyl, benzyl and the like. Specific examples of hydroxyl-protecting group include trialkyl silyl such as trimethylsilyl, tert-butyldimethylsilyl and the like, acetyl, benzyl and the like.

The introduction or removal of protecting groups can be carried out by a method commonly used in synthetic organic chemistry (see, for example, the aforementioned Protective Groups in Organic Synthesis) or a method analogous thereto.

As used herein, protecting groups, condensing agents, or the like may be denoted by the nomenclature of IUPAC-IUB (Biochemical Nomenclature Committees) that is commonly used in the art. It should be noted that compound names used herein do not necessarily follow the IUPAC nomenclature.

The intermediates or target compounds in the production methods described above can also be introduced into another compound contained in the present disclosure by appropriately converting its functional group (e.g., various conversions using amino, a hydroxyl group, carbonyl, halogen, or the like while protecting or deprotecting a functional group as needed). The conversion of functional groups can be carried out by a common method usually used (see, for example, Comprehensive Organic Transformations, R. C. Larock, John Wiley & Sons Inc. (1999), etc.).

The intermediates or target compounds in the production methods described above can be isolated and purified by a purification method commonly used in organic synthetic chemistry (e.g., neutralization, filtration, extraction, washing, drying, concentration, recrystallization, various chromatographies). The intermediates can also be used in the subsequent reaction without any particular purification.

As the protecting group, the protecting group described in Protective Groups in Organic Synthesis (Theodora W. Greene, Peter G. M. Wuts, published by John Wiley & Sons, Inc., 1999) etc., or the like can be used. Specific examples of amino-protecting group include benzyloxycarbonyl, tert-butoxycarbonyl, acetyl, benzyl and the like. Specific examples of hydroxyl-protecting group include trialkyl silyl such as trimethylsilyl, tert-butyldimethylsilyl and the like, acetyl, benzyl and the like.

The introduction or removal of protecting groups can be carried out by a method commonly used in synthetic organic chemistry (see, for example, the aforementioned Protective Groups in Organic Synthesis) or a method analogous thereto.

As used herein, protecting groups, condensing agents, or the like may be denoted by the nomenclature of IUPAC-IUB (Biochemical Nomenclature Committees) that is commonly used in the art. It should be noted that compound names used herein do not necessarily follow the IUPAC nomenclature.

The intermediates or target compounds in the production methods described above can also be introduced into another compound contained in the present disclosure by appropriately converting its functional group (e.g., various conversions using amino, a hydroxyl group, carbonyl, halogen, or the like while protecting or deprotecting a functional group as needed). The conversion of functional groups can be carried out by a common method usually used (see, for example, Comprehensive Organic Transformations, R. C. Larock, John Wiley & Sons Inc. (1999), etc.).

The intermediates or target compounds in the production methods described above can be isolated and purified by a purification method commonly used in organic synthetic chemistry (e.g., neutralization, filtration, extraction, washing, drying, concentration, recrystallization, various chromatographies). The intermediates can also be used in the subsequent reaction without any particular purification.

Examples of the "pharmaceutically acceptable salt" include acid addition salts and base addition salts. Examples of the acid addition salt include inorganic acid salts such as hydrochloride, hydrobromide, sulfurate, hydroiodide, nitrate, phosphorate and the like, or organic acid salts such as citrate, oxalate, phthalic acid salt, fumarate, maleate, succinic acid salt, malic acid salt, acetate, formate, propionate, benzoate, trifluoroacetate, methanesulfonate, benzenesulfonate, para-toluenesulfonate, camphorsulfonate and the like. Examples of the base addition salt include inorganic base salts such as sodium salt, potassium salt, calcium salt, magnesium salt, barium salt, aluminium salt and the like, or salts with organic base such as trimethylamine, triethylamine, pyridine, picoline, 2,6-lutidine, ethanolamine, diethanolamine, triethanolamine, tromethamine [tris(hydroxymethyl)methylamine], tert-butylamine, cyclohexylamine, dicyclohexylamine, N,N-dibenzyl ethylamine and the like. Examples of the "pharmaceutically acceptable salt" also include amino acid salts with basic or acidic amino acids such as arginine, lysine, ornithine, aspartic acid, or glutamic acid and the like.

Salts suitable for the starting raw materials and intermediates and salts acceptable as raw materials for pharmaceutical products are conventionally used nontoxic salts. Examples thereof include acid addition salts such as organic acid salts (e.g., acetate, trifluoroacetate, maleate, fumarate, citrate, tartrate, methanesulfonate, benzenesulfonate, formate, toluenesulfonate, etc.) and inorganic acid salts (e.g., hydrochloride, hydrobromide, hydroiodide, sulfurate, nitrate, phosphate, etc.), salts with amino acids (e.g., arginine, aspartic acid, glutamic acid, etc.), metal salts such as alkali metal salts (e.g., sodium salt, potassium salt, etc.), alkaline-earth metal salts (e.g., calcium salt, magnesium salt, etc.) and the like, ammonium salts, organic base salts (e.g., trimethylamine salt, triethylamine salt, pyridine salt, picoline salt, dicyclohexylamine salt, N,N'-dibenzyl ethylene diamine salt, etc.) and the like. Those skilled in the art can appropriately select these salts.

The compounds of the present disclosure may be substituted with isotopes (e.g.,$^{2}$H (or D), $^{3}$H (or T), $^{11}$C, $^{13}$C, $^{14}$C, $^{13}$N, $^{15}$N, $^{15}$O, $^{35}$S, $^{18}$F, $^{125}$I, etc.), and these compounds are also encompassed by the compound of the present disclosure.

The present disclosure encompasses the compounds represented by formulas (1) to (10) and pharmaceutically acceptable salts thereof. The compound of the present disclosure can also be in a form of a hydrate and/or solvate of various solvents (ethanolate, etc.). Thus, such hydrates and/or solvates are also encompassed by the compound of the present disclosure.

The compound of the present disclosure also encompasses all other possible isomers such as optical isomers based on an optically-active center, atropisomers based on axial or planar chirality resulting from restriction of intramolecular rotation, other stereoisomers, tautomers, geometric isomers, and crystalline forms in any form, and mixtures thereof.

In particular, an optical isomer and an atropisomer can be obtained as a racemate, or an optically-active form if an optically-active starting material or intermediate is used, respectively. If necessary, the corresponding raw material, intermediate, or final product racemate can be physically or chemically resolved, during an appropriate step of the production method described above, into their optical enantiomers by a known separation method such as a method using an optically active column or a fractional crystallization method. Examples of the resolution method include a diastereomer method in which two types of diastereomers are synthesized by reacting a racemate with an optically-active resolving agent, and the diastereomers are then resolved by a method such as a fractional crystallization method, utilizing the difference in their physical properties.

If it is desirable to obtain a pharmaceutically acceptable salt of the compound of the present disclosure, a compound represented by formula (1) to (10), when obtained in a form of a pharmaceutically acceptable salt, may be directly purified, or when obtained in a free form, a salt may be formed by dissolving or suspending the compound in a suitable organic solvent and adding an acid or a base according to a common method.

The compound of the present disclosure can be used concomitantly with another drug in order to enhance the effect thereof. Specifically, the compound of the present disclosure can be used concomitantly with a drug such as a hormonal therapy agent, a chemotherapeutic agent, an immunotherapeutic agent, an agent inhibiting a cell growth factor and its receptor action. Hereinafter, a drug that can be used in combination with the compound of the present disclosure is abbreviated as additional drug.

Although the compound of the present disclosure exhibits excellent anticancer action when used as a single agent, the effect thereof can be further enhanced, or the QOL of a patient can be improved by concomitantly using one or several of the additional drugs described above (concomitant use of multiple drugs).

Examples of "hormonal therapy agent" include fosfestrol, diethylstilbestrol, chlorotrianisene, medroxyprogesterone acetate, megestrol acetate, chlormadinone acetate, cyproterone acetate, danazol, dienogest, asoprisnil, allylestrenol, gestrinone, nomegestol, tadenan, mepartricin, raloxifene, ormeroxifene, levormeloxifene, antiestrogens (e.g., tamoxifen citrate, toremifene citrate, and the like), pill formulations, mepitiostane, testolactone, aminoglutethimide, LH-RH derivatives (LH-RH agonists (e.g., goserelin acetate, buserelin, leuprorelin, and the like), and LH-RH antagonists), droloxifene, epitiostanol, ethinylestradiol sulfonate, aromatase inhibitors (e.g., fadrozole hydrochloride, anastrozole, letrozole, exemestane, vorozole, formestane, and the like), antiandrogens (e.g., flutamide, enzalutamide, apalutamide, bicalutamide, nilutamide, and the like), adrenocortical hormone agents (e.g., dexamethasone, prednisolone, betamethasone, triamcinolone, and the like), androgen synthesis inhibitors (e.g., abiraterone and the like), retinoids, drugs that slow the metabolism of retinoids (e.g., liarozole and the like), and the like.

For example, an alkylating agent, antimetabolite, anticancer antibiotic, plant derived anticancer agent, molecularly targeted therapy agent, immunomodulator, other chemotherapeutic agent, or the like can be used as a "chemotherapeutic agent". Representative examples thereof are described below.

Examples of "alkylating agents" include nitrogen mustard, nitrogen mustard n-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucide, carboplatin, cisplatin, miboplatin, nedaplatin, oxaliplatin, altretamine, ambamustine, dibrospidium chloride, fotemustine, prednimustine, pumitepa, ribomustin, temozolomide, treosulfan, trofosfamide, zinostatin stimalamer, adozelesin, cystemustine, bizelesin, trabectedin, DDS formulations thereof, and the like.

Examples of "antimetabolite" include mercaptopurine, 6-mercaptopurine riboside, thioinosine, methotrexate, pemetrexed, enocitabine, cytarabine, cytarabine ocfosfate, ancitabine hydrochloride, 5-FU based agents (e.g., fluorouracil, tegafur, UFT, doxifluridine, carmofur, galocitabine, emitefur, capecitabine, and the like), aminopterin, nelzarabine, leucovorin calcium, tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamustine, bendamustine, DDS formulations thereof, and the like.

Examples of "anticancer antibiotic" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, eribulin, DDS formulations thereof, and the like.

Examples of "plant derived anticancer agent" include etoposide, etoposide phosphate, vinblastine sulfate, vincristine sulfate, vindesine sulfate, teniposide, paclitaxel, docetaxel, DJ-927, vinorelbine, irinotecan, topotecan, DDS formulations thereof, and the like.

Examples of "molecularly targeted therapy agent" include imatinib, gefitinib, erlotinib, sorafenib, dasatinib, sunitinib, nilotinib, lapatinib, pazopanib, ruxolitinib, crizotinib, vemurafenib, vandetanib, ponatinib, cabozantinib, tofacitinib regorafenib, bosutinib, axitinib, dabrafenib, trametinib, nintedanib, idelalisib, ceritinib, lenvatinib, palbociclib, alectinib, afatinib, osimertinib, ribociclib, abemaciclib, brigatinib, neratinib, copanlisib, cobimetinib, ibrutinib, acalabrutinib, encorafenib, binimetinib, baricitinib, fostamatinib, lorlatinib, erdafitinib, entrectinib, dacomitinib, sirolimus, everolimus, temsirolimus, olaparib, rucaparib, niraparib, venetoclax, azacitidine, decitabine, vorinostat, panobinostat, tazemetostat, romidepsin, bortezomib, carfilzomib, larotrectinib, ixazomib, and the like.

Examples of "immunomodulator" include lenalidomide, pomalidomide, and the like.

Examples of "other chemotherapeutic agent" include sobuzoxane and the like.

Examples of "immunotherapeutic agent (BRM)" include picibanil, krestin, sizofiran, lentinan, ubenimex, interferon, interleukin, macrophage colony stimulating factor, granulocyte-colony stimulating factor, erythropoietin, lymphotoxin, BCG vaccine, *Corynebacterium parvum*, levamisole, polysaccharide K, procodazole, anti-CTLA4 antibody, anti-PD-1 antibody, anti-PD-Li antibody, and Toll-like Receptor agonist (e.g., TLR7 agonist, TLR8 agonist, TLR9 agonist, and the like).

The cell growth factor in an agent inhibiting a cell growth factor and its receptor action can be any substance, as long as it is a substance that promotes cell growth. A cell growth factor is generally a peptide having a molecular weight of 20,000 or less and exerting action at a low concentration by binding with a receptor. Specific examples thereof include EGF (epidermal growth factor) or substances having substantially the same activity as EGF (e.g., TGF-alpha and the like), insulin or substances having substantially the same activity as insulin (e.g., insulin, IGF (insulin-like growth factor)-1, IGF-2, and the like), FGF (fibroblast growth factor) or substances having substantially the same activity as FGF (e.g., acidic FGF, basic FGF, KGK (keratinocyte growth factor), FGF-10, and the like), and other cell growth factors (e.g., CSF (colony stimukating factor), EPO (erythropoietin), IL-2 (interleukin-2), NGF (nerve growth factor), PDGF (platelet-derived growth factor), TGF-beta (transforming growth factor beta), HGF (hepatocyte growth factor), VEGF (vascular endothelial growth factor), heregulin, angiopoietin, and the like).

"SMARC deficient cancer" is cancer with deficiency of an SMARC gene, and/or lack of or attenuation of expression of an SMARC protein. Preferably, this is cancer with deficiency of an SMARC gene, and/or lack of expression of an SMARC protein. More preferably, this is cancer with deficiency of an SMARCB1 gene, SMARCA2 gene, SMARCA4 gene, or SMARCA2/A4 gene. Specific examples thereof include malignant rhabdoid tumor, epithelioid sarcoma, atypical teratoid/rhabdoid tumor, nerve sheath tumor, chordoid meningioma, neuroepithelial tumor, glioneuronal tumor, craniopharyngioma, glioblastoma, chordoma, myoepithelial tumor, undifferentiated round cell sarcoma, rhabdomyosarcoma, extraskeletal myxoid chondrosarcoma, synovial sarcoma, ossifying fibromyxoid tumor, basaloid squamous cell carcinoma of the paranasal cavity, esophageal adenocarcinoma, papillary thyroid cancer, follicular thyroid cancer, gastrointestinal stromal tumor, pancreatic undifferentiated rhabdoid tumor, digestive system rhabdoid tumor, renal medullary carcinoma, uterine cancer, myoepithelioma-like tumor in the female vulvar region, colon cancer, mesothelioma, pulmonary adenocarcinoma, large cell lung carcinoma, lung neuroendocrine tumor, esophageal cancer, gastroesophageal junction cancer, gastric cancer, bladder cancer, squamous cell lung cancer, pancreatic cancer, medulloblastoma, renal clear cell carcinoma, liver cancer, small cell carcinoma of the ovary, mucinous ovarian tumor, uterine cancer, uterus sarcoma, nasal and paranasal sinus cancer, thoracic cavity sarcoma, pleomorphic carcinoma, thoracic sarcoma, small cell carcinoma of the ovary, primary gallbladder tumor, and uterus sarcoma. Preferred are malignant rhabdoid tumor and pulmonary adenocarcinoma.

"SMARCB1 deficient cancer" is cancer with deficiency of an SMARCB1 gene, and/or lack of or attenuation of expression of an SMARCB1 protein. Preferably, this is cancer with deficiency of an SMARCB1 gene, and/or lack of expression of an SMARCB1 protein. More preferably, this is cancer with deficiency of an SMARCB1 gene. Specific examples thereof include malignant rhabdoid tumor, epithelioid sarcoma, atypical teratoid/rhabdoid tumor, nerve sheath tumor, chordoid meningioma, neuroepithelial tumor, glioneuronal tumor, craniopharyngioma, glioblastoma, chordoma, myoepithelial tumor, undifferentiated round cell sarcoma, rhabdomyosarcoma, extraskeletal myxoid chondrosarcoma, synovial sarcoma, ossifying fibromyxoid tumor, basaloid squamous cell carcinoma of the paranasal cavity, esophageal adenocarcinoma, papillary thyroid cancer, follicular thyroid cancer, gastrointestinal stromal tumor, pancreatic undifferentiated rhabdoid tumor, digestive system rhabdoid tumor, renal medullary carcinoma, uterine cancer, myoepithelioma-like tumor in the female vulvar region, colon cancer, and mesothelioma. Preferred is malignant rhabdoid tumor.

"SMARCA2 deficient cancer" is cancer with deficiency of an SMARCA2 gene, and/or lack of or attenuation of expression of an SMARCA2 protein. Preferably, this is cancer with deficiency of an SMARCA2 gene, and/or lack of expression of an SMARCA2 protein. More preferably, this is cancer with deficiency of an SMARCA2 gene. Specific examples thereof include pulmonary adenocarcinoma, large cell lung carcinoma, lung neuroendocrine tumor, esophageal cancer, gastroesophageal junction cancer, and malignant rhabdoid tumor. Preferred is pulmonary adenocarcinoma.

"SMARCA4 deficient cancer" is cancer with deficiency of an SMARCA4 gene, and/or lack of or attenuation of expression of an SMARCA4 protein. Preferably, this is cancer with deficiency of an SMARCA4 gene, and/or lack of expression of an SMARCA4 protein. More preferably, this is cancer with deficiency of an SMARCA4 gene. Specific examples thereof include pulmonary adenocarcinoma, esophageal cancer, gastroesophageal junction cancer, gastric cancer, bladder cancer, squamous cell lung cancer, pancreatic cancer, medulloblastoma, renal clear cell carcinoma, liver cancer, small cell carcinoma of the ovary, mucinous ovarian tumor, uterine cancer, mesothelioma, uterus sarcoma, nasal and paranasal sinus cancer, rhabdoid tumor, and thoracic cavity sarcoma. Preferred is pulmonary adenocarcinoma.

"SMARCA2/A4 deficient cancer" is cancer with deficiency of SMARCA2 and SMARCA4 genes, and/or lack of or attenuation of expression of SMARCA2 and SMARCA4 proteins. Preferably, this is cancer with deficiency of SMARCA2 and SMARCA4 genes, and/or lack of expression of SMARCA2 and SMARCA4 proteins. More preferably, this is cancer with deficiency of SMARCA2 and SMARCA4 genes. Specific examples thereof include pulmonary adenocarcinoma, pleomorphic carcinoma, large cell lung carcinoma, esophageal cancer, gastroesophageal junction cancer, thoracic sarcoma, small cell carcinoma of the ovary, primary gallbladder tumor, uterus sarcoma, malignant rhabdoid tumor, ovarian granulosa tumor, adrenocortical cancer, and small cell lung cancer. Preferred is pulmonary adenocarcinoma.

"ARID deficient cancer" is cancer with deficiency of an ARID gene, and/or lack of or attenuation of expression of an ARID protein. Preferably, this is cancer with deficiency of an ARID gene, and/or lack of expression of an ARID protein. More preferably, this is cancer with deficiency of an ARID1A gene, ARID1B gene or ARID1A/1B gene. Specific examples thereof include ovarian cancer, gastric cancer, bile duct cancer, pancreatic cancer, uterine cancer, neuroblastoma, colon cancer, bladder cancer, liver cancer, melanoma, breast cancer, medulloblastoma, and neuroblastoma. Preferred is ovarian cancer.

"ARID1A deficient cancer" is cancer with deficiency of an ARID1A gene, and/or lack of or attenuation of expression of an ARID1A protein. Preferably, this is cancer with deficiency of an ARID1A gene, and/or lack of expression of an ARID1A protein. More preferably, this is cancer with deficiency of an ARID1A gene. Specific examples thereof include ovarian cancer, gastric cancer, bile duct cancer, pancreatic cancer, uterine cancer, neuroblastoma, colon cancer, and bladder cancer. Preferred is ovarian cancer.

"ARID1B deficient cancer" is cancer with deficiency of an ARID1B gene, and/or lack of or attenuation of expression of an ARID1B protein. Preferably, this is cancer with deficiency of an ARID1B gene, and/or lack of expression of an ARID1B protein. More preferably, this is cancer with deficiency of an ARID1B gene. Specific examples thereof include ovarian cancer, colon cancer, pancreatic cancer, liver cancer, melanoma, breast cancer, medulloblastoma, uterine cancer, bladder cancer, and gastric cancer. Preferred is ovarian cancer.

"ARID1A/1B deficient cancer" is cancer with deficiency of ARID1A and ARID1B genes, and/or lack of or attenuation of expression of ARID1A and ARID1B proteins. Preferably, this is cancer with deficiency of ARID1A and ARID1B genes, and/or lack of expression of ARID1A and ARID1B proteins. More preferably, this is cancer with deficiency of ARID1A and ARID1B genes. Specific examples thereof include ovarian cancer, colon cancer, uterine cancer, neuroblastoma, bladder cancer, and gastric cancer. Preferred is ovarian cancer.

"SS18-SSX fusion cancer" is cancer wherein a SS18 gene is fused to an SSX gene. Specific examples thereof include synovial sarcoma, and Ewing sarcoma. Preferred is synovial sarcoma.

"Cardiac disease" is a disease caused by some disorder of the heart, which results in a failure of blood circulation. Specific examples thereof include cardiomyopathy, heart failure, and myocardial infarction.

"Metabolic disease" is a disease caused by disturbances in the functioning of the metabolism. Specific examples thereof include dyslipidemia, and diabetes.

The dosing period of the compound of the present disclosure and an additional drug is not limited. They can be administered simultaneously or separately to a target of administration. The compound of the present disclosure and an additional drug can also be prepared as a combination drug. The amount of additional drug to be administered can be appropriately selected based on clinically used doses. The blend ratio of the compound of the present disclosure and an additional drug can be appropriately selected depending on the subject of administration, route of administration, target disease, symptom, combination, or the like. If, for example, the subject of administration is a human, 0.01 to 100 parts by weight of additional drug can be used with respect to 1 part by weight of the compound of the present disclosure. They can also be used in combination with an agent (additional drug) such as an antiemetic, sleep inducing agent, or anticonvulsive in order to suppress side effects thereof.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present disclosure has been described while showing preferred embodiments to facilitate understanding. While the present disclosure is described hereinafter based on the Examples, the above descriptions and the following Examples are provided for the sole purpose of exemplification, not limitation of the present disclosure. Thus, the scope of the present disclosure is not limited to the embodiments and Examples that are specifically described herein and is limited only by the scope of claims.

SEQ ID NO 1

```
MAENLLDGPPNPKRAKLSSPGFSANDSTDFGSLFDLENDLPDELI

PNGGELGLLNSGNLVPDAASKHKQLSELLRGGSGSSINPGIGNVS

ASSPVQQGLGGQAQGQPNSANMASLSAMGKSPLSQGDSSAPSLPK

QAASTSGPTPAASQALNPQAQKQVGLATSSPATSQTGPGICMNAN

FNQTHPGLLNSNSGHSLINQASQGQAQVMNGSLGAAGRGRGAGMP

YPTPAMQGASSSVLAETLTQVSPQMTGHAGLNTAQAGGMAKMGIT

GNTSPFGQPFSQAGGQPMGATGVNPQLASKQSMVNSLPTFPTDIK

NTSVTNVPNMSQMQTSVGIVPTQAIATGPTADPEKRKLIQQQLVL

LLHAHKCQRREQANGEVRACSLPHCRTMKNVLNHMTHCQAGKACQ

VAHCASSRQIISHWKNCTRHDCPVCLPLKNASDKRNQQTILGSPA

SGIQNTIGSVGTGQQNATSLSNPNPIDPSSMQRAYAALGLPYMNQ

PQTQLQPQVPGQQPAQPQTHQQMRTLNPLGNNPMNIPAGGITTDQ

QPPNLISESALPTSLGATNPLMNDGSNSGNIGTLSTIPTAAPPSS

TGVRKGWHEHVTQDLRSHLVHKLVQAIFPTPDPAALKDRRMENLV

AYAKKVEGDMYESANSRDEYYHLLAEKIYKIQKELEEKRRSRLHK

QGILGNQPALPAPGAQPPVIPQAQPVRPPNGPLSLPVNRMQVSQG

MNSFNPMSLGNVQLPQAPMGPRAASPMNHSVQMNSMGSVPGMAIS

PSRMPQPPNMMGAHTNNMMAQAPAQSQFLPQNQFPSSSGAMSVGM

GQPPAQTGVSQGQVPGAALPNPLNMLGPQASQLPCPPVTQSPLHP

TPPPASTAAGMPSLQHTTPPGMTPPQPAAPTQPSTPVSSSGQTPT

PTPGSVPSATQTQSTPTVQAAAQAQVTPQPQTPVQPPSVATPQSS

QQQPTPVHAQPPGTPLSQAAASIDNRVPTPSSVASAETNSQQPGP

DVPVLEMKTETQAEDTEPDPGESKGEPRSEMMEEDLQGASQVKEE

TDIAEQKSEPMEVDEKKPEVKVEVKEEEESSSNGTASQSTSPSQP

RKKIFKPEELRQALMPTLEALYRQDPESLPFRQPVDPQLLGIPDY

FDIVKNPMDLSTIKRKLDTGQYQEPWQYVDDVWLMENNAWLYNRK

TSRVYKFCSKLAEVFEQEIDPVMQSLGYCCGRKYEFSPQTLCCYG

KQLCTIPRDAAYYSYQNRYHFCEKCFTEIQGENVTLGDDPSQPQT

TISKDQFEKKKNDTLDPEPFVDCKECGRKMHQICVLHYDIIWPSG

FVCDNCLKKTGRPRKENKFSAKRLQTTRLGNHLEDRVNKFLRRQN

HPEAGEVFVRVVASSDKTVEVKPGMKSRFVDSGEMSESFPYRTKA

LFAFEEIDGVDVCFFGMHVQEYGSDCPPPNTRRVYISYLDSIHFF

RPRCLRTAVYHEILIGYLEYVKKLGYVTGHIWACPPSEGDDYIFH

CHPPDQKIPKPKRLQEWYKKMLDKAFAERIIHDYKDIFKQATEDR

LTSAKELPYFEGDFWPNVLEESIKELEQEEEERKKEESTAASETT

EGSQGDSKNAKKKNNKKTNKNKSSISRANKKKPSMPNVSNDLSQK

LYATMEKHKEVFFVIHLHAGPVINTLPPIVDPDPLLSCDLMDGRD

AFLTLARDKHWEFSSLRRSKWSTLCMLVELHTQGQDRFVYTCNEC

KHHVETRWHCTVCEDYDLCINCYNTKSHAHKMVKWGLGLDDEGSS

QGEPQSKSPQESRRLSIQRCIQSLVHACQCRNANCSLPSCQKMKR
```

-continued

VVQHTKGCKRKINGGCPVCKQLIALCCYHAKHCQENKCPVPFCLN
IKHKLRQQQIQHRLQQAQLMRRRMATMNTRNVPQQSLPSPTSAPP
GTPTQQPSTPQTPQPPAQPQPSPVSMSPAGFPSVARTQPPTTVST
GKPTSQVPAPPPPAQPPPAAVEAARQIEREAQQQQHLYRVNINNS
MPPGRTGMGTPGSQMAPVSLNVPRPNQVSGPVMPSMPPGQWQQAP
LPQQQPMPGLPRPVISMQAQAAVAGPRMPSVQPPRSISPSALQDL
LRTLKSPSSPQQQQQVLNILKSNPQLMAAFIKQRTAKYVANQPGM
QPQPGLQSQPGMQPQPGMHQQPSLQNLNAMQAGVPRPGVPPQQQA
MGGLNPQGQALNIMNPGHNPNMASMNPQYREMLRRQLLQQQQQQQ
QQQQQQQQQQQGSAGMAGGMAGHGQFQQPQGPGGYPPAMQQQQRM
QQHLPLQGSSMGQMAAQMGQLGQMGQPGLGADSTPNIQQALQQRI
LQQQQMKQQIGSPGQPNPMSPQQHMLSGQPQASHLPGQQIATSLS
NQVRSPAPVQSPRPQSQPPHSSPSPRIQPQPSPHHVSPQTGSPHP
GLAVTMASSIDQGHLGNPEQSAMLPQLNTPSRSALSSELSLVGDT
TGDTLEKFVEGL

SEQ ID NO 2

MAENLLDGPPNPKRAKLSSPGFSANDSTDFGSLFDLENDLPDELI
PNGGELGLLNSGNLVPDAASKHKQLSELLRGGSGSSINPGIGNVS
ASSPVQQGLGGQAQGQPNSANMASLSAMGKSPLSQGDSSAPSLPK
QAASTSGPTPAASQALNPQAQKQVGLATSSPATSQTGPGICMNAN
FNQTHPGLLNSNSGHSLINQASQGQAQVMNGSLGAAGRGRGAGMP
YPTPAMQGASSSVLAETLTQVSPQMTGHAGLNTAQAGGMAKMGIT
GNTSPFGQPFSQAGGQPMGATGVNPQLASKQSMVNSLPTFPTDIK
NTSVTNVPNMSQMQTSVGIVPTQAIATGPTADPEKRKLIQQQLVL
LLHAHKCQRREQANGEVRACSLPHCRTMKNVLNHMTHCQAGKACQ
AILGSPASGIQNTIGSVGTGQQNATSLSNPNPIDPSSMQRAYAAL
GLPYMNQPQTQLQPQVPGQQPAQPQTHQQMRTLNPLGNNPMNIPA
GGITTDQQPPNLISESALPTSLGATNPLMNDGSNSGNIGTLSTIP
TAAPPSSTGVRKGWHEHVTQDLRSHLVHKLVQAIFPTPDPAALKD
RRMENLVAYAKKVEGDMYESANSRDEYYHLLAEKIYKIQKELEEK
RRSRLHKQGILGNQPALPAPGAQPPVIPQAQPVRPPNGPLSLPVN
RMQVSQGMNSFNPMSLGNVQLPQAPMGPRAASPMNHSVQMNSMGS
VPGMAISPSRMPQPPNMMGAHTNNMMAQAPAQSQFLPQNQFPSSS
GAMSVGMGQPPAQTGVSQGQVPGAALPNPLNMLGPQASQLPCPPV
TQSPLHPTPPPASTAAGMPSLQHTTPPGMTPPQPAAPTQPSTPVS
SSGQTPTPTPGSVPSATQTQSTPTVQAAAQAQVTPQPQTPVQPPS
VATPQSSQQQPTPVHAQPPGTPLSQAAASIDNRVPTPSSVASAET
NSQQPGPDVPVLEMKTETQAEDTEPDPGESKGEPRSEMMEEDLQG
ASQVKEETDIAEQKSEPMEVDEKKPEVKVEVKEEEESSSNGTASQ
STSPSQPRKKIFKPEELRQALMPTLEALYRQDPESLPFRQPVDPQ
LLGIPDYFDIVKNPMDLSTIKRKLDTGQYQEPWQYVDDVWLMENN

-continued

AWLYNRKTSRVYKFCSKLAEVFEQEIDPVMQSLGYCCGRKYEFSP
QTLCCYGKQLCTIPRDAAYYSYQNRYHFCEKCFTEIQGENVTLGD
DPSQPQTTISKDQFEKKKNDTLDPEPFVDCKECGRKMHQICVLHY
DIIWPSGFVCDNCLKKTGRPRKENKFSAKRLQTTRLGNHLEDRVN
KFLRRQNHPEAGEVFVRVVASSDKTVEVKPGMKSRFVDSGEMSES
FPYRTKALFAFEEIDGVDVCFFGMHVQEYGSDCPPPNTRRVYISY
LDSIHFFRPRCLRTAVYHEILIGYLEYVKKLGYVTGHIWACPPSE
GDDYIFHCHPPDQKIPKPKRLQEWYKKMLDKAFAERIIHDYKDIF
KQATEDRLTSAKELPYFEGDFWPNVLEESIKELEQEEEERKKEES
TAASETTEGSQGDSKNAKKKNNKKTNKNKSSISRANKKKPSMPNV
SNDLSQKLYATMEKHKEVFFVIHLHAGPVINTLPPIVDPDPLLSC
DLMDGRDAFLTLARDKHWEFSSLRRSKWSTLCMLVELHTQGQDRF
VYTCNECKHHVETRWHCTVCEDYDLCINCYNTKSHAHKMVKWGLG
LDDEGSSQGEPQSKSPQESRRLSIQRCIQSLVHACQCRNANCSLP
SCQKMKRVVQHTKGCKRKTNGGCPVCKQLIALCCYHAKHCQENKC
PVPFCLNIKHKLRQQQIQHRLQQAQLMRRRMATMNTRNVPQQSLP
SPTSAPPGTPTQQPSTPQTPQPPAQPQPSPVSMSPAGFPSVARTQ
PPTTVSTGKPTSQVPAPPPPAQPPPAAVEAARQIEREAQQQQHLY
RVNINNSMPPGRTGMGTPGSQMAPVSLNVPRPNQVSGPVMPSMPP
GQWQQAPLPQQQPMPGLPRPVISMQAQAAVAGPRMPSVQPPRSIS
PSALQDLLRTLKSPSSPQQQQQVLNILKSNPQLMAAFIKQRTAKY
VANQPGMQPQPGLQSQPGMQPQPGMHQQPSLQNLNAMQAGVPRPG
VPPQQQAMGGLNPQGQALNIMNPGHNPNMASMNPQYREMLRRQLL
QQQQQQQQQQQQQQQQQQGSAGMAGGMAGHGQFQQPQGPGGYPPA
MQQQQRMQQHLPLQGSSMGQMAAQMGQLGQMGQPGLGADSTPNIQ
QALQQRILQQQQMKQQIGSPGQPNPMSPQQHMLSGQPQASHLPGQ
QIATSLSNQVRSPAPVQSPRPQSQPPHSSPSPRIQPQPSPHHVSP
QTGSPHPGLAVTMASSIDQGHLGNPEQSAMLPQLNTPSRSALSSE
LSLVGDTTGDTLEKFVEGL

SEQ ID NO 3

MAENVVEPGPPSAKRPKLSSPALSASASDGTDFGSLFDLEHDLPD
ELINSTELGLINGGDINQLQTSLGMVQDAASKHKQLSELLRSGSS
PNLNMGVGGPGQVMASQAQQSSPGLGLINSMVKSPMTQAGLTSPN
MGMGTSGPNQGPTQSTGMMNSPVNQPAMGMNTGMNAGMNPGMLAA
GNGQGIMPNQVMNGSIGAGRGRQNMQYPNPGMGSAGNLLTEPLQQ
GSPQMGGQTGLRGPQPLKMGMMNNPNPYGSPYTQNPGQQIGASGL
GLQIQTKTVLSNNLSPFAMDKKAVPGGGMPNMGQQPAPQVQQPGL
VTPVAQGMGSGAHTADPEKRKLIQQQLVLLLHAHKCQRREQANGE
VRQCNLPHCRTMKNVLNHMTHCQSGKSCQVAHCASSRQIISHWKN
CTRHDCPVCLPLKNAGDKRNQQPILTGAPVGLGNPSSLGVGQQSA
PNLSTVSQIDPSSIERAYAALGLPYQVNQMPTQPQVQAKNQQNQQ

-continued

PGQSPQGMRPMSNMSASPMGVNGGVGVQTPSLLSDSMLHSAINSQ

NPMMSENASVPSLGPMPTAAQPSTTGIRKQWHEDITQDLRNHLVH

KLVQAIFPTPDPAALKDRRMENLVAYARKVEGDMYESANNRAEYY

HLLAEKIYKIQKELEEKRRTRLQKQNMLPNAAGMVPVSMNPGPNM

GQPQPGMTSNGPLPDPSMIRGSVPNQMMPRITPQSGLNQFGQMSM

AQPPIVPRQTPPLQHHGQLAQPGALNPPMGYGPRMQQPSNQGQFL

PQTQFPSQGMNVTNIPLAPSSGQAPVSQAQMSSSSCPVNSPIMPP

GSQGSHIHCPQLPQPALHQNSPSPVPSRTPTPHHTPPSIGAQQPP

ATTIPAPVPTPPAMPPGPQSQALHPPPRQTPTPPTTQLPQQVQPS

LPAAPSADQPQQQPRSQQSTAASVPTPTAPLLPPQPATPLSQPAV

SIEGQVSNPPSTSSTEVNSQAIAEKQPSQEVKMEAKMEVDQPEPA

DTQPEDISESKVEDCKMESTETEERSTELKTEIKEEEDQPSTSAT

QSSPAPGQSKKKIFKPEELRQALMPTLEALYRQDPESLPFRQPVD

PQLLGIPDYFDIVKSPMDLSTIKRKLDTGQYQEPWQYVDDIWLME

NNAWLYNRKTSRVYKYCSKLSEVFEQEIDPVMQSLGYCCGRKLEF

SPQTLCCYGKQLCTIPRDATYYSYQNRYHFCEKCFNEIQGESVSL

GDDPSQPQTTINKEQFSKRKNDTLDPELFVECTECGRKMHQICVL

HHEIIWPAGFVCDGCLKKSARTRKENKFSAKRLPSTRLGTFLENR

VNDFLRRQNHPESGEVTVRVVHASDKTVEVKPGMKARFVDSGEMA

ESFPYRTKALFAFEEIDGVDLCFFGMHVQEYGSDCPPPNQRRVYI

SYLDSVHFFRPKCLRTAVYHEILIGYLEYVKKLGYTTGHIWACPP

SEGDDYIFHCHPPDQKIPKPKRLQEWYKKMLDKAVSERIVHDYKD

IFKQATEDRLTSAKELPYFEGDFWPNVLEESIKELEQEEEERKRE

ENTSNESTDVTKGDSKNAKKKNNKKTSKNKSSLSRGNKKKPGMPN

VSNDLSQKLYATMEKHKEVFFVIRLIAGPAANSLPPIVDPDPLIP

CDLMDGRDAFLTLARDKHLEFSSLRRAQWSTMCMLVELHTQSQDR

FVYTCNECKHHVETRWHCTVCEDYDLCITCYNTKNHDHKMEKLGL

GLDDESNNQQAAATQSPGDSRRLSIQRCIQSLVHACQCRNANCSL

PSCQKMKRVVQHTKGCKRKTNGGCPICKQLIALCCYHAKHCQENK

CPVPFCLNIKQKLRQQQLQHRLQQAQMLRRRMASMQRTGVVGQQQ

GLPSPTPATPTTPTGQQPTTPQTPQPTSQPQPTPPNSMPPYLPRT

QAAGPVSQGKAAGQVTPPTPPQTAQPPLPGPPPAAVEMAMQIQRA

AETQRQMAHVQIFQRPIQHQMPPMTPMAPMGMNPPPMTRGPSGHL

EPGMGPTGMQQQPPWSQGGLPQPQQLQSGMPRPAMMSVAQHGQPL

NMAPQPGLGQVGISPLKPGTVSQQALQNLLRTLRSPSSPLQQQQV

LSILHANPQLLAAFIKQRAAKYANSNPQPIPGQPGMPQGQPGLQP

PTMPGQQGVHSNPAMQNMNPMQAGVQRAGLPQQQPQQQLQPPMGG

MSPQAQQMNMNHNTMPSQFRDILRRQQMMQQQQQQGAGPGIGPGM

ANHNQFQQPQGVGYPPQQQQRMQHHMQQMQQGNMGQIGQLPQALG

AEAGASLQAYQQRLLQQQMGSPVQPNPMSPQQHMLPNQAQSPHLQ

GQQIPNSLSNQVRSPQPVPSPRPQSQPPHSSPSPRMQPQPSPHHV

-continued

SPQTSSPHPGLVAAQANPMEQGHFASPDQNSMLSQLASNPGMANL

HGASATDLGLSTDNSDLNSNLSQSTLDIH

Example

The present disclosure is described more specifically with the Reference Examples, Examples, and Test Example hereinafter, but the present disclosure is not limited thereto.

The present specification may use the following abbreviations.

Me: methyl

Et: ethyl

Ph: phenyl

Bn: benzyl

Boc: tert-butoxycarbonyl

DMPU: N,N'-dimethylpropylene urea n-: normaltert-: tertiaryp-: para-

Ac: acetyl dppf: 1,1'-bis(diphenylphosphino)ferrocene

XPHOS: 2-dicyclohexylphosphino-2',4',6'-triisopropylbiphenyl

NMR (Nuclear Magnetic Resonance) data used for identifying a compound was obtained with JNM-ECS 400 NMR spectrometer (400 MHz) (JEOL Ltd.)

As symbols used in NMR, s refers to singlet, d refers to doublet, dd refers to doublet of doublets, t refers to triplet, td refers to doublet of triplets, q refers to quartet, m refers to multiplet, br refers to broad, brs refers to broad singlet, brm refers to broad multiplet, and J refers to a coupling constant.

LC/MS (Liquid Chromatography-Mass Spectrometry) analysis conditions used in identification of compounds are as follows. Among the observed mass spectrometry values [MS (m/z)], a value corresponding to monoisotopic mass (precise mass consisting of only the primary isotope) is indicated by $[M+H]^+$, $[M-H]^-$ or $[M+2H]^{2+}$, or the like, and the time of retention is indicated by Rt (minutes).

LC/MS Measurement Method:

Detector: ACQUITY (registered trademark) SQ detector (Waters)

HPLC: ACQUITY UPLC (registered trademark) system

Column: Waters ACQUITY UPLC (registered trademark) BEH C18 (1.7 μm, 2.1 mm×30 mm)

Solvent: solution A: 0.06% formic acid/$H_2O$, solution B: 0.06% formic acid/MeCN Gradient condition: 0.0-1.3 min Linear gradient from B 2% to 96%

Flow rate: 0.8 mL/min

UV: 220 nm and 254 nm

Column temperature: 40° C.

Reference Example 1

N-(4-fluorobenzyl)-2-hydroxy-N-(3-(trifluoromethyl)oxetan-3-yl) acetamide

[Chemical Formula 26]

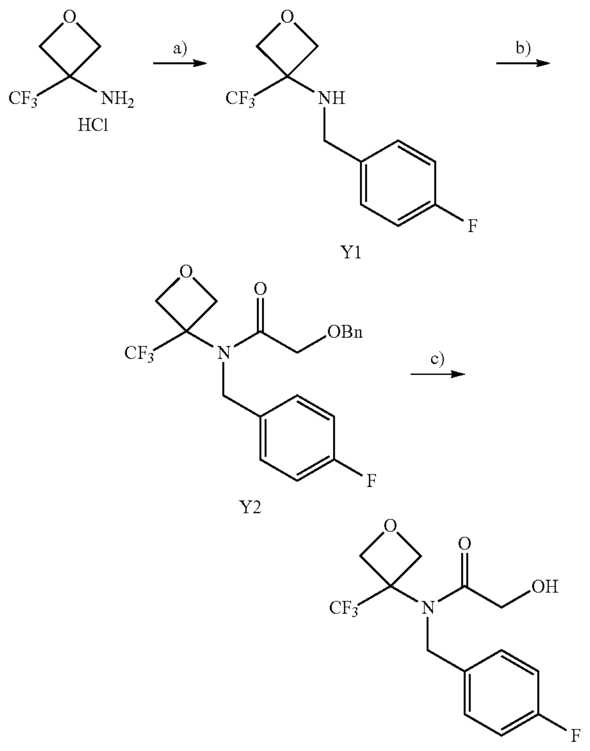

a) Production of N-(4-fluorobenzyl)-3-(trifluoromethyl)oxetan-3-amine (Compound Y1)

3-(Trifluoromethyl)oxetan-3-amine hydrochloride (10.0 g) was dissolved in chloroform (188 mL), 4-fluorobenzaldehyde (7.25 mL) and sodium triacetoxyborohydride (22.4 g) were added at 0° C., and the mixture was stirred at room temperature for 16 hr. To the reaction mixture was added water, and the mixture was subjected to extraction twice with chloroform. The obtained organic layer was washed with saturated brine, and dried over magnesium sulfate. It was removed by filtration, and the solvent was evaporated under reduced pressure. The residue was purified by silica gel column chromatography (hexane/ethyl acetate) to give the title compound (10.6 g). LC-MS ($[M+H]^+$/Rt(min)): 250.1/0.936 b) Production of 2-(benzyloxy)-N-(4-fluorobenzyl)-N-(3-(trifluoromethyl)oxetan-3-yl) acetamide (Compound Y2)

Compound Y1 (7.6 g) was dissolved in DMPU (102 mL), sodium hydride (2.0 g) was added at 0° C., and the mixture was stirred at room temperature for 30 min. Benzyloxyacetyl chloride (12.0 mL) was added at 0° C., and the mixture was stirred at room temperature for 5 hr. To the reaction mixture was added water, and the mixture was subjected to extraction twice with ethyl acetate. The obtained organic layer was washed with saturated brine, and dried over magnesium sulfate. It was removed by filtration, and the solvent was evaporated under reduced pressure. The residue was purified by silica gel column chromatography (hexane/ethyl acetate) to give the title compound (10.8 g).

LC-MS ($[M+H]^+$/Rt(min)): 398.2/1.034 c) Production of N-(4-fluorobenzyl)-2-hydroxy-N-(3-(trifluoromethyl)oxetan-3-yl)acetamide Compound Y2 (15.1 g) was dissolved in methanol (127 mL), palladium hydroxide-activated carbon (2.1 g) was added, and the mixture was stirred under hydrogen atmosphere at room temperature for 4 hr. The mixture was filtered through Celite, the residue was washed with methanol, and the solvent was evaporated under reduced pressure. The residue was purified by silica gel column chromatography (hexane/ethyl acetate) to give the title compound (11.0 g).

LC-MS ($[M+H]^+$/Rt(min)): 308.1/0.745

Reference Examples 2 to 5

The compounds of Reference Examples 2 to 6 were obtained using the corresponding raw material compound according the method described in Reference Example 1.

TABLE 1-1

| Reference Example | Chemical structural formula | LC-MS ([M + H] +/Rt (min)) |
|---|---|---|
| 2 | 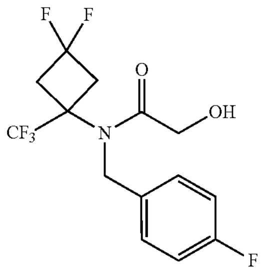 [SMILES: O=C(CO)N(Cc1ccc(F)cc1)C1(C(F)(F)F)CC(F)(F)C1] | 342.1/0.876 |
| 3 | 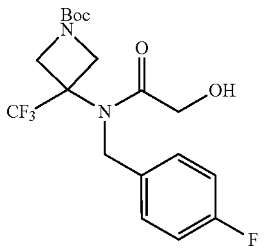 [SMILES: CC(C)(C)OC(=O)N1CC(N(Cc2ccc(F)cc2)C(=O)CO)(C(F)(F)F)C1] | 407.3/0.947 |
| 4 | 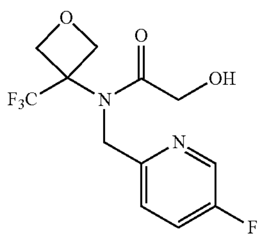 [SMILES: O=C(CO)N(Cc1ccc(F)cn1)C1(C(F)(F)F)COC1] | 309.2/0.577 |

TABLE 1-2

| | | |
|---|---|---|
| 5 | 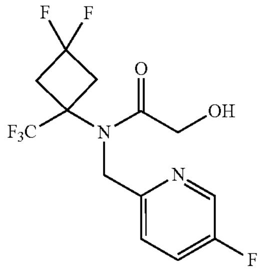 [SMILES: O=C(CO)N(Cc1ccc(F)cn1)C1(C(F)(F)F)CC(F)(F)C1] | 344.1/0.804 |
| 6 | 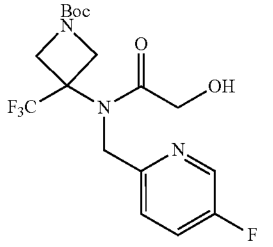 [SMILES: CC(C)(C)OC(=O)N1CC(N(Cc2ccc(F)cn2)C(=O)CO)(C(F)(F)F)C1] | 408.2/0.900 |
| 7 | 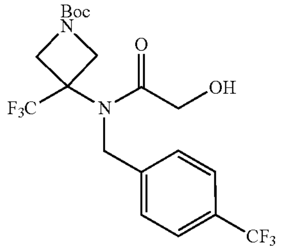 [SMILES: CC(C)(C)OC(=O)N1CC(N(Cc2ccc(C(F)(F)F)cc2)C(=O)CO)(C(F)(F)F)C1] | 401.2/1.058 |

Reference Example 8

(3'R,4S)-5'-bromo-3'-fluoro-2',3'-dihydrospiro[imidazolidine-4,1'-indene]-2,5-dione

[Chemical Formula 27]

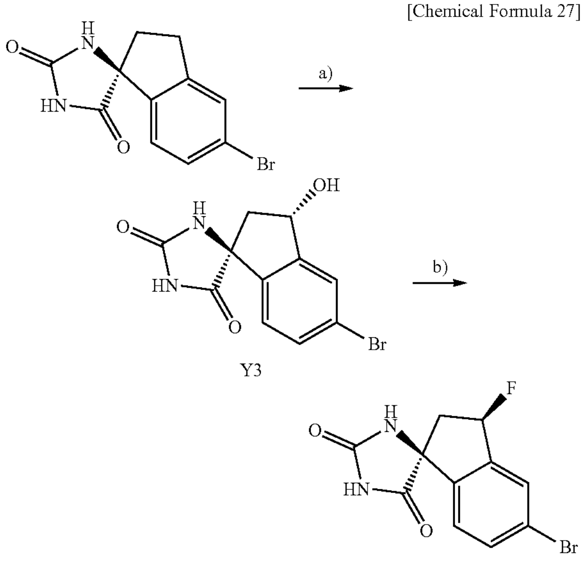

a) Production of (3'S,4S)-5'-bromo-3'-hydroxy-2',3'-dihydrospiro[imidazolidine-4,1'-indene]-2,5-dione (Compound Y3)

(4S)-5'-Bromospiro(imidazolidine-4,1'-indene)-2,3',5 (2'H)-trione (20.0 g) was dissolved in methanol (339 mL), sodium borohydride (2.8 g) was added at −78° C., and the mixture was stirred at 0° C. for 1 hr. To the reaction mixture was added saturated ammonium chloride aqueous solution at 0° C. The reaction mixture was subjected to extraction twice with a mixture of ethyl acetate/methanol. The obtained organic layer was washed with saturated brine, and dried over magnesium sulfate. It was removed by filtration, and the solvent was evaporated under reduced pressure to give the title compound (19.0 g).

LC-MS ($[M+H]^+$/Rt (min)): 297.0/0.529 b) Production of (3'R,4S)-5'-bromo-3'-fluoro-2',3'-dihydrospiro[imidazolidine-4,1'-indene]-2,5-dione Compound Y3 (18.6 g) was dissolved in dichloromethane (313 mL), (diethylamino)sulfur trifluoride (28.9 mL) was added at −78° C., and the mixture was stirred at 0° C. for 2 hr. To the reaction mixture was added saturated sodium hydrogencarbonate aqueous solution at 0° C. The reaction mixture was subjected to extraction twice with ethyl acetate. The obtained organic layer was washed with saturated brine, and dried over magnesium sulfate. It was removed by filtration, and the solvent was evaporated under reduced pressure. The residue was purified by silica gel column chromatography (chloroform/methanol) to give the title compound (15.6 g).

LC-MS ($[M+H]^+$/Rt (min)): 299.0/0.681

Reference Example 9

(S)-2-(5'-bromo-2,5-dioxo-2',3'-dihydrospiro[imidazolidine-4,1'-inden]-1-yl)-N-(4-fluorobenzyl)-N-(3-(trifluoromethyl)oxetan-3-yl)acetamide

[Chemical Formula 28]

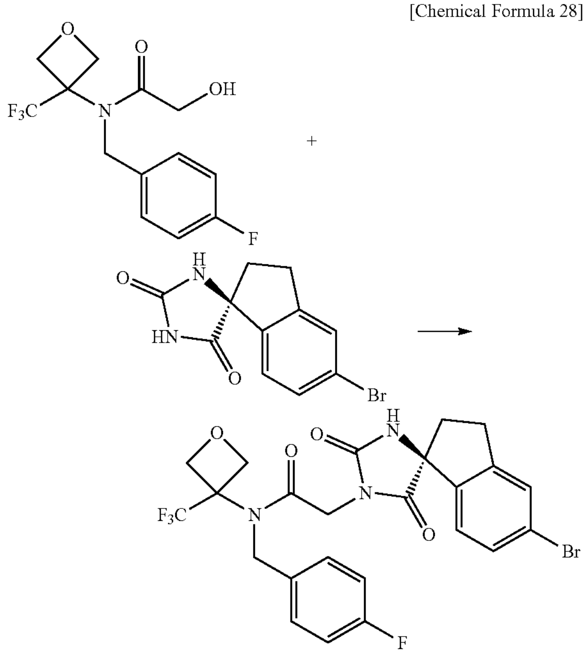

The compound (264 mg) of Reference Example 1 was dissolved in tetrahydrofuran (3 mL), (S)-5'-bromo-2',3'-dihydrospiro(imidazolidine-4,1'-indene)-2,5-dione (230 mg), diisopropyl azodicarboxylate (0.56 mL) and triphenylphosphine (279 mg) were added at 0° C., and the mixture was stirred at room temperature for 1 hr. To the reaction mixture was added water, and the mixture was subjected to extraction twice with ethyl acetate. The obtained organic layer was washed with saturated brine, and dried over magnesium sulfate. It was removed by filtration, and the solvent was evaporated under reduced pressure. The residue was purified by silica gel column chromatography (hexane/ethyl acetate) to give the title compound (460 mg).

LC-MS ([M+H]$^+$/Rt (min)): 572.3/1.038

Reference Examples 10 to 16

The compounds of Reference Examples 10 to 16 were obtained using the corresponding raw material compound according to the method described in Reference Example 9.

TABLE 2-1

| Reference Example | Raw material compound | Chemical structural formula | LC-MS ([M + H]+/Rt (min)) |
|---|---|---|---|
| 10 | Reference Example 2 | 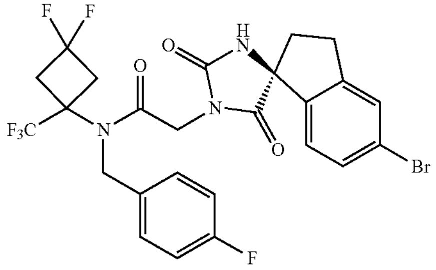 [SMILES: O=C1N[C@]2(CCc3cc(Br)ccc32)C(=O)N1CC(=O)N(Cc1ccc(F)cc1)C1(C(F)(F)F)CC(F)(F)C1] | 604.2/1.135 |
| 11 | Reference Example 4 | 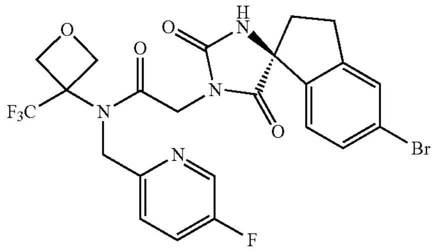 [SMILES: O=C1N[C@]2(CCc3cc(Br)ccc32)C(=O)N1CC(=O)N(Cc1ccc(F)cn1)C1(C(F)(F)F)COC1] | 573.3/0.957 |
| 12 | Reference Example 5 | 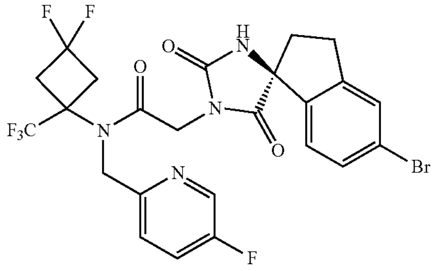 [SMILES: O=C1N[C@]2(CCc3cc(Br)ccc32)C(=O)N1CC(=O)N(Cc1ccc(F)cn1)C1(C(F)(F)F)CC(F)(F)C1] | 605.2/1.075 |
| 13 | Reference Example 1 Reference Example 8 | 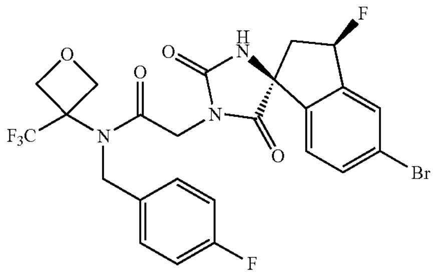 [SMILES: O=C1N[C@]2(C[C@@H](F)c3cc(Br)ccc32)C(=O)N1CC(=O)N(Cc1ccc(F)cc1)C1(C(F)(F)F)COC1] | 588.2/1.036 |

TABLE 2-2

| | | | |
|---|---|---|---|
| 14 | Reference Example 2 Reference Example 8 | 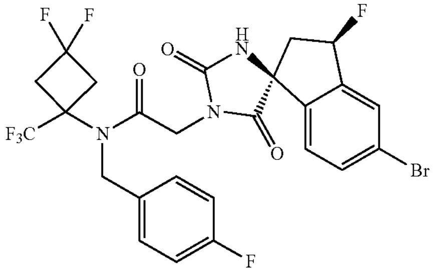 [SMILES: O=C1N[C@]2(C[C@@H](F)c3cc(Br)ccc32)C(=O)N1CC(=O)N(Cc1ccc(F)cc1)C1(C(F)(F)F)CC(F)(F)C1] | 622.3/1.136 |
| 15 | Reference Example 4 Reference Example 8 | 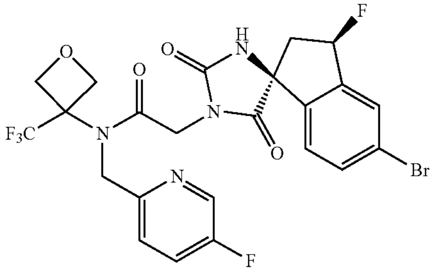 [SMILES: O=C1N[C@]2(C[C@@H](F)c3cc(Br)ccc32)C(=O)N1CC(=O)N(Cc1ccc(F)cn1)C1(C(F)(F)F)COC1] | 589.2/0.946 |
| 16 | Reference Example 5 Reference Example 8 | 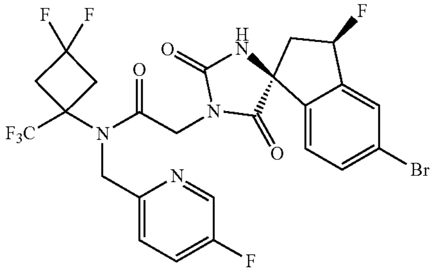 [SMILES: O=C1N[C@]2(C[C@@H](F)c3cc(Br)ccc32)C(=O)N1CC(=O)N(Cc1ccc(F)cn1)C1(C(F)(F)F)CC(F)(F)C1] | 623.2/1.078 |

Reference Example 17

(S)-2-(5'-bromo-2,5-dioxo-2',3'-dihydrospiro[imidazolidine-4,1'-inden]-1-yl) —N-(1-methyl-3-(trifluoromethyl)azetidin-3-yl) acetamide

[Chemical Formula 29]

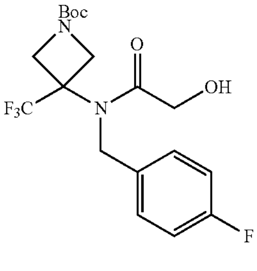

+

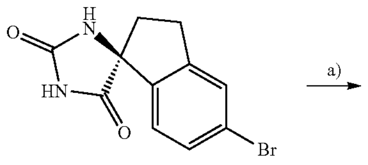

-continued

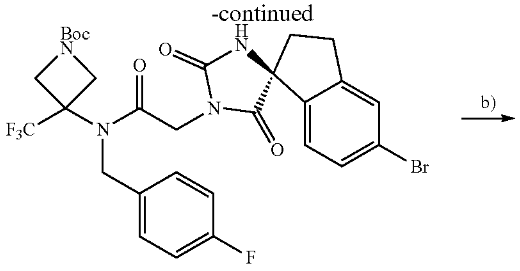

Y4

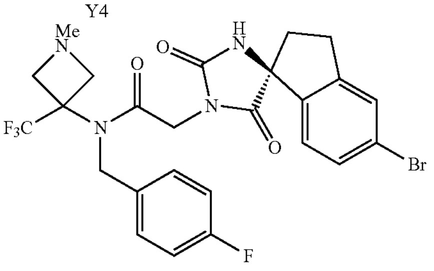

a) The compound (1.83 g) of Reference Example 3 was dissolved in tetrahydrofuran (29 mL), (S)-5'-bromo-2',3'-dihydrospiro(imidazolidine-4,1'-indene)-2,5-dione (1.21 g), bis(2-methoxyethyl) azodicarboxylate (1.3 g) and triphenylphosphine (1.5 g) were added at 0° C., and the mixture was stirred at room temperature for 1 hr. To the reaction mixture was added water, and the mixture was subjected to extraction twice with ethyl acetate. The obtained organic layer was washed with saturated brine, and dried over magnesium sulfate. It was removed by filtration, and the solvent was evaporated under reduced pressure. The residue was purified by silica gel column chromatography (hexane/ethyl acetate) to give the title compound.

LC-MS ([M+H]+/Rt (min)): 615.2/1.178 b) Production of (S)-2-(5'-bromo-2,5-dioxo-2',3'-dihydrospiro[imidazolidine-4,1'-inden]-1-yl)-N-(1-methyl-3-(trifluoromethyl)azetidin-3-yl)acetamide Compound Y4 obtained above was dissolved in chloroform (17 mL), trifluoroacetic acid (13.2 mL) was added at room temperature, and the mixture was stirred for 5 hr. The reaction mixture was concentrated under reduced pressure, and azeotroped with toluene. The obtained crude substance was dissolved in chloroform (21 mL), and 37% formalin aqueous solution (1.4 mL) and sodium triacetoxyborohydride (2.7 g) were added at 0° C., and the mixture was stirred at room temperature for 15 hr. To the reaction mixture was added saturated sodium hydrogencarbonate aqueous solution at 0° C. The reaction mixture was subjected to extraction twice with chloroform. The obtained organic layer was washed with saturated brine, and dried over magnesium sulfate. It was removed by filtration, and the solvent was evaporated under reduced pressure. The residue was purified by amino silica gel column chromatography (hexane/ethyl acetate) to give the title compound (1.16 g).

LC-MS ([M+H]+/Rt (min)): 583.3/0.778

Reference Examples 18 to 22

The compounds of Reference Examples 18 to 22 were obtained using the corresponding raw material compound according to the method described in Reference Example 17.

TABLE 3

| Reference Example | Raw material compound | Chemical structural formula | LC-MS ([M + H]+/Rt (min)) |
|---|---|---|---|
| 18 | Reference Example 6 | 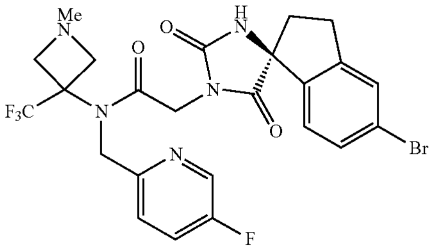 [SMILES: CN1CC(N(Cc2ccc(F)cn2)C(=O)CN2C(=O)N[C@]3(CCc4cc(Br)ccc43)C2=O)(C(F)(F)F)C1] | 584.2/0.747 |
| 19 | Reference Example 3 Reference Example 8 | 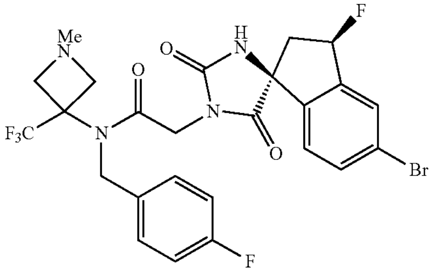 [SMILES: CN1CC(N(Cc2ccc(F)cc2)C(=O)CN2C(=O)N[C@]3(C[C@@H](F)c4cc(Br)ccc43)C2=O)(C(F)(F)F)C1] | 601.1/0.762 |
| 20 | Reference Example 6 Reference Example 8 | 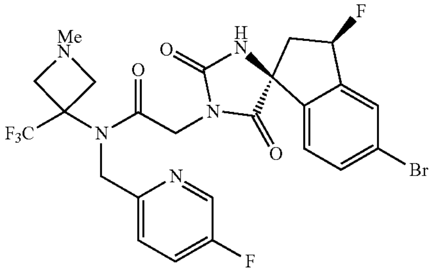 [SMILES: CN1CC(N(Cc2ccc(F)cn2)C(=O)CN2C(=O)N[C@]3(C[C@@H](F)c4cc(Br)ccc43)C2=O)(C(F)(F)F)C1] | 602.2/0.744 |
| 21 | Reference Example 3 | 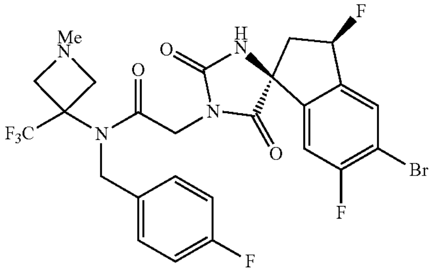 [SMILES: CN1CC(N(Cc2ccc(F)cc2)C(=O)CN2C(=O)N[C@]3(C[C@@H](F)c4cc(Br)c(F)cc43)C2=O)(C(F)(F)F)C1] | 619.1/1.110 |

Example 1

N-[(4-fluorophenyl)methyl]-2-[(1'S)-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]-N-[3-(trifluoromethyl)oxetan-3-yl]acetamide

[Chemical Formula 30]

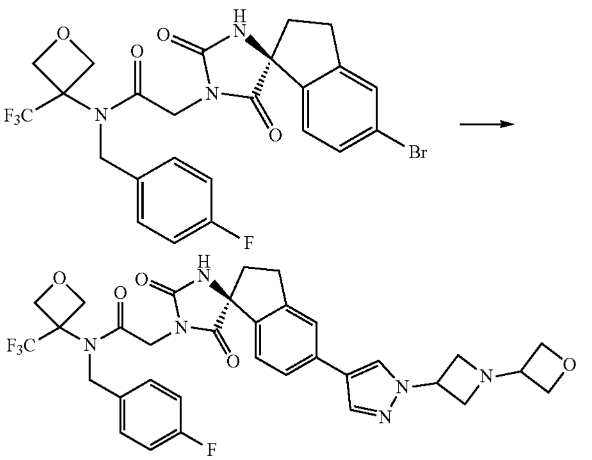

The compound (100 mg) of Reference Example 9 was dissolved in 1,4-dioxane (0.7 mL) and water (0.2 mL), and potassium carbonate (52 mg), 1-(1-(oxetan-3-yl)azetidin-3-yl)-1H-pyrazole-4-boronic acid pinacol ester (68 mg) and [1,1'-bis(diphenylphosphino)ferrocene]palladium(II) dichloride (14 mg) were added at room temperature, and the mixture was stirred at 90° C. for 2 hr. To the reaction mixture was added water, and the mixture was subjected to extraction twice with chloroform. The obtained organic layer was washed with saturated brine, and dried over sodium sulfate. It was removed by filtration, and the solvent was evaporated under reduced pressure. The residue was purified by silica gel column chromatography (ethyl acetate/methanol) to give the title compound (29 mg).

LC-MS ([M+H]$^+$/Rt (min)): 669.5/1.005

Examples 2 to 35

The compounds of Examples 2 to 35 were obtained using the corresponding compound of Reference Examples and commercially available compounds as raw materials, according to the method described in Example 1.

TABLE 4-1

| Example | Raw material compound | Chemical structural formula NMR | LC-MS ([M + H]+/ Rt (min)) |
|---|---|---|---|
| 2 | Reference Example 9 | 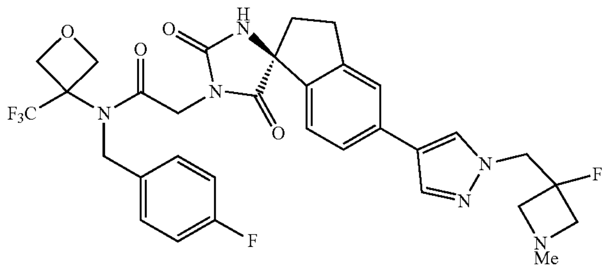 [SMILES: CN1CC(F)(Cn2cc(-c3ccc4c(c3)CC[C@]43NC(=O)N(CC(=O)N(Cc4ccc(F)cc4)C4(C(F)(F)F)COC4)C3=O)cn2)C1] | 659.4/0.990 |
| 3 | Reference Example 13 | 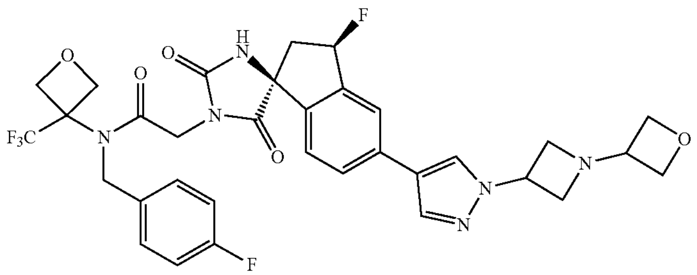 [SMILES: O=C1N[C@]2(C[C@@H](F)c3cc(-c4cnn(C5CN(C6COC6)C5)c4)ccc32)C(=O)N1CC(=O)N(Cc1ccc(F)cc1)C1(C(F)(F)F)COC1] 1H-NMR (400 MHz, DMSO-d6): δ9.01 (1H, s), 8.47 (1H, s), 8.04 (1H, s), 7.79 (1H, s), 7.75 (1H, d, J = 8.0 Hz), 7.47-7.44 (2H, m), 7.31-7.26 (3H, m), 6.22-6.04 (1H, m), 5.06-5.02 (1H, m), 4.78-4.61 (6H, m), 4.60 (2H, t, J = 6.4 Hz), 4.44 (2H, t, J = 5.6 Hz), 4.21-4.11 (2H, m), 3.87-3.81 (1H, m), 3.74 (2H, t, J = 7.6 Hz), 3.55 (2H, t, J = 7.2 Hz), 3.06-2.98 (1H, m), 2.37-2.26 (1H, m). | 687.4/1.664 |

TABLE 4-1-continued

| Example | Raw material compound | Chemical structural formula NMR | LC-MS ([M + H]+/ Rt (min)) |
|---|---|---|---|
| 4 | Reference Example 14 | 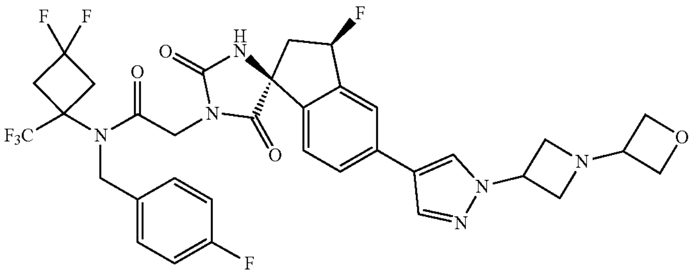 [SMILES: O=C1N[C@]2(C[C@@H](F)c3cc(-c4cnn(C5CN(C6COC6)C5)c4)ccc32)C(=O)N1CC(=O)N(Cc1ccc(F)cc1)C1(C(F)(F)F)CC(F)(F)C1]<br>1H-NMR (400 MHz, DMSO-d6): δ9.03 (1H, s), 8.47 (1H, s), 8.05 (1H, s), 7.80 (1H, s), 7.75 (1H, d, J = 8.0 Hz), 7.39-7.26 (5H, m), 6.23-6.05 (1H, m), 5.08-5.01 (1H, m), 4.83 (2H, brs), 4.60 (2H, t, J = 6.8 Hz), 4.44 (2H, t, J = 6.4 Hz), 4.23-4.15 (2H, m), 3.87-3.81 (1H, m), 3.74 (2H, t, J = 7.2 Hz), 3.56 (2H, t, J = 7.2 Hz), 3.15-2.99 (3H, m), 2.38-2.27 (1H, m). | 721.5/0.813 |

TABLE 4-2

| | | | |
|---|---|---|---|
| 5 | Reference Example 10 | 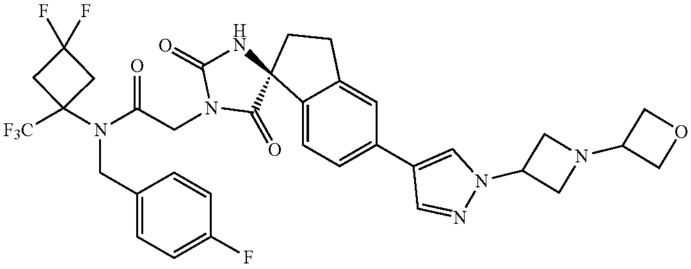 [SMILES: O=C1N[C@]2(CCc3cc(-c4cnn(C5CN(C6COC6)C5)c4)ccc32)C(=O)N1CC(=O)N(Cc1ccc(F)cc1)C1(C(F)(F)F)CC(F)(F)C1]<br>1H-NMR (400 MHz, DMSO-d6): δ8.78 (1H, s), 8.36 (1H, s), 7.97 (1H, s), 7.55 (1H, s), 7.49 (1H, d, J = 7.6 Hz), 7.40-7.36 (2H, m), 7.28 (2H, t, J = 8.8 Hz), 7.17 (1H, d, J = 8.0 Hz), 5.07-5.00 (1H, m), 4.83 (2H, brs), 4.60 (2H, t, J = 7.6 Hz), 4.44 (2H, t, J = 6.0 Hz), 4.18 (2H, brs), 3.87-3.81 (1H, m), 3.73 (2H, t, J = 7.6 Hz), 3.55 (2H, t, J = 8.4 Hz), 3.15-3.00 (4H, m), 2.23-2.16 (1H, m) | 703.5/0.831 |
| 6 | Reference Example 11 | 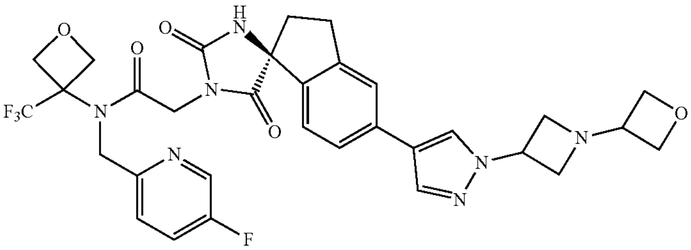 [SMILES: O=C1N[C@]2(CCc3cc(-c4cnn(C5CN(C6COC6)C5)c4)ccc32)C(=O)N1CC(=O)N(Cc1ccc(F)cn1)C1(C(F)(F)F)COC1]<br>1H-NMR (400 MHz, DMSO-d6): δ8.75 (1H, s), 8.60 (1H, d, J = 2.4 Hz), 8.36 (1H, s), 7.96 (1H, s), 7.83 (1H, td, J = 6.6, 2.8 Hz), 7.57-7.47 (3H, m), 7.16 (1H, d, J = 7.9 Hz), 5.07-5.00 (1H, m), 4.92 (2H, s), 4.60 (2H, t, J = 6.7 Hz), 4.44 (2H, t, J = 5.8 Hz), 4.13 (2H, s), 3.87-3.81 (1H, m), 3.73 (2H, t, J = 7.6 Hz), 3.55 (2H, t, J = 7.3 Hz), 3.24 (4H, t, J = 11.6 Hz), 3.01 (2H, t, J = 7.0 Hz), 2.53-2.48 (1H, m), 2.22-2.14 (1H, m). | 670.5/0.647 |

TABLE 4-2-continued

| | | | |
|---|---|---|---|
| 7 | Reference Example 15 | 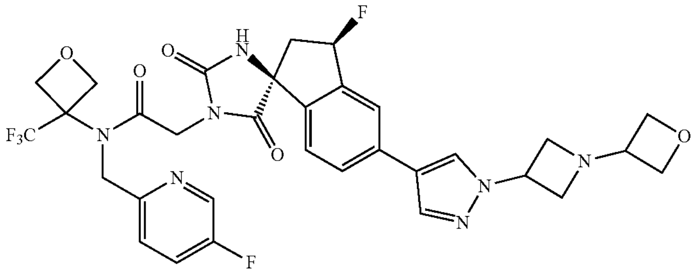 [SMILES: O=C1N[C@]2(C[C@@H](F)c3cc(-c4cnn(C5CN(C6COC6)C5)c4)ccc32)C(=O)N1CC(=O)N(Cc1ccc(F)cn1)C1(C(F)(F)F)COC1] | 688.5/0.664 |
| | | 1H-NMR (400 MHz, DMSO-d6): δ8.99 (1H, s), 8.64 (1H, d, J = 3.0 Hz), 8.47 (1H, s), 8.04 (1H, s), 7.82-7.76 (3H, m), 7.55 (1H, dd, J = 8.5, 4.3 Hz), 7.28 (1H, d, J = 7.9 Hz), 6.13 (1H, dt, J = 57.9, 5.5 Hz), 5.04 (1H, t, J = 7.0 Hz), 4.84 (4H, s), 4.63-4.58 (4H, m), 4.44 (2H, t, J = 5.8 Hz), 4.20 (2H, s), 3.84 (1H, t, J = 5.8 Hz), 3.74 (2H, t, J = 7.6 Hz), 3.56 (2H, t, J = 7.6 Hz), 3.06-2.97 (1H, m), 2.36-2.25 (1H, m). | |

TABLE 4-3

| | | | |
|---|---|---|---|
| 8 | Reference Example 12 | 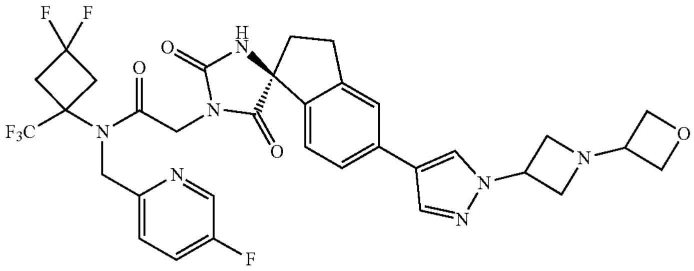 [SMILES: O=C1N[C@]2(CCc3cc(-c4cnn(C5CN(C6COC6)C5)c4)ccc32)C(=O)N1CC(=O)N(Cc1ccc(F)cn1)C1(C(F)(F)F)CC(F)(F)C1] | 704.5/0.762 |
| | | 1H-NMR (400 MHz, DMSO-d6): δ8.75 (1H, s), 8.60 (1H, d, J = 2.4 Hz), 8.36 (1H, s), 7.96 (1H, s), 7.83 (1H, td, J = 6.6, 2.8 Hz), 7.57-7.47 (3H, m), 7.16 (1H, d, J = 7.9 Hz), 5.07-5.00 (1H, m), 4.92 (2H, s), 4.60 (2H, t, J = 6.7 Hz), 4.44 (2H, t, J = 5.8 Hz), 4.13 (2H, s), 3.87-3.81 (1H, m), 3.73 (2H, t, J = 7.6 Hz), 3.55 (2H, t, J = 7.3 Hz), 3.24 (4H, t, J = 11.6 Hz), 3.01 (2H, t, J = 7.0 Hz), 2.53-2.48 (1H, m), 2.22-2.14 (1H, m). | |
| 9 | Reference Example 16 | 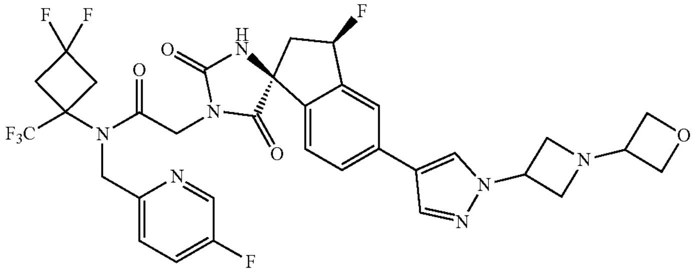 [SMILES: O=C1N[C@]2(C[C@@H](F)c3cc(-c4cnn(C5CN(C6COC6)C5)c4)ccc32)C(=O)N1CC(=O)N(Cc1ccc(F)cn1)C1(C(F)(F)F)CC(F)(F)C1] | 722.5/0.754 |
| | | 1H-NMR (400 MHz, DMSO-d6): δ8.99 (1H, s), 8.59 (1H, d, J = 2.4 Hz), 8.47 (1H, s), 8.04 (1H, s), 7.82-7.77 (3H, m), 7.54 (1H, dd, J = 8.5, 4.3 Hz), 7.30 (1H, d, J = 7.9 Hz), 6.22-6.04 (1H, m), 5.04 (1H, t, J = 7.0 Hz), 4.92 (2H, s), 4.60 (2H, t, J = 6.7 Hz), 4.44 (2H, dd, J = 6.4, 5.2 Hz), 4.13 (2H, s), 3.86-3.83 (1H, m), 3.74 (2H, t, J = 7.6 Hz), 3.55 (2H, t, J = 7.0 Hz), 3.26-3.24 (4H, m), 3.03-3.00 (1H, m), 2.37-2.25 (1H, m). | |

TABLE 4-3-continued
| | | | |
|---|---|---|---|
| 10 | Reference Example 19 | 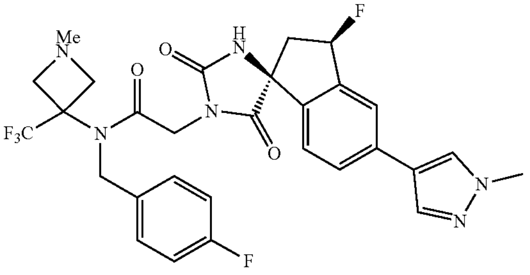 [SMILES: CN1CC(N(Cc2ccc(F)cc2)C(=O)CN2C(=O)N[C@]3(C[C@@H](F)c4cc(-c5cnn(C)c5)ccc43)C2=O)(C(F)(F)F)C1] | 603.4/0.670 |
| | | 1H-NMR (400 MHz, $CDCl_3$): δ7.75 (1H, s), 7.63-7.54 (3H, m), 7.44 (1H, d, J = 7.9 Hz), 7.37 (2H, dd, J = 9.2, 5.5 Hz), 7.15 (2H, t, J = 8.5 Hz), 6.16-5.99 (1H, m), 5.65 (1H, s), 4.52 (2H, br s), 4.16 (2H, br s), 3.98-3.84 (5H, m), 3.30 (2H, br s), 3.18-3.06 (1H, m), 2.52-2.41 (1H, m), 2.31 (3H, s). | |
TABLE 4-4
| | | | |
|---|---|---|---|
| 11 | Reference Example 19 | 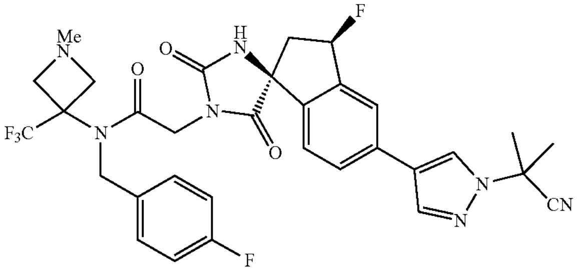 [SMILES: CN1CC(N(Cc2ccc(F)cc2)C(=O)CN2C(=O)N[C@]3(C[C@@H](F)c4cc(-c5cnn(C(C)(C)C#N)c5)ccc43)C2=O)(C(F)(F)F)C1] | 656.4/0.756 |
| | | 1H-NMR (400 MHz, $CDCl_3$): δ7.94-7.84 (2H, m), 7.65-7.57 (2H, m), 7.52-7.45 (1H, m), 7.42-7.34 (2H, m), 7.19-7.15 (2H, m), 6.18-5.99 (1H, m), 5.67-5.63 (1H, m), 4.56-4.48 (2H, m), 4.20-4.12 (2H, m), 3.94-3.85 (2H, m), 3.39-3.07 (3H, m), 2.55-2.41 (1H, m), 2.35-2.28 (3H, m), 2.07-1.98 (6H, m). | |
| 12 | Reference Example 17 | 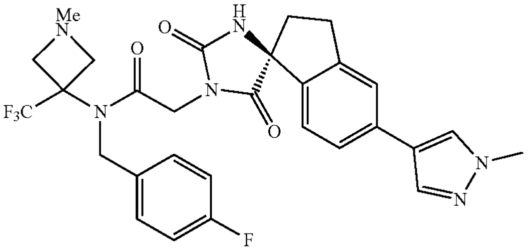 [SMILES: CN1CC(N(Cc2ccc(F)cc2)C(=O)CN2C(=O)N[C@]3(CCc4cc(-c5cnn(C)c5)ccc43)C2=O)(C(F)(F)F)C1] | 585.4/0.700 |
| | | 1H-NMR (400 MHz, $CDCl_3$): δ7.63 (1H, s), 7.50 (1H, s), 7.34-7.19 (5H, m), 7.08 (2H, t, J = 8.5 Hz), 5.62 (1H, s), 4.44 (2H, br s), 4.07 (2H, br s), 3.90-3.72 (5H, m), 3.29-3.08 (3H, m), 3.02-2.93 (1H, m), 2.75-2.67 (1H, m), 2.28-2.15 (4H, m). | |
| 13 | Reference Example 17 | 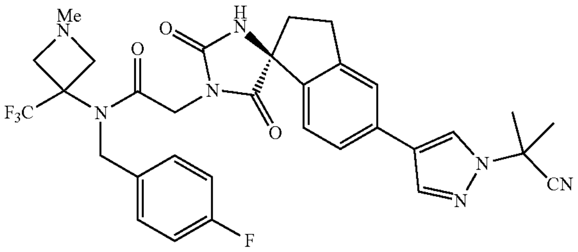 [SMILES: CN1CC(N(Cc2ccc(F)cc2)C(=O)CN2C(=O)N[C@]3(CCc4cc(-c5cnn(C(C)(C)C#N)c5)ccc43)C2=O)(C(F)(F)F)C1] | 638.4/0.798 |
| | | 1H-NMR (400 MHz, $CDCl_3$): δ7.86 (1H, s), 7.82 (1H, s), 7.41-7.29 (5H, m), 7.15 (2H, t, J = 8.5 Hz), 5.46 (1H, s), 4.51 (2H, s), 4.14 (2H, br s), 3.95-3.82 (2H, m), 3.35-3.17 (3H, m), 3.11-3.03 (1H, m), 2.84-2.76 (1H, m), 2.33-2.24 (4H, m), 2.02 (6H, s). | |

TABLE 4-5
| | | | |
|---|---|---|---|
| 14 | Reference Example 13 | 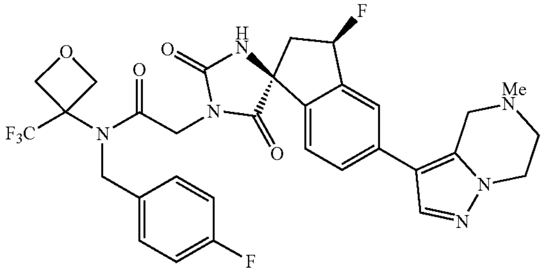 [SMILES: CN1CCn2ncc(-c3ccc4c(c3)[C@H](F)C[C@]43NC(=O)N(CC(=O)N(Cc4ccc(F)cc4)C4(C(F)(F)F)COC4)C3=O)c2C1] | 645.4/0.749 |
| 15 | Reference Example 19 | 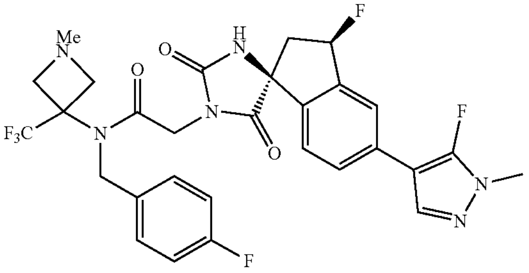 [SMILES: CN1CC(N(Cc2ccc(F)cc2)C(=O)CN2C(=O)N[C@]3(C[C@@H](F)c4cc(-c5cnn(C)c5F)ccc43)C2=O)(C(F)(F)F)C1] | 621.4/0.719 |
| | | 1H-NMR (400 MHz, $CDCl_3$): δ7.60-7.50 (3H, m), 7.40 (1H, d, J = 7.9 Hz), 7.31 (2H, dd, J = 8.5, 4.9 Hz), 7.09 (2H, t, J = 8.5 Hz), 6.11-5.92 (1H, m), 5.75 (1H, br s), 4.45 (2H, br s), 4.09 (2H, s), 3.90-3.77 (2H, m), 3.72 (3H, d, J = 1.2 Hz), 3.32-3.17 (2H, m), 3.12-3.00 (1H, m), 2.47-2.35 (1H, m), 2.25 (3H, s). | |
| 16 | Reference Example 17 | 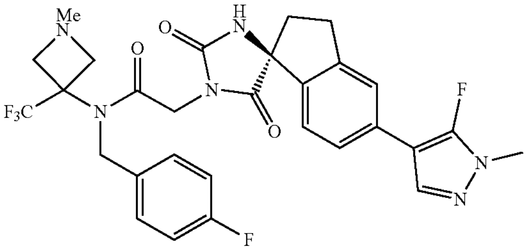 [SMILES: CN1CC(N(Cc2ccc(F)cc2)C(=O)CN2C(=O)N[C@]3(CCc4cc(-c5cnn(C)c5F)ccc43)C2=O)(C(F)(F)F)C1] | 603.4/0.698 |
| | | 1H-NMR (400 MHz, $CDCl_3$): δ7.52 (1H, d, J = 3.7 Hz), 7.36-7.21 (5H, m), 7.07 (2H, t, J = 8.2 Hz), 5.83 (1H, s), 4.44 (2H, br s), 4.06 (2H, s), 3.91-3.75 (2H, m), 3.70 (3H, s), 3.32-3.08 (3H, m), 3.04-2.93 (1H, m), 2.75-2.66 (1H, m), 2.27-2.15 (4H, m). | |
TABLE 4-6
| | | | |
|---|---|---|---|
| 17 | Reference Example 19 | 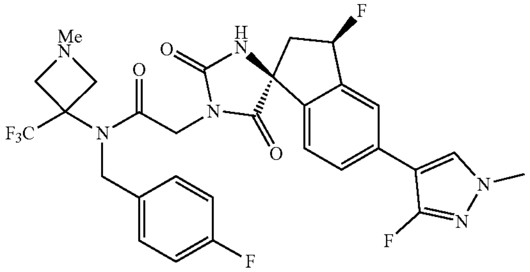 [SMILES: CN1CC(N(Cc2ccc(F)cc2)C(=O)CN2C(=O)N[C@]3(C[C@@H](F)c4cc(-c5cn(C)nc5F)ccc43)C2=O)(C(F)(F)F)C1] | 621.4/0.764 |
| | | 1H-NMR (400 MHz, $CDCl_3$): δ7.57 (1H, s), 7.51 (1H, d, J = 7.9 Hz), 7.40 (1H, d, J = 1.8 Hz), 7.37 (1H, d, J = 7.9 Hz), 7.30 (2H, dd, J = 8.5, 5.5 Hz), 7.08 (2H, t, J = 8.5 Hz), 6.10-5.91 (2H, m), 4.45 (2H, br s), 4.08 (2H, s), 3.91-3.71 (5H, m), 3.33-3.15 (2H, m), 3.11-2.98 (1H, m), 2.45-2.32 (1H, m), 2.23 (3H, s). | |

TABLE 4-6-continued
| | | | |
|---|---|---|---|
| 18 | Reference Example 17 | 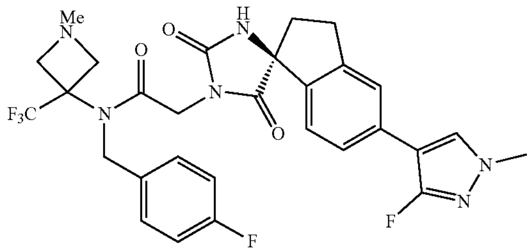 [SMILES: CN1CC(N(Cc2ccc(F)cc2)C(=O)CN2C(=O)N[C@]3(CCc4cc(-c5cn(C)nc5F)ccc43)C2=O)(C(F)(F)F)C1] | 603.4/0.749 |
1H-NMR (400 MHz, $CDCl_3$): δ7.43-7.33 (5H, m), 7.30 (1H, d, J = 7.9 Hz), 7.14 (2H, t, J = 8.5 Hz), 5.53 (1H, s), 4.51 (2H, br s), 4.13 (2H, s), 3.96-3.81 (2H, m), 3.79 (3H, s), 3.36-3.15 (3H, m), 3.10-3.01 (1H, m), 2.82-2.74 (1H, m), 2.34-2.22 (4H, m).
| | | | |
|---|---|---|---|
| 19 | Reference Example 19 | 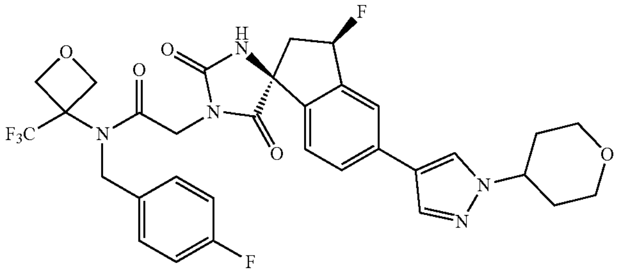 [SMILES: O=C1N[C@]2(C[C@@H](F)c3cc(-c4cnn(C5CCOCC5)c4)ccc32)C(=O)N1CC(=O)N(Cc1ccc(F)cc1)C1(C(F)(F)F)COC1] | 673.4/0.732 |
| 20 | Reference Example 20 | 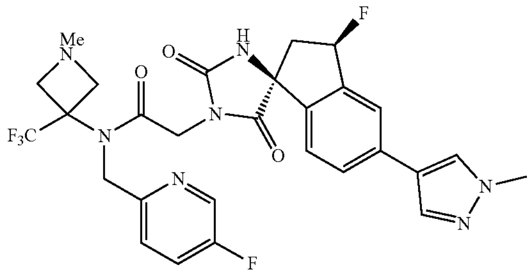 [SMILES: CN1CC(N(Cc2ccc(F)cn2)C(=O)CN2C(=O)N[C@]3(C[C@@H](F)c4cc(-c5cnn(C)c5)ccc43)C2=O)(C(F)(F)F)C1] | 604.3/0.618 |
1H-NMR (400 MHz, $CDCl_3$): δ8.47-8.29 (1H, m), 7.67 (1H, s), 7.59-7.33 (6H, m), 6.10-5.88 (2H, m), 4.53 (2H, br s), 4.12 (2H, s), 3.94-3.74 (5H, m), 3.33-3.16 (2H, m), 3.12-3.00 (1H, m), 2.46-2.20 (4H, m).
TABLE 4-7
| | | | |
|---|---|---|---|
| 21 | Reference Example 18 | 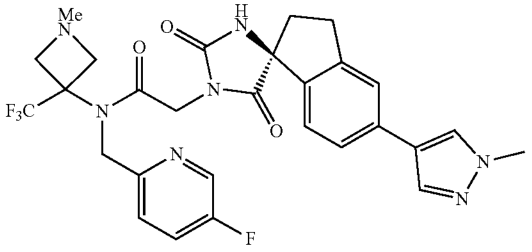 [SMILES: CN1CC(N(Cc2ccc(F)cn2)C(=O)CN2C(=O)N[C@]3(CCc4cc(-c5cnn(C)c5)ccc43)C2=O)(C(F)(F)F)C1] | 586.4/0.619 |
1H-NMR (400 MHz, $CDCl_3$): δ8.54-8.28 (1H, m), 7.78-7.20 (7H, m), 5.71 (1H, s), 4.53 (2H, br s), 4.28-3.73 (7H, m), 3.40-3.08 (3H, m), 3.05-2.93 (1H, m), 2.81-2.67 (1H, m), 2.43-2.16 (4H, m).

TABLE 4-7-continued
| | | | |
|---|---|---|---|
| 22 | Reference Example 13 | 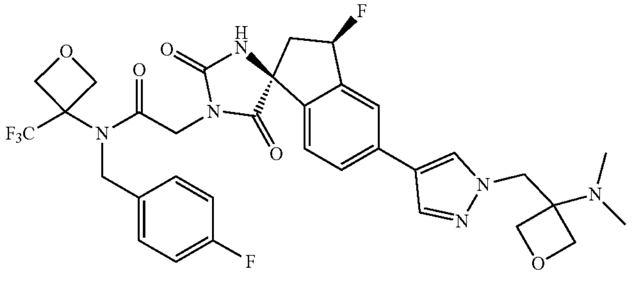 [SMILES: CN(C)C1(Cn2cc(-c3ccc4c(c3)[C@H](F)C[C@]43NC(=O)N(CC(=O)N(Cc4ccc(F)cc4)C4(C(F)(F)F)COC4)C3=O)cn2)COC1] | 689.4/0.768 |
| 23 | Reference Example 15 | 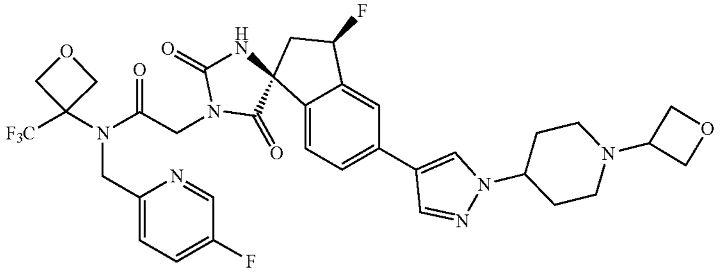 [SMILES: O=C1N[C@]2(C[C@@H](F)c3cc(-c4cnn(C5CCN(C6COC6)CC5)c4)ccc32)C(=O)N1CC(=O)N(Cc1ccc(F)cn1)C1(C(F)(F)F)COC1] | 716.4/0.726 |
| | | 1H-NMR (400 MHz, DMSO-d6): δ9.00 (1H, s), 8.65 (1H, d, J = 2.8 Hz), 8.37 (1H, s), 7.96 (1H, s), 7.82 (dt, J = 8.4, 2.8 Hz), 7.77 (1H, s), 7.73 (1H, d, J = 8.4 Hz), 7.55 (1H, dd, J = 8.4, 4.0 Hz), 7.27 (1H, d, J = 7.6 Hz), 6.21-6.04 (1H, m), 4.86-4.80 (4H, m), 4.63 (2H, d, J = 8.0 Hz), 4.54 (2H, t, J = 6.4 Hz), 4.44 (2H, t, J = 6.0 Hz), 4.21-4.12 (3H, m), 3.45-3.42 (1H, m), 3.05-2.97 (1H, m), 2.79-2.78 (2H, m), 2.36-2.25 (1H, m), 2.07-1.92 (6H, m). | |
TABLE 4-8
| | | | |
|---|---|---|---|
| 24 | Reference Example 20 | 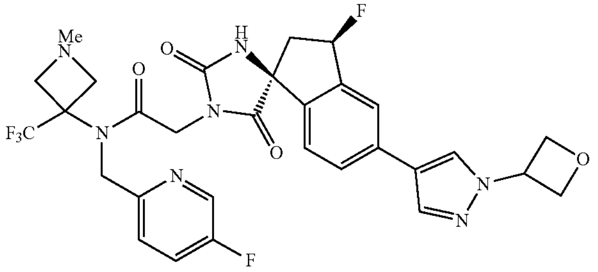 [SMILES: CN1CC(N(Cc2ccc(F)cn2)C(=O)CN2C(=O)N[C@]3(C[C@@H](F)c4cc(-c5cnn(C6COC6)c5)ccc43)C2=O)(C(F)(F)F)C1] | 646.3/0.659 |
| | | 1H-NMR (400 MHz, DMSO-d6): δ8.51 (1H, d, J = 2.4 Hz), 7.85 (1H, s), 7.85 (1H, s), 7.62-7.58 (2H, m), 7.52-7.42 (3H, m), 6.16-6.01 (1H, m), 5.74 (1H, s), 5.49-5.45 (1H, m), 5.08 (2H, s), 5.06 (2H, s), 4.60 (2H, s), 4.19 (2H, s), 3.93-3.88 (2H, m), 3.32-3.30 (2H, m), 3.18-3.08 (1H, m), 2.52-2.40 (1H, m), 2.30 (3H, s). | |
| 25 | Reference Example 20 | 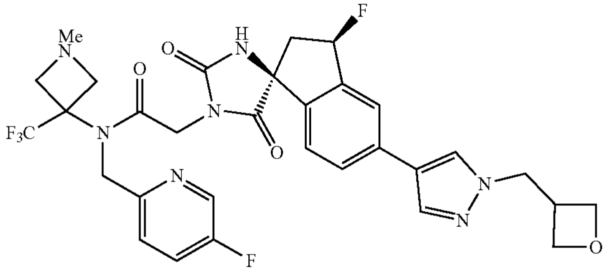 [SMILES: CN1CC(N(Cc2ccc(F)cn2)C(=O)CN2C(=O)N[C@]3(C[C@@H](F)c4cc(-c5cnn(CC6COC6)c5)ccc43)C2=O)(C(F)(F)F)C1] | 660.4/0.658 |

TABLE 4-8-continued
| | | | |
|---|---|---|---|
| 26 | Reference Example 20 | 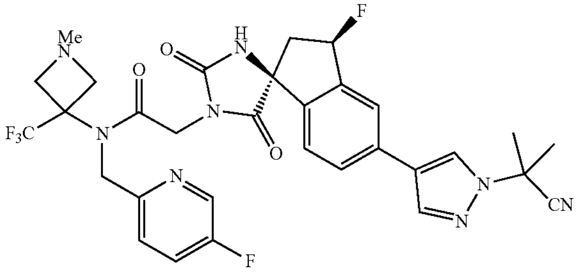 [SMILES: CN1CC(N(Cc2ccc(F)cn2)C(=O)CN2C(=O)N[C@]3(C[C@@H](F)c4cc(-c5cnn(C(C)(C)C#N)c5)ccc43)C2=O)(C(F)(F)F)C1] | 657.4/0.795 |
TABLE 4-9
| | | | |
|---|---|---|---|
| 27 | Reference Example 20 | 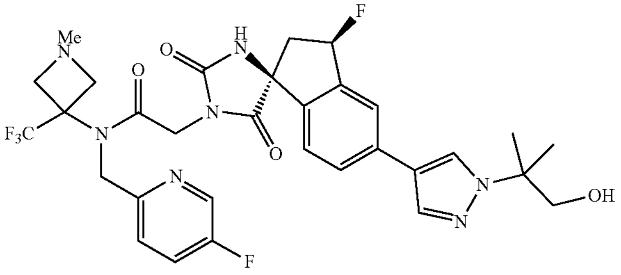 [SMILES: CN1CC(N(Cc2ccc(F)cn2)C(=O)CN2C(=O)N[C@]3(C[C@@H](F)c4cc(-c5cnn(C(C)(C)CO)c5)ccc43)C2=O)(C(F)(F)F)C1] | 662.4/0.697 |
| 28 | Reference Example 21 | 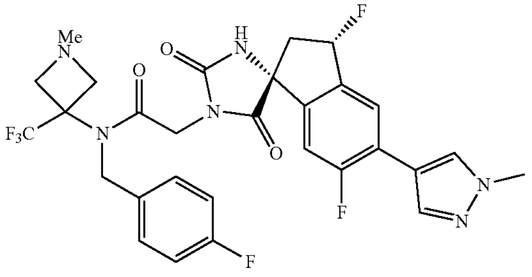 [SMILES: CN1CC(N(Cc2ccc(F)cc2)C(=O)CN2C(=O)N[C@@]3(C[C@H](F)c4cc(-c5cnn(C)c5)c(F)cc43)C2=O)(C(F)(F)F)C1] | 621.3/0.768 |
| 29 | Reference Example 21 | 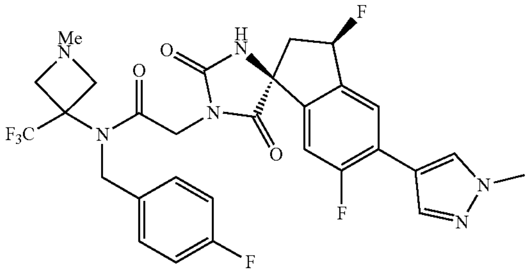 [SMILES: CN1CC(N(Cc2ccc(F)cc2)C(=O)CN2C(=O)N[C@]3(C[C@@H](F)c4cc(-c5cnn(C)c5)c(F)cc43)C2=O)(C(F)(F)F)C1] | 621.3/0.766 |
| | | 1H-NMR (400 MHz, $CDCl_3$): δ7.84 (1H, s), 7.77 (1H, d, J = 3.0 Hz), 7.70-7.67 (1H, m), 7.40-7.34 (2H, m), 7.25 (1H, t, J = 10.7 Hz), 7.16 (2H, t, J = 8.8 Hz), 6.13-5.95 (1H, m), 5.68 (1H, s), 4.59-4.45 (2H, m), 4.21-4.10 (2H, m), 3.99-3.83 (5H, m), 3.37-3.24 (2H, m), 3.19-3.08 (1H, m), 2.55-2.43 (1H, m), 2.31 (3H, s). | |

TABLE 4-10
| | | | |
|---|---|---|---|
| 30 | Reference Example 19 | 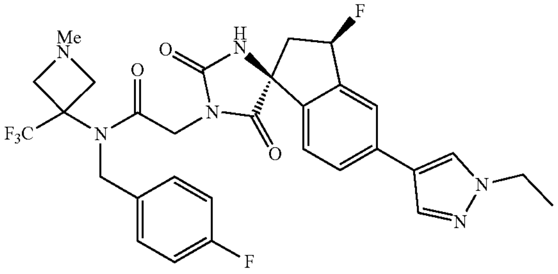 [SMILES: CCn1cc(-c2ccc3c(c2)[C@H](F)C[C@]32NC(=O)N(CC(=O)N(Cc3ccc(F)cc3)C3(C(F)(F)F)CN(C)C3)C2=O)cn1] | 617.3/0.713 |
| 1H-NMR (400 MHz, $CDCl_3$): δ7.75 (1H, s), 7.65 (1H, s), 7.60-7.55 (2H, m), 7.42 (1H, d, J = 8.0 Hz), 7.38-7.35 (2H, m), 7.17-7.13 (2H, m), 6.15-5.99 (1H, m), 5.82 (1H, s), 4.51 (1H, s), 4.22-4.15 (2H, m), 3.89 (2H, brs), 3.30 (2H, brs), 3.15-3.07 (1H, m), 2.50-2.45 (1H, m), 2.30 (3H, s), 1.56-1.50 (6H, m). | | | |
| 31 | Reference Example 19 | 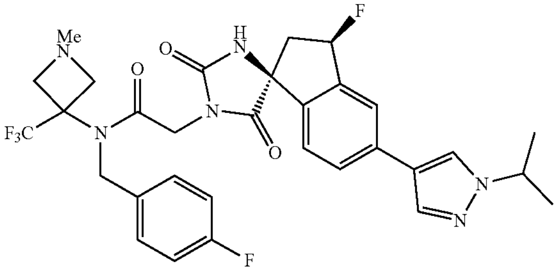 [SMILES: CC(C)n1cc(-c2ccc3c(c2)[C@H](F)C[C@]32NC(=O)N(CC(=O)N(Cc3ccc(F)cc3)C3(C(F)(F)F)CN(C)C3)C2=O)cn1] | 631.3/0.754 |
| 1H-NMR (400 MHz, $CDCl_3$): δ7.76 (1H, s), 7.67 (1H, s), 7.60 (1H, s), 7.57 (1H, d, J = 8.0 Hz), 7.42 (1H, d, J = 8.0 Hz), 7.39-7.35 (2H, m), 7.17-7.13 (2H, m), 6.15-5.99 (1H, m), 5.75 (1H, s), 4.54-4.48 (2H, m), 4.15 (2H, s), 3.89 (2H, brs), 3.30 (2H, brs), 3.17-3.07 (1H, m), 2.50-2.45 (1H, m), 2.31 (3H, s), 1.55-1.47 (6H, m), 1.11 (1H, d, J = 6.0 Hz). | | | |
| 32 | Reference Example 20 | 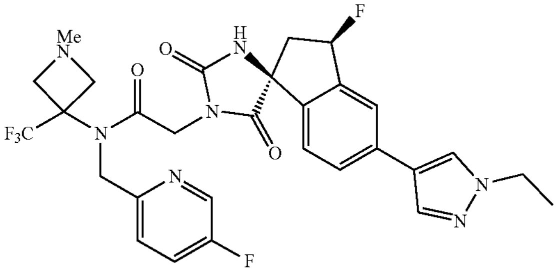 [SMILES: CCn1cc(-c2ccc3c(c2)[C@H](F)C[C@]32NC(=O)N(CC(=O)N(Cc3ccc(F)cn3)C3(C(F)(F)F)CN(C)C3)C2=O)cn1] | 618.3/0.656 |
| 1H-NMR (400 MHz, $CDCl_3$): δ8.52 (1H, d, J = 2.4 Hz), 7.77-7.40 (7H, m), 6.16-5.98 (1H, m), 5.72 (1H, s), 4.71-4.50 (2H, m), 4.24-3.40 (8H, m), 3.18-3.05 (1H, m), 2.51-2.36 (4H, m), 1.52 (3H, t, J = 7.3 Hz). | | | |

TABLE 4-11
| | | | |
|---|---|---|---|
| 33 | Reference Example 20 | 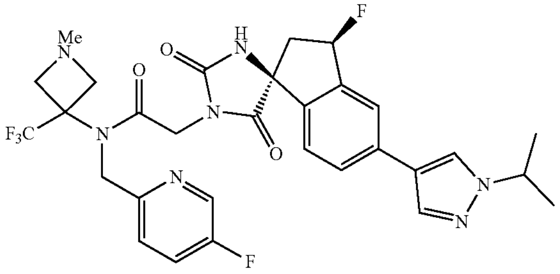 [SMILES: CC(C)n1cc(-c2ccc3c(c2)[C@H](F)C[C@]32NC(=O)N(CC(=O)N(Cc3ccc(F)cn3)C3(C(F)(F)F)CN(C)C3)C2=O)cn1] | 632.3/0.706 |
| | | 1H-NMR (400 MHz, $CDCl_3$): δ8.51 (1H, d, J = 2.4 Hz), 7.78-7.40 (7H, m), 6.17-5.97 (1H, m), 5.73 (1H, s), 4.68-4.46 (3H, m), 4.18 (2H, s), 4.09-3.86 (2H, m), 3.58-3.28 (2H, m), 3.19-3.05 (1H, m), 2.54-2.29 (4H, m), 1.53 (6H, d, J = 6.7 Hz). | |
| 34 | Reference Example 20 | 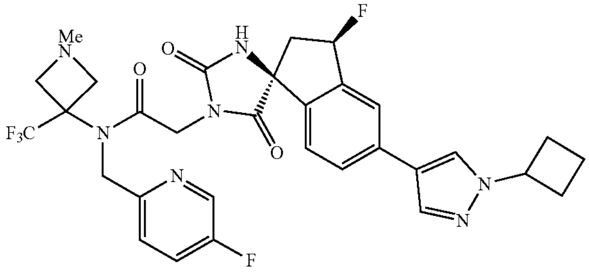 [SMILES: CN1CC(N(Cc2ccc(F)cn2)C(=O)CN2C(=O)N[C@]3(C[C@@H](F)c4cc(-c5cnn(C6CCC6)c5)ccc43)C2=O)(C(F)(F)F)C1] | 644.3/0.736 |
| | | 1H-NMR (400 MHz, $CDCl_3$): δ8.52 (1H, d, J = 2.4 Hz), 7.82-7.40 (7H, m), 6.17-5.97 (1H, m), 5.86-5.73 (1H, m), 4.85-4.53 (3H, m), 4.36-3.91 (4H, m), 3.82-3.40 (2H, m), 3.18-3.04 (1H, m), 2.62-2.36 (8H, m), 1.98-1.80 (2H, m). | |
| 35 | Reference Example 7 | 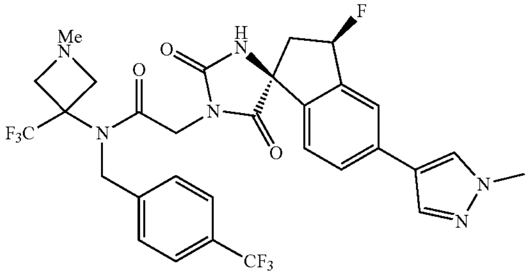 [SMILES: CN1CC(N(Cc2ccc(C(F)(F)F)cc2)C(=O)CN2C(=O)N[C@]3(C[C@@H](F)c4cc(-c5cnn(C)c5)ccc43)C2=O)(C(F)(F)F)C1] | 653.3/0.750 |
| | | 1H-NMR (400 MHz, $CDCl_3$): δ7.77-7.70 (3H, m), 7.63-7.37 (6H, m), 6.15-5.98 (1H, m), 5.80-5.69 (1H, m), 4.73-4.49 (2H, m), 4.29-4.06 (2H, m), 4.00-3.80 (5H, m), 3.40-3.20 (2H, m), 3.19-3.06 (1H, m), 2.53-2.40 (1H, m), 2.31 (3H, s). | |

Comparative Example 1

[Chemical Formula 31]

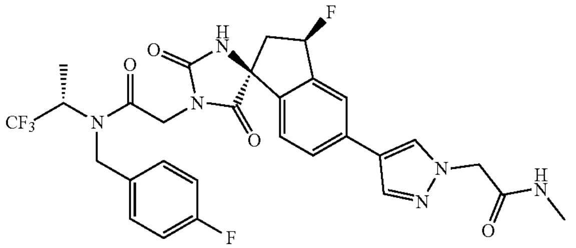

The compound of Comparative Example 1 was obtained by the method described in WO 2016/044770.

LC-MS ([M+H]+/Rt (min)): 619.4/0.938

Comparative Example 2

[Chemical Formula 32]

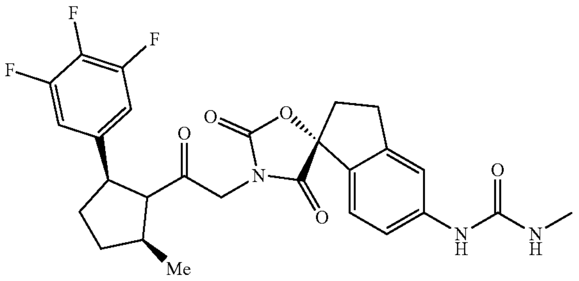

The compound of Comparative Example 2 was obtained by the method described in WO 2020/108500.

LC-MS ([M+H]+/Rt (min)): 531.3/0.965

TEST EXAMPLES

Test results for representative compounds of the present disclosure are shown below, and the pharmacological characteristics, chemical characteristics, and pharmacokinetics of the compounds are explained below, but the present disclosure is not limited to these test examples.

Test Example 1: HAT Activity Inhibition Experiment

The HAT activity inhibitory ability of HAT inhibitors was evaluated using SensoLyte HAT(p300) Assay Kit (ANASPEC, AS-72172). Specifically, 7.5 μL of the compound of Examples 1 to diluted with assay buffer was added to 7.5 μL of recombinant p300 solution diluted 10 times with assay buffer, and the mixture was incubated at room temperature for 10 minutes. 7.5 μL of acetyl CoA solution diluted 10 times with assay buffer and 15 μL of histone H3 peptide diluted 10 times with assay buffer were added thereto, and the mixture was incubated at 37° C. for 30 minutes. 37.5 μL of Stop Solution was added to stop the reaction. 75 μL of p300 Developer solution diluted 50 times with assay buffer was added, and the mixture was incubated at room temperature for 30 minutes under light-shielded conditions. The fluorescence at 513 nm when irradiated with 389 nm excitation light was measured using a multiplate reader. Based on the measured fluorescence intensity, the $IC_{50}$ value, which corresponds to the concentration of the compound that shows 50% inhibition of the enzyme reaction, was calculated. The results are shown in Table 5.

TABLE 5

| Example | HAT activity inhibition $IC_{50}$ (μM) |
|---|---|
| 1 | 0.016 |
| 2 | 0.019 |
| 3 | 0.0006 |
| 4 | 0.0005 |
| 5 | 0.0061 |
| 6 | 0.0198 |
| 7 | 0.0009 |
| 8 | 0.0172 |
| 9 | 0.0006 |
| 10 | 0.0004 |
| 11 | 0.0021 |
| 12 | 0.0063 |
| 13 | 0.0052 |
| 14 | 0.1236 |
| 15 | 0.0061 |
| 16 | 0.0536 |
| 17 | 0.0023 |
| 18 | 0.0582 |
| 19 | 0.0072 |
| 20 | 0.0017 |
| 21 | 0.052 |
| 22 | 0.011 |
| 23 | 0.009 |
| 24 | 0.0098 |
| 25 | 0.0057 |
| 26 | 0.0092 |
| 27 | 0.0068 |
| 29 | 0.0028 |
| 30 | 0.0015 |
| 31 | 0.0010 |
| 32 | 0.0004 |
| 33 | 0.0002 |
| 34 | 0.0002 |
| 35 | 0.0052 |

As shown in Table 5, a series of the compounds of the present disclosure were confirmed to inhibit the function of the HAT domain of P300/CBP. Among them, in particular, Examples 3 to 5, 7, 9 to 13, 15, 17, 18 to 20, 23 to 27, and 29 to 35 showed strong inhibition of HAT activity.

Test Example 2: Cell Proliferation Inhibition Experiment Using G-401 Cells

G-401 cells (derived from malignant rhabdoid tumor) were obtained from the American Type Culture Collection (ATCC). G-401 cells were cultured in McCoy's 5A medium containing 10% fetal bovine serum and 1% penicillin/streptomycin under conditions of 37° C. and 5% $CO_2$.

500 cells per well were seeded in a 384-well plate. One day after seeding, Examples 1 to 35 were added so that the final concentration of DMSO was 0.1%, and the cells were cultured for 3 days. After the culture was completed, the cell viability was measured using CellTiter-Glo Luminescent Cell Viability Assay (Promega, G7570). From the viability curve, the $IC_{50}$ value, which corresponds to the concentration of the evaluation compound that shows 50% inhibition of cell proliferation, was calculated. The results are shown in Table 6.

TABLE 6

| Example | Cell proliferation inhibition $IC_{50}$ (μM) |
|---|---|
| 1 | 0.181 |
| 2 | 0.089 |
| 3 | 0.044 |
| 4 | 0.043 |
| 5 | 0.088 |
| 6 | 0.391 |
| 7 | 0.044 |
| 8 | 0.247 |
| 9 | 0.038 |
| 10 | 0.01 |
| 11 | 0.01 |
| 12 | 0.082 |
| 13 | 0.02 |
| 14 | 0.677 |
| 15 | 0.033 |
| 16 | 0.31 |
| 17 | 0.025 |
| 18 | 0.292 |
| 19 | 0.024 |
| 20 | 0.036 |
| 21 | 0.353 |
| 22 | 0.068 |
| 23 | 0.082 |
| 24 | 0.036 |
| 25 | 0.059 |
| 26 | 0.014 |
| 27 | 0.022 |
| 29 | 0.017 |
| 30 | 0.002 |
| 31 | 0.001 |
| 32 | 0.005 |
| 33 | 0.004 |
| 34 | 0.005 |
| 35 | 0.072 |

As shown in Table 6, a series of compounds of the present disclosure showed strong cell proliferation inhibitory effects on G-401 cells, which are cells derived from malignant rhabdoid tumors. Among them, in particular, Examples 2 to 5, 7, 9 to 13, 15, 17, 19, 20, 22 to 27, and 29 to 35 showed a strong cell proliferation inhibitory effect.

Test Example 3: Cell Proliferation Inhibition Experiment Using Kuramochi Cells

Kuramochi cells (derived from ovarian cancer) were obtained from JCRB (Japanese Collection of Research Bioresources) cell bank. Kuramochi cells were cultured in RPMI-1640 medium containing 10% fetal bovine serum and 1% penicillin/streptomycin under conditions of 37° C. and 5% $CO_2$.

500 cells per well were seeded in a 384-well plate. One day after seeding, Examples 3, 7, 9, 10, 11, 20, 23 to 25, and 30 to 34 were added so that the final concentration of DMSO was 0.1%, and the cells were cultured for 6 days. After the culture was completed, the cell viability was measured using CellTiter-Glo Luminescent Cell Viability Assay (Promega, G7570). From the viability curve, the $IC_{50}$ value, which corresponds to the concentration of the evaluation compound that shows 50% inhibition of cell proliferation, was calculated. The results are shown in Table 7.

TABLE 7

| Example | Cell proliferation inhibition $IC_{50}$ (μM) |
|---|---|
| 3 | 0.091 |
| 7 | 0.298 |
| 9 | 0.184 |
| 10 | 0.066 |
| 11 | 0.048 |
| 20 | 0.320 |
| 23 | 0.591 |
| 24 | 0.399 |
| 25 | 0.424 |
| 30 | 0.010 |
| 31 | 0.008 |
| 32 | 0.053 |
| 33 | 0.024 |
| 34 | 0.045 |

Test Example 4: Cell Proliferation Inhibition Experiment Using RMGI Cells

RMGI cells (derived from ovarian cancer) were obtained from JCRB cell bank. RMGI cells were cultured in Ham's F12 medium containing 10% fetal bovine serum and 1% penicillin/streptomycin under conditions of 37° C. and 5% $CO_2$.

200 cells per well were seeded in a 384-well plate. One day after seeding, Examples 3, 7, 9, 10, 11, 20, and 23 to 25 were added so that the final concentration of DMSO was 0.1%, and the cells were cultured for 6 days. After the culture was completed, the cell viability was measured using CellTiter-Glo Luminescent Cell Viability Assay (Promega, G7570). From the viability curve, the $IC_{50}$ value, which corresponds to the concentration of the evaluation compound that shows 50% inhibition of cell proliferation, was calculated. The results are shown in Table 8.

TABLE 8

| Example | Cell proliferation inhibition $IC_{50}$ (μM) |
|---|---|
| 3 | 0.018 |
| 7 | 0.035 |
| 9 | 0.024 |
| 10 | 0.006 |
| 11 | 0.005 |
| 20 | 0.043 |
| 23 | 0.054 |
| 24 | 0.037 |
| 25 | 0.041 |

Test Example 5: Solubility Test

The solubility was measured for Examples 7, 10, 20, 23, 24, and 30 to 34, Comparative Example 1, and Comparative Example 2. The test compound was added to 10 mmol/L glycine buffer (pH 2.0) and 10 mmol/L citrate buffer (pH 3.0), and the mixture was stored in a thermostatic chamber at 5° C. After standing overnight, the mixture was filtered through a membrane filter, and the concentration of the filtrate was measured by HPLC.

The HPLC measurement conditions are as follows.

HPLC Conditions

Column: Acquity UPLC BEH C18, 1.7 μm, 50×2.1 mm

Column temperature: 40° C.

Mobile phase: A: 0.1% trifluoroacetic acid-containing water

B: acetonitrile

A/B (min): 95/5 (0)→0/100 (3.5)→0/100 (4)→95/5 (4.01)→95/5 (5)

Flow rate: 0.8 mL/min

Detection: UV visible detector, measurement wavelength 254 nm

Injection volume: 5 μL or

Column: Acquity UPLC BEH C18, 1.7 μm, 50×2.1 mm

Column temperature: 40° C.

Mobile phase: A: 0.1% trifluoroacetic acid-containing water

B: acetonitrile

A/B (min): 80/20 (0)→40/60 (3.0)→0/100 (3.5)→0/100 (4)→80/20 (4.01)→80/20 (5)

Flow rate: 0.8 mL/min

Detection: UV visible detector, measurement wavelength 254 nm

Injection volume: 2 μL or

Column: Acquity UPLC BEH C18, 1.7 μm, 50×2.1 mm

Column temperature: 40° C.

Mobile phase: A: 0.1% trifluoroacetic acid-containing water

B: acetonitrile

A/B (min): 80/20 (0)→40/60 (3.0)→0/100 (3.5)→0/100 (4)→100/0 (4.01)→100/0 (5)

Flow rate: 0.8 mL/min

Detection: UV visible detector, measurement wavelength 254 nm

Injection volume: 3 μL

The results are shown in Table 9.

Examples 7, 10, 20, 23, 24, and 30 to 34 showed high solubility. On the other hand, Comparative Example 1 and Comparative Example 2 showed extremely low solubility of 0.002 mg/mL, 0.004 mg/mL, and 0.005 mg/mL at pH 2.0 and pH 3.0, respectively. From the test results, it was confirmed that Examples 7, 10, 20, 23, 24, and 30 to 34 are compounds that show exceptional effects on solubility.

TABLE 9

| Compound | Solubility (mg/mL) in pH 2.0 buffer | Solubility (mg/mL) in pH 3.0 buffer |
|---|---|---|
| Example 7 | >10 | 4.6 |
| Example 10 | >10 | 1.6 |
| Example 20 | >10 | 8.6 |
| Example 23 | >10 | 8.6 |
| Example 24 | >10 | >10 |
| Example 30 | 8.8 | 1.7 |
| Example 31 | 7.1 | 1.4 |
| Example 32 | >10 | >10 |
| Example 33 | >10 | 8.6 |
| Example 34 | >10 | 8.1 |
| Comparative Example 1 | 0.002 | 0.005 |
| Comparative Example 2 | 0.004 | 0.005 |

Test Example 6: Membrane Permeability Test

The membrane permeability of the test compound was tested by parallel artificial membrane permeability assay (PAMPA) as follows. 200 μL of System solution (pION Inc.) containing the test compound and 4 μL of GIT Lipid-0 (pION Inc.) were added to the donor plate. 200 μL of Acceptor Sink Buffer (pION Inc.) was added to the acceptor plate. Both plates were overlapped and incubated at 37° C. for 4 hours, after which the UV of the solutions on the acceptor side and donor side was measured using a UV plate reader (190-500 nm). Compounds with poor UV absorption were measured using LC-MS. The permeability coefficient Pe ($10^{-6}$ cm/sec) of the drug was calculated using the following equation.

$$P_e = -\frac{2.303 V_D}{A(t-\tau_{SS})}\left(\frac{1}{1+r_a}\right)\cdot \log_{10}\left[-r_a + \left(\frac{1+r_a}{1-R}\right)\cdot\frac{C_D(t)}{C_D(0)}\right] \quad \text{[Equation 1]}$$

$$r_a = (V_D/V_A)P_e^{(A\to D)} \big/ P_e^{(D\to A)} = r_V P_e^{(A\to D)} \big/ P_e^{(D\to A)}$$

$$r_V = (V_D/V_A)$$

$$V_D = \text{volume of donor well}$$

$$V_A = \text{volume of acceptor well}$$

$$t = \text{permeation time}$$

$$\tau^{SS} = \text{steady state time}$$

$$R = \text{retention}$$

$$C_D \text{ and } C_A = \text{concentration in donor and acceptor well}$$

The results are shown in Table 10.

TABLE 10

| Example | pH 5.0 Pe ($10^{-6}$ cm/s) | pH 7.4 Pe ($10^{-6}$ cm/s) |
|---|---|---|
| 1 | 16.2 | 20.6 |
| 2 | 7.4 | 19.0 |
| 3 | 14.9 | 17.7 |
| 4 | 25.7 | 31.2 |
| 5 | 25.4 | 28.4 |
| 6 | 3.1 | 5.5 |
| 7 | 3.0 | 5.1 |
| 8 | 13.5 | 14.3 |
| 9 | 13.3 | 15.3 |
| 10 | 23.9 | 28.6 |
| 11 | 24.1 | 27.2 |
| 12 | 24.0 | 28.9 |
| 13 | 26.2 | 26.9 |
| 14 | 26.1 | 27.9 |
| 15 | 30.0 | 33.3 |
| 16 | 29.2 | 32.0 |
| 17 | 28.1 | 32.2 |
| 18 | 28.6 | 31.8 |
| 19 | 24.4 | 28.9 |
| 20 | 7.8 | 21.9 |
| 21 | 6.2 | 21.2 |
| 22 | 21.2 | 23.0 |
| 23 | 3.2 | 7.0 |
| 24 | 1.6 | 8.2 |
| 25 | 1.0 | 6.1 |
| 26 | 10.2 | 16.3 |
| 27 | 0.6 | 3.5 |
| 28 | 25.7 | 30.0 |
| 29 | 23.9 | 28.3 |
| 30 | 30.6 | 35.0 |
| 31 | 31.3 | 34.9 |
| 32 | 15.4 | 26.6 |
| 33 | 22.6 | 27.0 |
| 34 | 24.4 | 34.9 |
| 35 | 31.2 | 33.7 |
| Comparative Example 1 | 21.3 | 20.8 |

Test Example 7: Pharmacokinetic Study in Mice

The test compound was administered to 7-week-old female BALB/c (BALB/cAnN CrlCrlj) mice intravenously (dosage: 1 mg/kg) in a 50% PEG solution (0.01 mol/L HCl) or orally (dosage: 10 mg/kg) in a 0.5% methylcellulose aqueous solution, and blood was collected at the following times:

Intravenous administration: 5 min, 15 min, 30 min, 1 hr, 2 hr, 4 hr, 6 hr, and 24 hr after administration Oral administration: 15 min, 30 min, 1 hr, 2 hr, 4 hr, 6 hr, and 24 hr after administration The collected blood was centrifuged at 3000 rpm×10 min using a refrigerated centrifuge set at 4° C., and the obtained plasma was measured by LC-MS. A calibration curve was prepared from the value (peak ratio) obtained by dividing the peak area of the test substance by the peak area of the internal standard substance in MS and the concentration of the plasma calibration curve sample. The concentration in the sample was calculated from the peak ratio and the calibration curve of each sample.

The results for Examples 1, 3 to 5, 7, 9 to 12, 20, and 23 to 25 are shown in Table 11.

From the test results, it was confirmed that the compounds of the present disclosure have excellent pharmacokinetic properties and are useful in vivo.

TABLE 11

| Example | Method of administration | Half-life (hr) | CL (mL/min/kg) | $V_{dss}$ (L/kg) | AUC (ng · hr/mL) | BA (%) | $C_{max}$ (ng/mL) |
|---|---|---|---|---|---|---|---|
| 1 | Intravenous | 1.10 | 28.6 | 1.8 | 575 | | |
| | Oral | | | | 4351 | 75.7 | 3767 |
| 3 | Intravenous | 1.80 | 20.6 | 2.0 | 764 | | |
| | Oral | | | | 3890 | 50.9 | 2673 |
| 4 | Intravenous | 2.30 | 6.8 | 1.2 | 2103 | | |
| | Oral | | | | 28657 | 136.3 | 8303 |
| 5 | Intravenous | 1.75 | 17.6 | 2.1 | 875 | | |
| | Oral | | | | 7297 | 83.4 | 3500 |
| 7 | Intravenous | 1.41 | 19.9 | 1.3 | 819 | | |
| | Oral | | | | 8242 | 100.6 | 6140 |
| 9 | Intravenous | 2.43 | 11.9 | 2.0 | 1201 | | |
| | Oral | | | | 13103 | 109.1 | 5373 |
| 10 | Intravenous | 1.16 | 33.5 | 1.8 | 491 | | |
| | Oral | | | | 3480 | 70.8 | 3243 |
| 11 | Intravenous | 2.12 | 33.7 | 4.1 | 446 | | |
| | Oral | | | | 2505 | 56.2 | 1717 |
| 12 | Intravenous | 0.97 | 35.7 | 1.6 | 465 | | |
| | Oral | | | | 1396 | 30.0 | 1293 |
| 20 | Intravenous | 1.34 | 31.1 | 1.6 | 528 | | |
| | Oral | | | | 1521 | 28.8 | 1337 |
| 23 | Intravenous | 4.10 | 9.8 | 1.8 | 1689 | | |
| | Oral | | | | 8401 | 49.7 | 8137 |
| 24 | Intravenous | 1.15 | 53.0 | 2.1 | 313 | | |
| | Oral | | | | 1471 | 47.0 | 1474 |
| 25 | Intravenous | | | | 672 | | |
| | Oral | | | | 1314 | 19.6 | 1627 |

Test Example 8: Drug Efficacy Evaluation Test by Oral Administration Using G-401 Xenograft Model Mice G-401 cells (ATCC) were intradermally transplanted into 4-7-week-old BALB/cAnNCrj-nu/nu mice (CAnN.Cg-Foxn1<nu>/CrlCrlj, Jackson Laboratory Japan) at $5\times10^5$ cells/mouse. After confirming the engraftment of G-401 cells 10-40 days after transplantation, the test compound suspended in a solvent such as 0.5% methylcellulose solution was orally administered twice a day at a dose of 1-100 mg/kg. The tumor volume was measured over time from the start of administration, and the effect of tumor volume reduction by administration of the test compound was evaluated. The tumor volume can be calculated from the following equation using the minor axis and major axis of the tumor measured with an electronic caliper (Mitutoyo).

$$\text{Tumor volume } [\text{mm}^3] = 0.5 \times \text{minor axis [mm]} \times (\text{major axis [mm]})^2$$

A control administration group administered with only a solvent such as 0.5% methylcellulose solution and a test compound administration group were compared, and the antitumor effect was evaluated by calculating T/C from the following equation.

$$T/C\ (\%) = (\text{tumor volume at the end of administration in the test compound administration group} - \text{tumor volume at the start of administration in the test compound administration group}) / (\text{tumor volume at the end of administration in the control administration group} - \text{tumor volume at the start of administration in the control administration group}) \times 100$$

The dosage and dosage period for Examples 7, 10, 20, and 23 are shown in Table 12.

According to the test results, Examples 7, 10, 20, and 23 showed strong antitumor effects in the G-401 xenograft model, which is a cell line derived from malignant rhabdoid tumor.

TABLE 12

| Example | Dosage (mg/kg) | Dosage period (days) |
|---|---|---|
| 7 | 10 | 34 |
| 7 | 30 | 34 |
| 10 | 3 | 21 |
| 10 | 10 | 21 |
| 20 | 20 | 21 |
| 20 | 30 | 21 |
| 23 | 20 | 21 |

Test Example 9: Drug Efficacy Evaluation Test by Intravenous Administration Using G-401 Xenograft Mice Model G-401 cells (ATCC) were intradermally transplanted into 4-7-week-old BALB/cAnNCrj-nu/nu mice (CAnN.Cg-Foxn1<nu>/CrlCrlj, Jackson Laboratory Japan) at $5\times10^5$ cells/mouse. After confirming the engraftment of G-401 cells 10-40 days after transplantation, the test compound suspended in a solvent such as 10 mmol/L glycine buffer solution (pH 2.0) was administered via the tail vein at least once a week at a dose of 0.015-20 mg/kg. The tumor volume was measured over time from the start of administration, and the effect of tumor volume reduction by administration of the test compound was evaluated. The tumor volume can be calculated from the following equation using the minor axis and major axis of the tumor measured with an electronic caliper (Mitutoyo).

$$\text{Tumor volume } [\text{mm}^3] = 0.5 \times \text{minor axis [mm]} \times (\text{major axis [mm]})^2$$

A control administration group administered with only a solvent such as 10 mmol/L glycine buffer solution (pH 2.0) and a test compound administration group were compared, and the antitumor effect was evaluated by calculating T/C from the following equation.

-continued $$T/C\ (\%) = (\text{tumor volume at the end of administration in the test compound administration group} - \text{tumor volume at the start of administration in the test compound administration group}) / (\text{tumor volume at the end of administration in the control administration group} - \text{tumor volume at the start of administration in the control administration group}) \times 100$$

The dosage and dosage period for Examples 7, 10, 20, 23, and 24 and Comparative Example 1 are shown in Table 13.

According to the test results, Examples 7, 10, 20, 23, and 24 showed strong antitumor effects even when administered intravenously in a G-401 xenograft model, which is a cell derived from malignant rhabdoid tumor. On the other hand, Comparative Example 1 showed no antitumor effect even when administered at the maximum concentration.

TABLE 13

| Example | Dosage (mg/kg) | Dosage period (days) |
|---|---|---|
| 7 | 20 | 14 |
| 10 | 10 | 14 |
| 20 | 10 | 14 |
| 23 | 20 | 14 |
| 24 | 20 | 14 |
| Comparative Example 1 | 0.015 | 14 |

Test Example 10: Dopamine Receptor Inhibitory Activity Evaluation

The binding evaluation assay was outsourced to Eurofins. Specifically, CHO-S/hDAT cells were homogenized in an incubation buffer consisting of 50 mmol/L Tris-HCl, pH 7.4, 100 mmol/L NaCl, 1 µmol/L Leupeptin, and 10 µmol/L PMSF. The membrane pellet obtained by centrifugation was resuspended in the incubation buffer to prepare a membrane preparation. The test compound (1-10 µmol/L DMSO solution), the membrane preparation, and 0.15 nmol/L [$^3$H] kParoxetine were mixed and incubated at 4° C. for 180 minutes. The cell membrane-[$^{125}$I]RTI-55 complex was bound to a GF/B filter mat by vacuum filtration and washed with 50 mmol/L Tris-HCl, pH 7.4. The effect on the receptor was assessed by measuring radioactivity using a scintillation counter.

The results are shown in Table 14.

TABLE 14

| Compound | Inhibitory activity (%) at 10 µM |
|---|---|
| Example 7 | 7 |
| Example 10 | 6 |
| Example 20 | 46 |
| Example 23 | 7 |
| Example 24 | 6 |
| Example 25 | 9 |
| Comparative Example 2 | 88 |

Test Example 11: Serotonin Receptor Inhibitory Activity Evaluation

The binding evaluation assay was outsourced to Eurofins. Specifically, HEK293/hSERT cells were homogenized in a buffer consisting of 100 mmol/L NaCl, 1 µmol/L Leupeptin, 10 µmol/L PMSF, and 50 mmol/L Tris-HCl (pH7.4). The membrane pellet obtained by centrifugation was resuspended in an incubation buffer consisting of 50 mmol/L Tris-HCl (pH 7.4), 120 mmol/L NaCl, and 5 mmol/L KCl to prepare a membrane preparation. The test compound (1-10 μmol/L DMSO solution), the membrane preparation, and 0.4 nmol/L [$^3$H]Paroxetin were mixed and incubated at 25° C. for 60 minutes. The cell membrane-[$^3$H]Paroxetin complex was bound to a GF/B filter mat by vacuum filtration and washed with 50 mmol/L Tris-HCl (pH 7.4). The effect on the receptor was assessed by measuring radioactivity using a scintillation counter.

The results are shown in Table 15.

TABLE 15

| Compound | Inhibitory activity (%) at 10 μM |
|---|---|
| Example 7 | −1 |
| Example 10 | −5 |
| Example 20 | −1 |
| Example 23 | 3 |
| Example 24 | 15 |
| Example 25 | 2 |
| Comparative Example 2 | 76 |

From the results of Test Examples 10 and 11, it was confirmed that the compounds of the present disclosure do not act on off-targets that pose safety concerns. On the other hand, it was revealed that Comparative Example 2 has a strong inhibitory effect on dopamine receptors and serotonin receptors.

According to the results of Test Examples 1 to 11, the compounds of the present disclosure showed strong HAT inhibitory activity (Test Example 1) and strong cancer cell proliferation inhibitory effects (Test Examples 2 to 4). In addition, the compounds of the present disclosure showed excellent solubility (Test Example 5), high membrane permeability (Test Example 6), and good pharmacokinetics (Test Example 7), as well as exceptional antitumor effects (Test Example 8). Furthermore, the compounds of the present disclosure showed exceptional antitumor effects in xenograft model mice even when administered intravenously (Test Example 9), and also showed exceptionally remarkable and heterogeneous safety since it did not show strong inhibitory activity against dopamine receptors and serotonin receptors, which are off-targets (Test Examples 10 and 11).

The present inventors have newly found a problem that the solubility of Comparative Example 1 and Comparative Example 2 is low, making intravenous administration difficult. In general, when structural conversion is performed to increase solubility, liposolubility is weakened and membrane permeability is impaired. However, among the compounds of the present disclosure, the compounds represented by formulas (2) to (7) in particular have heterogeneous effects with both excellent solubility (Test Example 5) and high membrane permeability (Test Example 6), and therefore are excellent CBP/P300 inhibitors that can be administered orally and intravenously.

Among the compounds of the present disclosure, Examples 7, 10, 20, 23, 24, 25, and 30 to 34, which are included in Formula (2), Formula (3), Formula (5) or Formula (6), showed strong HAT inhibitory activity (Test Example 1) and strong cancer cell proliferation inhibitory effects (Test Examples 2 to 4). In addition, generally, when structural conversion is performed to increase solubility, liposolubility is weakened and membrane permeability is impaired, but Examples 7, 10, 20, 23, 24, and 30 to 34 have heterogeneous effects with both better solubility than Comparative Example 1 and Comparative Example 2 (Test Example 5) and membrane permeability comparable to Comparative Example 1 and Comparative Example 2 (Test Example 6). Furthermore, Examples 7, 10, 20, 23, and 24 showed excellent pharmacokinetics (Test Example 7). Examples 7, 10, 20, and 23 showed exceptional antitumor effects when administered orally (Test Example 8), and also showed exceptionally remarkable antitumor effects in tumors that could not be achieved by Comparative Example 1 when administered intravenously (Test Example 9). Thus, they are CBP/P300 inhibitors having a profile suitable for oral and intravenous administration. In addition, while Comparative Example 2 showed strong inhibitory activity against the off-target dopamine receptors and serotonin receptors, Examples 7, 10, 20, 23, 24, and 25 did not show strong inhibitory activity, demonstrating exceptionally remarkable and heterogeneous safety Test Examples 10 and 11

Note

As described above, although the present disclosure has been illustrated using the preferable embodiments thereof, it is understood that the scope of the present disclosure should be interpreted only by the claims. It is understood that the patents, patent applications, and other documents cited herein should be incorporated by reference into this specification to the same extent as if the contents themselves were specifically set forth herein. This application claims priority to PCT/JP2024/004222 (filed with the Japan Patent Office as the receiving office on Feb. 7, 2024), and their contents are incorporated herein by reference in their entirety.

INDUSTRIAL APPLICABILITY

The compounds of the present disclosure and pharmaceutically acceptable salts thereof are useful as therapeutic or prophylactic agents for conditions in which CBP/P300 is involved by potently inhibiting CBP/P300.

Sequence Listing

The invention claimed is:

1. A compound or a pharmaceutically acceptable salt thereof, wherein the compound is 2-[(1'S,3'R)-3'-fluoro-5'-{1-[1-(oxetan-3-yl)azetidin-3-yl]-1H-pyrazol-4-yl}-2,5-dioxo-2',3'-dihydrospiro[imidazolidine-4,1'-inden]-1-yl]-N-[(5-fluoropyridin-2-yl)methyl]-N-[3-(trifluoromethyl)oxetan-3-yl]acetamide.

2. A compound or a pharmaceutically acceptable salt thereof, wherein the compound is 2-[(1'S,3'R)-3'-fluoro-5'-(1-methyl-1H-pyrazol-4-yl)-2,5-dioxo-2',3'-dihydrospiro[imidazolidine-4,1'-inden]-1-yl]-N-[(4-fluorophenyl)methyl]-N-[1-methyl-3-(trifluoromethyl)azetidin-3-yl]acetamide.

3. A compound or a pharmaceutically acceptable salt thereof, wherein the compound is 2-[(1'S,3'R)-3'-fluoro-5'-(1-methyl-1H-pyrazol-4-yl)-2,5-dioxo-2',3'-dihydrospiro[imidazolidine-4,1'-inden]-1-yl]-N-[(5-fluoropyridin-2-yl)methyl]-N-[1-methyl-3-(trifluoromethyl)azetidin-3-yl]acetamide.

4. A compound or a pharmaceutically acceptable salt thereof, wherein the compound is 2-{(1'S,3'R)-3'-fluoro-5'-[1-(oxetan-3-yl)-1H-pyrazol-4-yl]-2,5-dioxo-2',3'-dihydrospiro[imidazolidine-4,1'-inden]-1-yl}-N-[(5-fluoropyridin-2-yl)methyl]-N-[1-methyl-3-(trifluoromethyl)azetidin-3-yl]acetamide.

5. A compound or a pharmaceutically acceptable salt thereof, wherein the compound is 2-[(1'S,3'R)-3'-fluoro-5'-{1-[(oxetan-3-yl)methyl]-1H-pyrazol-4-yl}-2,5-dioxo-2',3'-dihydrospiro[imidazolidine-4,1'-inden]-1-yl]-N-[(5-fluoropyridin-2-yl)methyl]-N-[1-methyl-3-(trifluoromethyl)azetidin-3-yl]acetamide.

6. A compound or a pharmaceutically acceptable salt thereof, wherein the compound is 2-[(1'S,3'R)-5'-(1-ethyl-1H-pyrazol-4-yl)-3'-fluoro-2,5-dioxo-2',3'-dihydrospiro [imidazolidine-4,1'-inden]-1-yl]-N-[(4-fluorophenyl)methyl]-N-[1-methyl-3-(trifluoromethyl)azetidin-3-yl]acetamide.

7. A pharmaceutical composition comprising the compound or the pharmaceutically acceptable salt thereof according to any one of claims 1 to 6.

8. A pharmaceutical composition comprising the compound or the pharmaceutically acceptable salt thereof according to any one of claims 1 to 6, comprised as a combination with an additional drug, wherein the additional drug is at least one selected from the group consisting of a hormonal therapy agent, a chemotherapeutic agent, an immunotherapeutic agent, and an agent inhibiting a cell growth factor and a receptor action thereof.

* * * * *